US012728153B2

(12) United States Patent
Poncz et al.

(10) Patent No.: US 12,728,153 B2

(45) Date of Patent: Sep. 8, 2026

(54) NET STABILIZATION AS A THERAPY FOR SEPSIS

(71) Applicant: THE CHILDREN'S HOSPITAL OF PHILADELPHIA, Philadelphia, PA (US)

(72) Inventors: Mortimer Poncz, Philadelphia, PA (US); Kandace Gollomp, Philadelphia, PA (US); Lubica Rauvo, Philadelphia, PA (US); Anna M. Kowalska, Philadelphia, PA (US)

(73) Assignee: The Children's Hospital of Philadelphia, Philadelphia, PA (US)

( * ) Notice: Subject to any disclaimer, the term of this patent is extended or adjusted under 35 U.S.C. 154(b) by 1324 days.

(21) Appl. No.: 17/275,412

(22) PCT Filed: Aug. 29, 2019

(86) PCT No.: PCT/US2019/048709

§ 371 (c)(1),
(2) Date: Jan. 5, 2022

(87) PCT Pub. No.: WO2020/055597

PCT Pub. Date: Mar. 19, 2020

(65) Prior Publication Data

US 2022/0175886 A1 Jun. 9, 2022

Related U.S. Application Data

(60) Provisional application No. 62/730,701, filed on Sep. 13, 2018.

(51) Int. Cl.

*A61K 38/19* (2006.01)
*A61K 39/00* (2006.01)
(Continued)

(52) U.S. Cl.

CPC ........... *A61K 38/195* (2013.01); *A61P 31/04* (2018.01); *C07K 16/24* (2013.01); *A61K 2039/505* (2013.01)

(58) Field of Classification Search

None
See application file for complete search history.

(56) References Cited

U.S. PATENT DOCUMENTS

| | | | |
|---|---|---|---|
| 6,964,854 | B1 | 11/2005 | Arepally et al. |
| 7,728,115 | B2 | 6/2010 | Arepally et al. |

(Continued)

FOREIGN PATENT DOCUMENTS

| | | |
|---|---|---|
| WO | WO 2010/040766 | 4/2010 |

OTHER PUBLICATIONS

Kowalska, et al. Endogenous platelet factor 4 stimulates activated protein C generation in vivo and improves survival after thrombin or lipopolysaccharide challenge. Blood (2007). 110:6, p. 1903-1905.*

(Continued)

*Primary Examiner* — Joanne Hama
*Assistant Examiner* — Jami Michelle Gurley
(74) *Attorney, Agent, or Firm* — pH IP Law

(57) ABSTRACT

The present disclosure is directed to the use of PF4 alone or anti-PF4 antibodies alone or the combination thereof to treat sepsis. Neutrophils release their histone-coated DNA termed neutrophil extracellular traps (NETs) during sepsis and related inflammatory disorders. NETs are broken down and release NET degradation products (NDPs) like histone that are toxic and contribute to the morbidity and mortality in sepsis and related inflammatory disorders. The inventors have shown that a native platelet protein, platelet factor 4 (PF4), which is highly positively-charged, compacts NETs that are in turn highly negatively-charged. These compact (Continued)

NETs are resistant to NDP release and breakdown by circulating DNases. PF4 protects against this lysis and NDP release and improves outcome. The inventors also found that an antibody to PF4 that cross-binds PF4 on NETs further protects against lysis and NDP release. Such antibodies, perhaps supplemented with additional PF4, are therapeutic candidates for treatment of sepsis.

17 Claims, 13 Drawing Sheets

Specification includes a Sequence Listing.

(51) Int. Cl.
*A61P 31/04* (2006.01)
*C07K 16/24* (2006.01)

(56) References Cited

U.S. PATENT DOCUMENTS

2010/0234575 A1* 9/2010 Chamberlain ..... C07K 16/2863 530/387.3
2018/0024140 A1 1/2018 Greene et al.

OTHER PUBLICATIONS

Chailyan, A., et al (2011) The association of heavy and light chain variable domains in antibodies: implications for antigen specificity FEBS Journal 278; 2858-2866.*
Haile, et al. PF4-HIT antibody (KKO) complexes activate broad innate immune and inflammatory responses. Thrombosis Research (2017). 159, p. 39-47.*
Reilly, et al. Heparin-induced thrombocytopenia/ thrombosis in a transgenic mouse model requires human platelet factor 4 and platelet activation through FcγRIIA. Blood (2001). 98:8, p. 2442-2447.*
Mayo Clinic. Patient Care & Health Information—Dagnosis & treatment—Sepsis. Nov. 8, 2017 Internet—Wayback Machine. p. 1-5.*
Liu. Pharmacokinetics of monoclonal antibodies and Fc-fusion proteins. Protein Cell (2018). 9:1, p. 15-32.*
Hummer, A.M., et al. Advances in computational structure-based antibody design Current Opinion in Structural Biology (2022), 74: 102379, p. 1-7.*
Arepally, et al. Characterization of a murine monoclonal antibody that mimics heparin-induced thrombocytopenia antibodies. Blood (2000). 95:5, p. 1533-1540.*
Pongas, et al. Antiplatelet factor 4/heparin antibodies in patients with gram negative bacteremia. Thrombosis Research (2013), 132, p. 217-220.*
Gollomp, et al. A Special Role for Neutrophil Extracellular Traps (NETs) and Neutrophils in the Prothrombotic Nature of Heparin-Induced Thrombocytopenia. Blood (2016). 128:22, p. 1023.*
Cai, et al. Atomic description of the immune complex involved in heparin-induced thrombocytopenia. Nature Communications (2015), 6:8277, p. 1-10.*
Murine hybridoma: KKO, ATCC Product Sheet, retrieved from https://www.atcc.org/Products/All/PTA-6133.aspx#generalinformation, 2018.
Arepally et al., "Characterization of a murine monoclonal antibody that mimics heparin-induced thrombocytopenia antibodies," *Blood*, 95(5):1533-40, 2000.
Brill et al., "Neutrophil extracellular traps promote deep vein thrombosis in mice," *J. Thromb. Haemost.*, 10(1):136-44, 2012.
Cines et al., "Heparin-induced thrombocytopenia: an autoimmune disorder regulated through dynamic autoantigen assembly/disassembly," *J. Clin. Apher.*, 22(1):31-6, 2007.
Dyer et al., "Deep vein thrombosis in mice is regulated by platelet HMGB1 through release of neutrophil-extracellular traps and DNA," *Sci Rep.*, 8(1):2068, 2018.
Gollomp et al., "A special role for Neutrophil Extracellular Traps (NETs) and neutrophils in the prothombotic nature of heparin-induced thrombocytopenia," *Blood*, 128(22):1023, 2016.
Gollomp et al., "Neutrophil accumulation and NET release contribute to thrombosis in HIT," *JCI Insight*, 3(18):e99445, 2018.
Gollomp et al., "Platelet Factor 4 (PF4)-Mediated Neutrophil Extracellular Trap Compaction Limits Endothelial Injury and Promotes Survival Following Lipopolysaccharide Challenge," *Blood.*, 130(Suppl. 1):997, 2017.
Haile et al., "PF4-HIT antibody (KKO) complexes activate broad innate immune and inflammatory responses," *Thromb. Res.*, 159:39-47, 2017.
Hayes et al., "Endothelial antigen assembly leads to thrombotic complications in heparin-induced thrombocytopenia," *J. Clin. Invest.*, 127(3):1090-1098, 2017.
Hurley, "Antibiotic-induced release of endotoxin. A therapeutic paradox," *Drug Saf.*, 12(3):183-195, 1995. (Summary only).
Jaax et al., "Complex formation with nucleic acids and aptamers alters the antigenic properties of platelet factor 4," *Blood*, 122(2):272-81, 2013.
Jenne et al., "Platelets: bridging hemostasis, inflammation, and immunity," *Int. J. Lab. Hematol.*, 35(3):254-61, 2013.
Kasthuri et al., "PF4/heparin-antibody complex induces monocyte tissue factor expression and release of tissue factor positive microparticles by activation of FcγRI," *Blood*, 119(22):5285-93, 2012.
Khairy et al., "Polymorphonuclear leukocyte and monocyte activation induced by plasma from patients with heparin-induced thrombocytopenia in whole blood," *Thromb. Haemost.*, 92(6):1411-9, 2004.
Kowalska et al., "Endogenous platelet factor 4 stimulates activated protein C generation in vivo and improves survival after thrombin or lipopolysaccharide challenge," *Blood*, 110(6):1903-1905, 2007.
Koyama et al., "Combination of thrombin-antithrombin complex, plasminogen activator inhibitor-1, and protein C activity for early identification of severe coagulopathy in initial phase of sepsis: a prospective observational study," *Crit Care*, 18(1):R13, 2014.
Krauel et al., "Platelet factor 4 binds to bacteria, [corrected] inducing antibodies cross-reacting with the major antigen in heparin-induced thrombocytopenia," *Blood*, 117(4):1370-1378, 2011.
Lande et al., "CXCL4 assembles DNA into liquid crystalline complexes to amplify TLR9-mediated interferon-alpha production in systemic sclerosis," *Nat Commun.*, 10(1):1731, 2019.
Mai et al., "Delayed but not Early Treatment with DNase Reduces Organ Damage and Improves Outcome in a Murine Model of Sepsis," *Shock*, 44(2):166-172, 2015.
Martinod and Wagner, "Thrombosis: tangled up in NETs," *Blood*, 123(18):2768-76, 2014.
Martinod et al., "PAD4-deficiency does not affect bacteremia in polymicrobial sepsis and ameliorates endotoxemic shock," *Blood*, 125(12):1948-1956, 2015.
Mayadas et al., "Mechanisms of immune complex-mediated neutrophil recruitment and tissue injury," *Circulation*, 120(20):2012-24, 2009.
McDonald et al., "Intravascular neutrophil extracellular traps capture bacteria from the bloodstream during sepsis," *Cell Host Microbe.*, 12(3):324-333, 2012.
McDonald et al., "Platelets and neutrophil extracellular traps collaborate to promote intravascular coagulation during sepsis in mice," *Blood*, 129(10):1357-1367, 2017.
O'Brien et al., "Consequences of extracellular trap formation in sepsis," *Curr Opin Hematol.*, 24(1):66-71, 2017.
PCT International Invitation to Pay Additional Fees issued in International Application No. PCT/US22019/048709, dated Nov. 18, 2019.
PCT International Search Report and Written Opinion issued in International Application No. PCT/US22019/048709, dated Jan. 30, 2020.
PF4 Monoclonal Antibody (KKO), Product Data Sheet, ThermoFischer Scientific, retrieved from https://www.thermofisher.com/antibody/primary/target/PF4, accessed Sep. 6, 2018.

(56) References Cited

OTHER PUBLICATIONS

Qiao et al., "The platelet Fc receptor, FcgammaRIIa," *Immunol. Rev.*, 268(1):241-52, 2015.
Reilly et al., "Heraprin-induced thrombocytopenia/thrombosis in a transgenic mouse model requires human platelet factor 4 and platelet activation through FcγRIIA," *Hemostasis, Thrombosis, and Vascular Biology*, 98:2442-2447, 2001.
Sarkar et al., "Antibody Stabilization of Neutrophil Extracellular Trap-Platelet Factor 4 Complexes Is Therapeutic in a Murine Model of Endotoxemia," *Blood*, 132(Suppl. 1):271-271, 2018.
Schauer et al., "Aggregated neutrophil extracellular traps limit inflammation by degrading cytokines and chemokines," *Nat. Med.*, 20(5):511-517, 2014.
Shrum et al., "A robust scoring system to evaluate sepsis severity in an animal model," *BMC Res Notes*, 7:233, 2014.
Wolach et al., "Increased neutrophil extracellular trap formation promotes thrombosis in myeloproliferative neoplasms," *Sci Transl Med.* 10(436), 2018.
Xiao et al., "Immune complexes formed following the binding of anti-platelet factor 4 (CXCL4) antibodies to CXCL4 stimulate human neutrophil activation and cell adhesion," *Blood*, 112(4):1091-100, 2008.

* cited by examiner

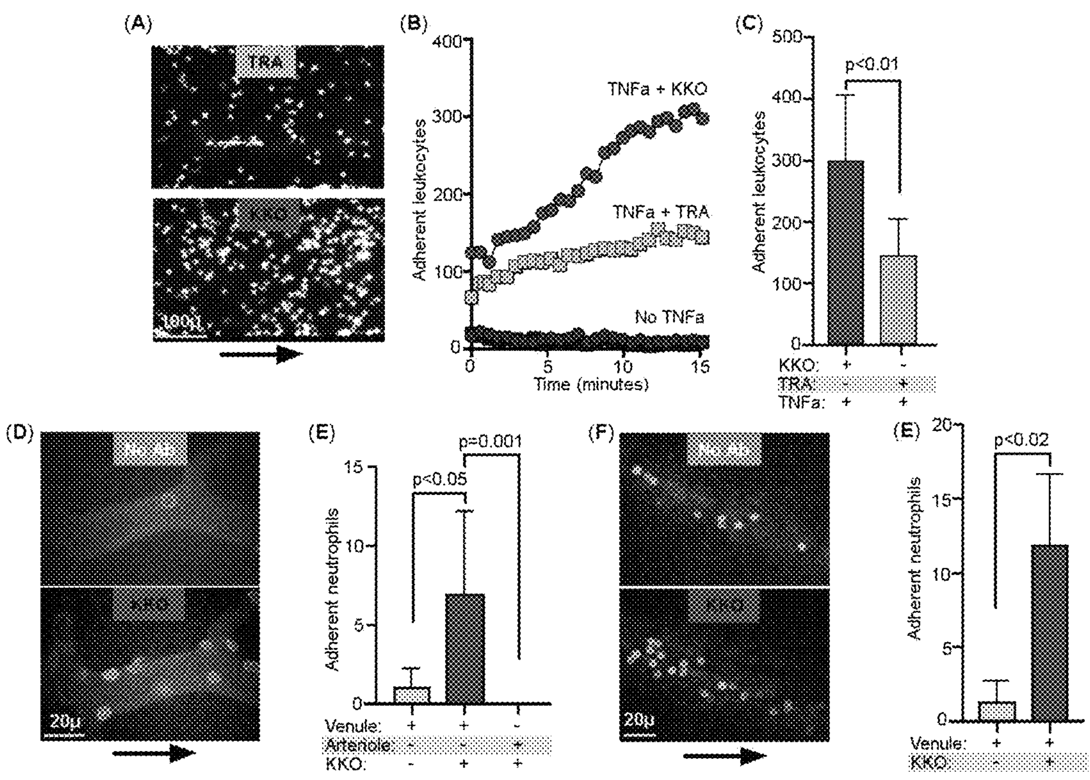
FIGS. 1A-G
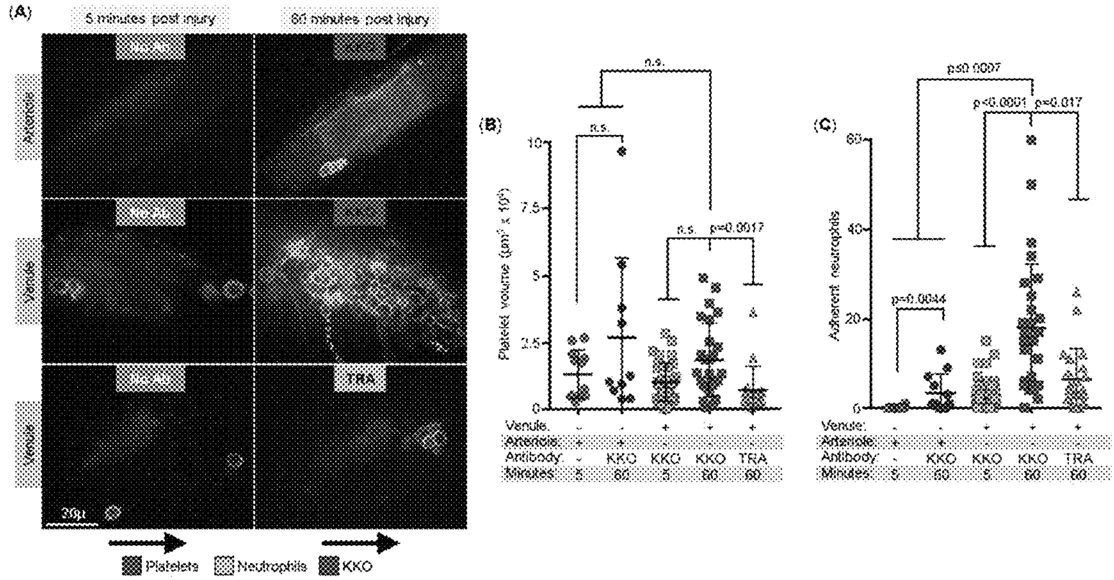
FIGS. 2A-C

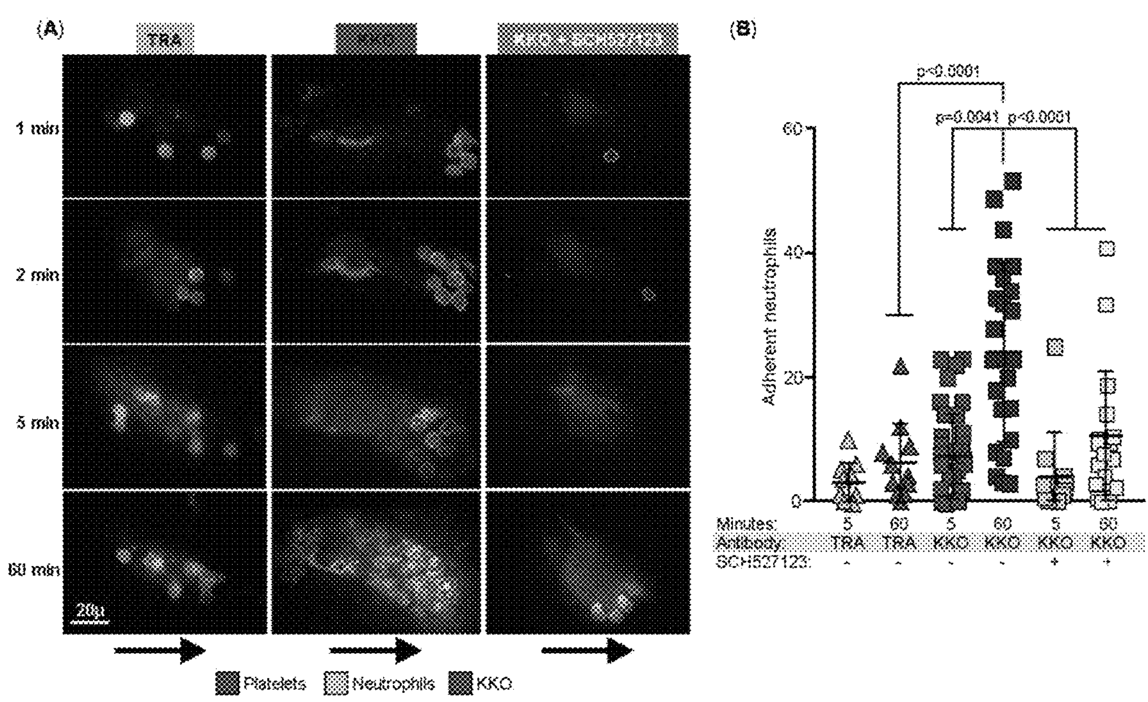
FIGS. 3A-B
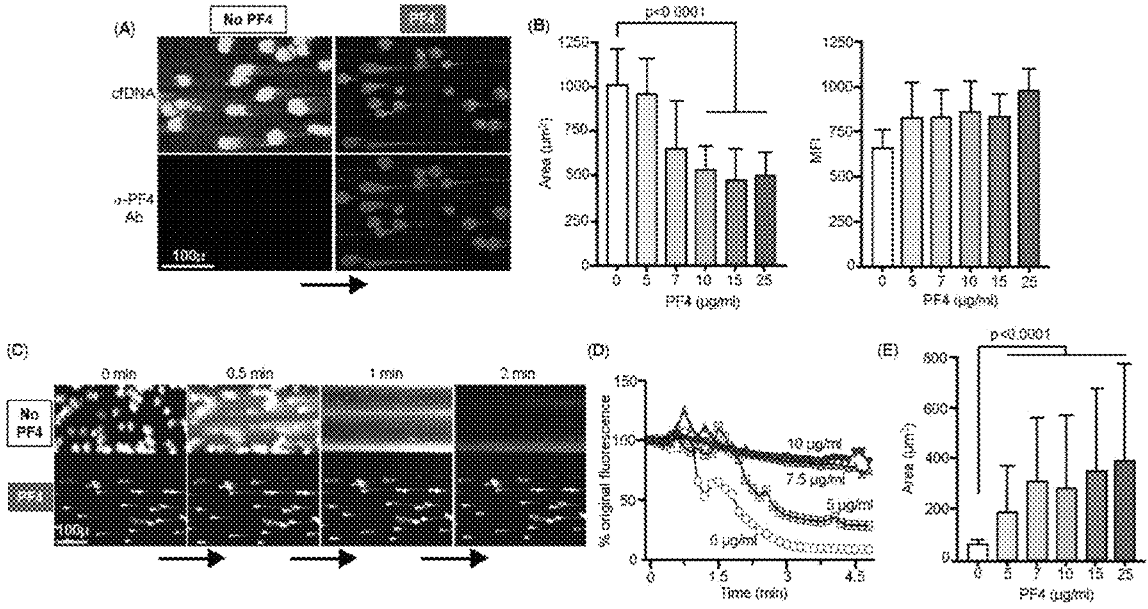
FIGS. 4A-E

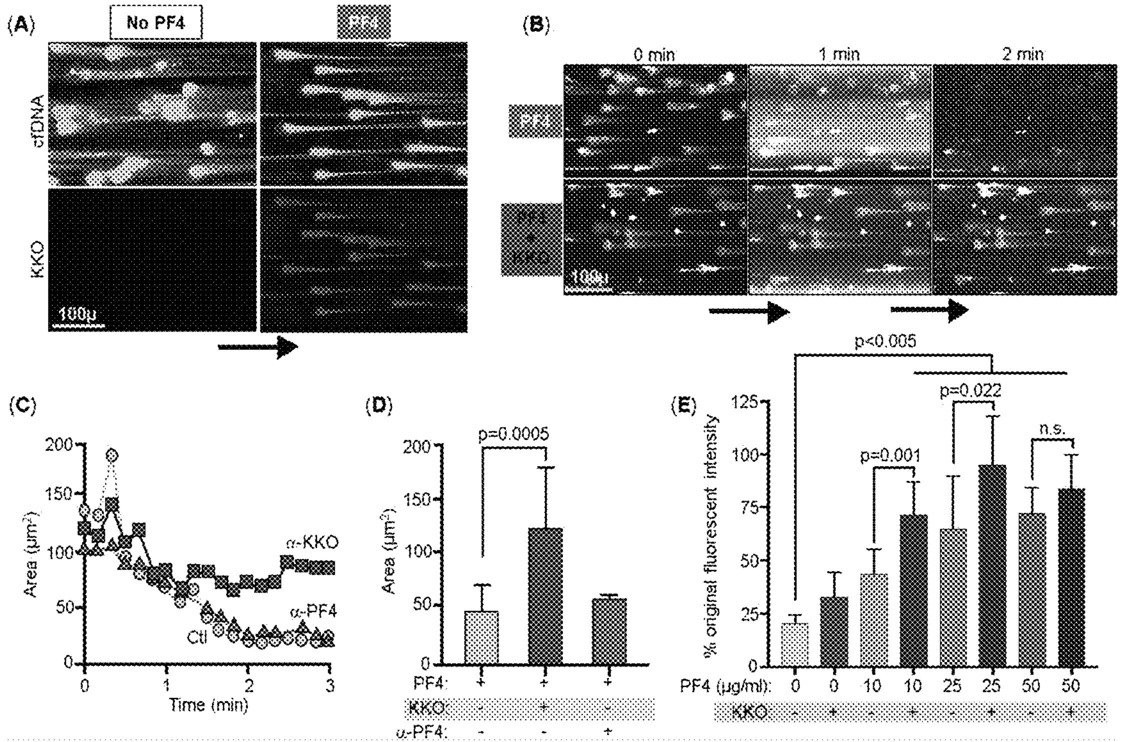
FIGS. 5A-E

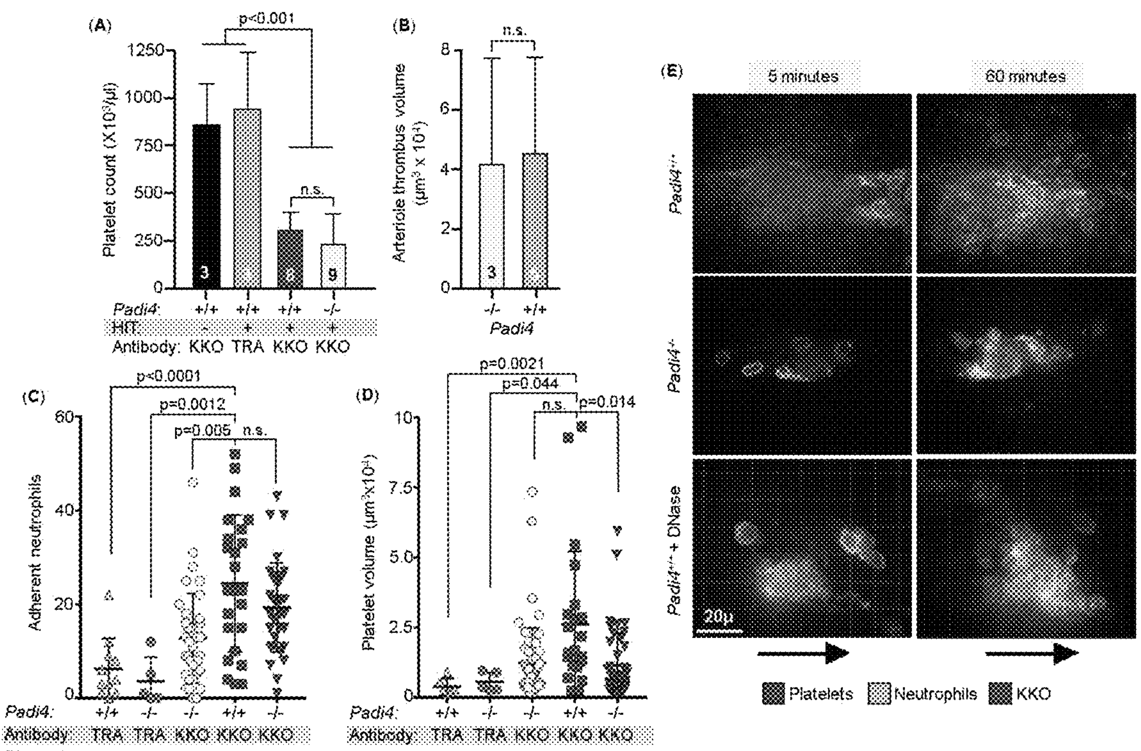
FIGS. 6A-E

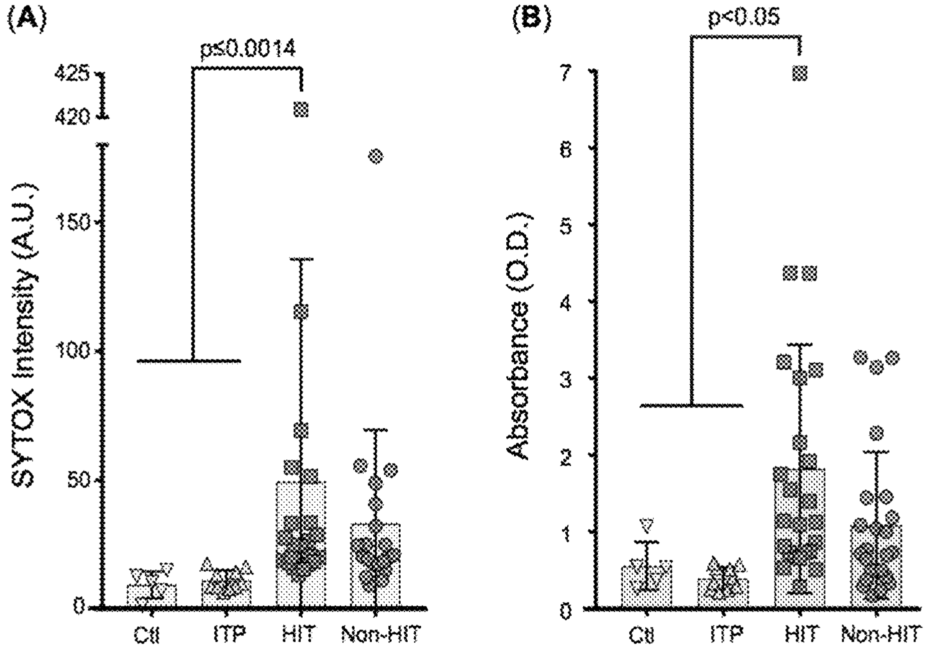
FIGS. 7A-B

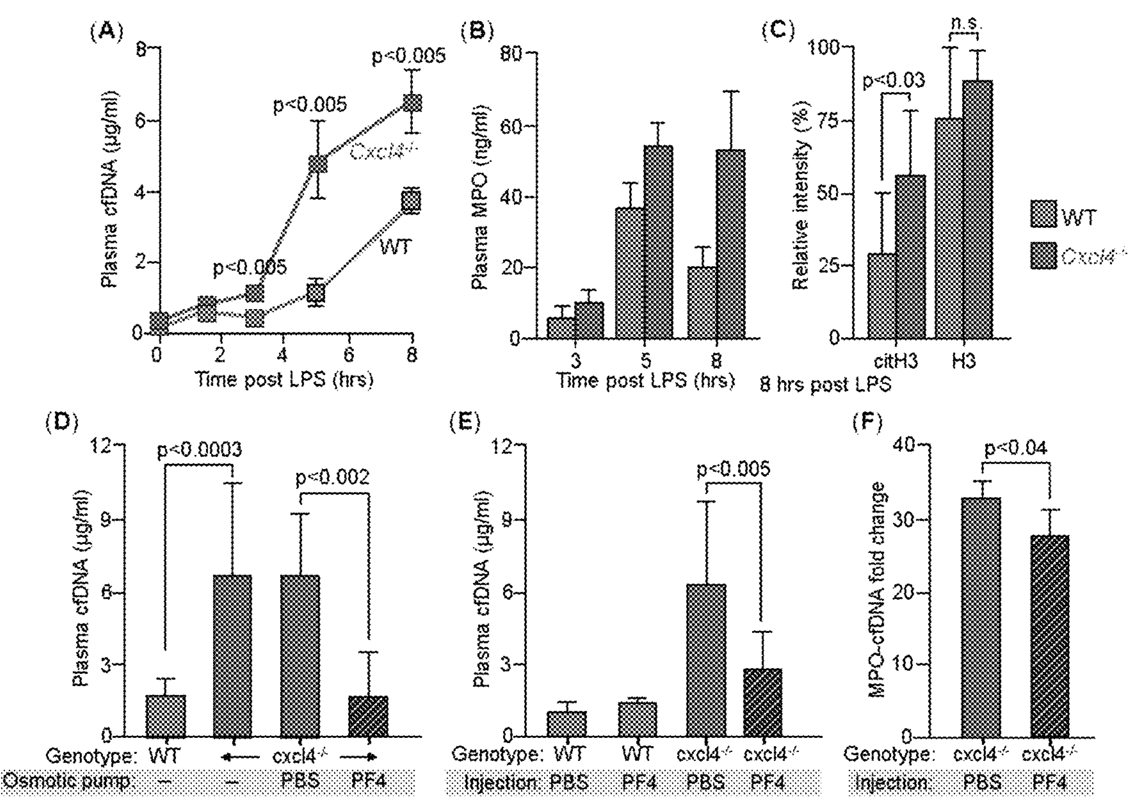
FIGS. 8A-F
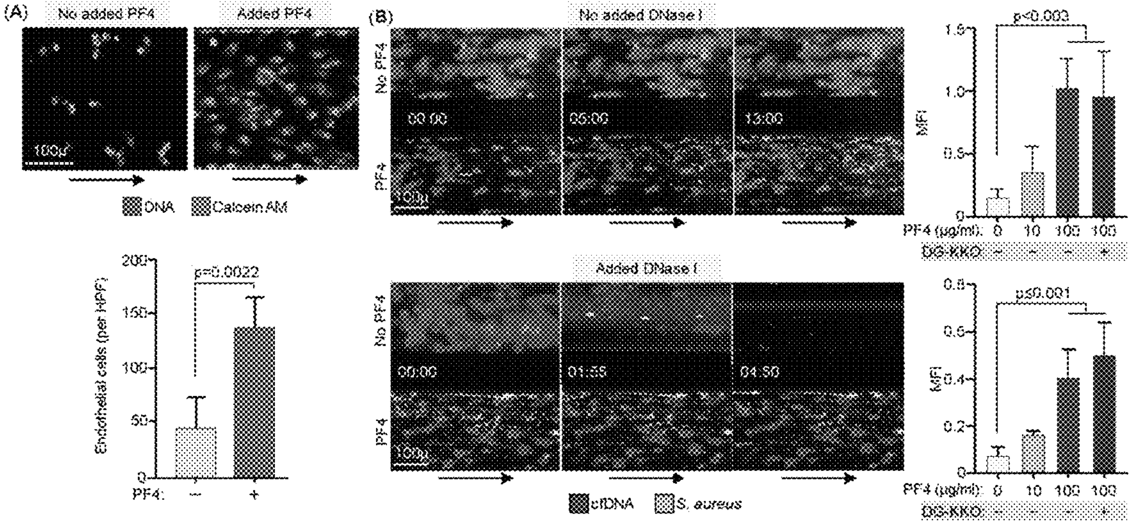
FIGS. 9A-B

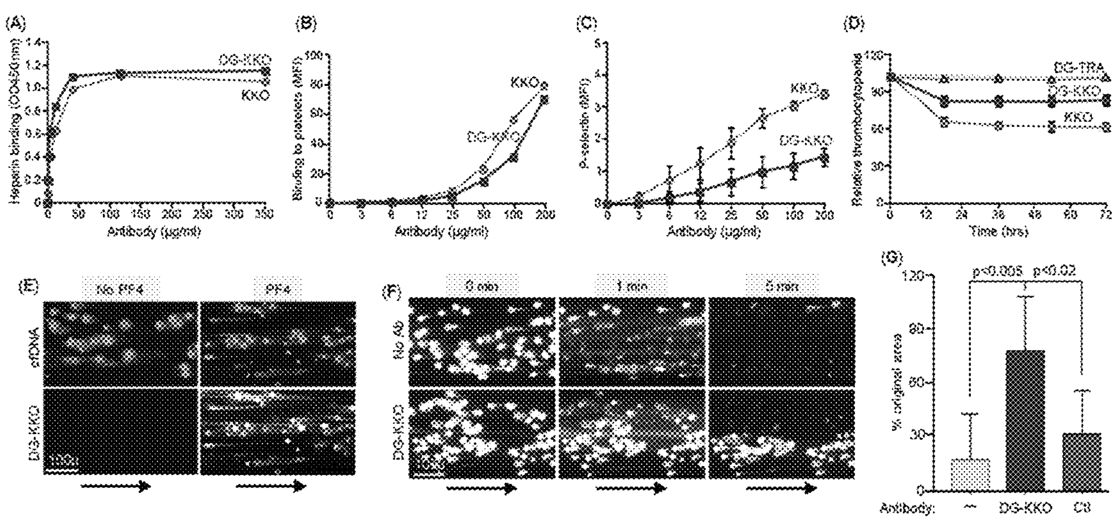
FIGS. 10A-G
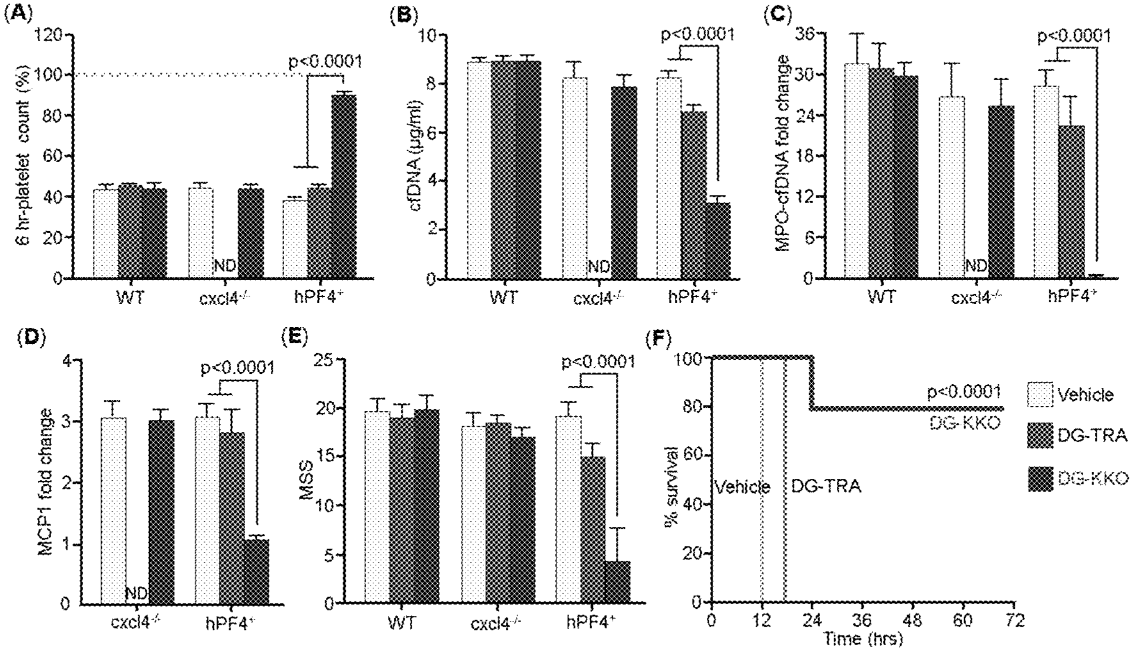
FIGS. 11A-F

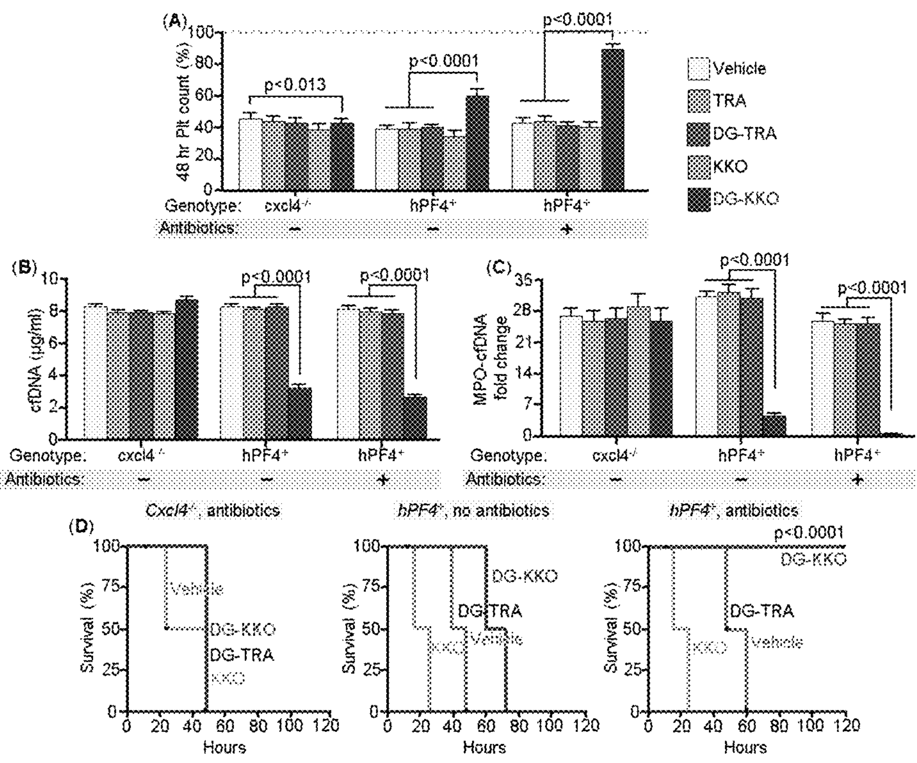
FIGS. 12A-D
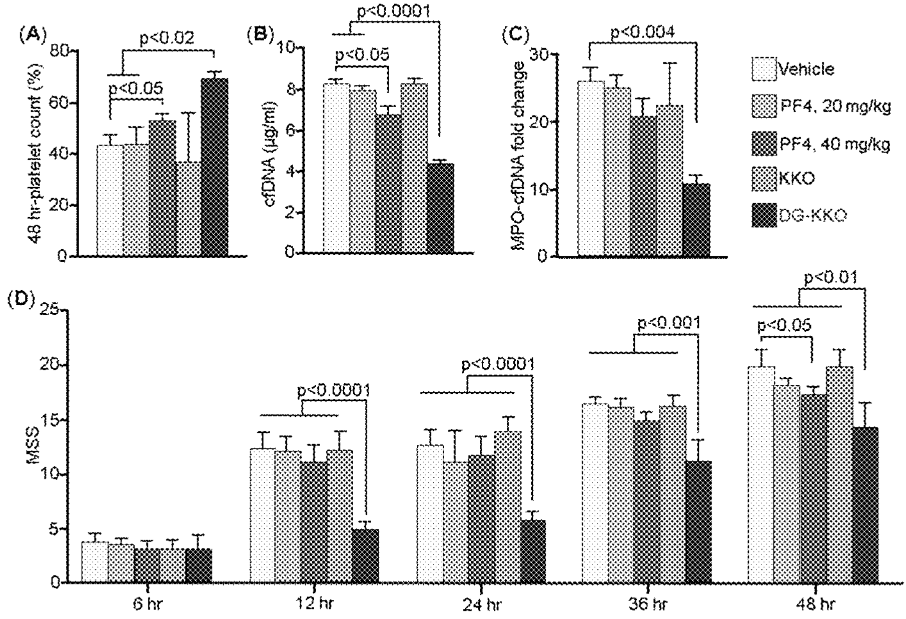
FIGS. 13A-D

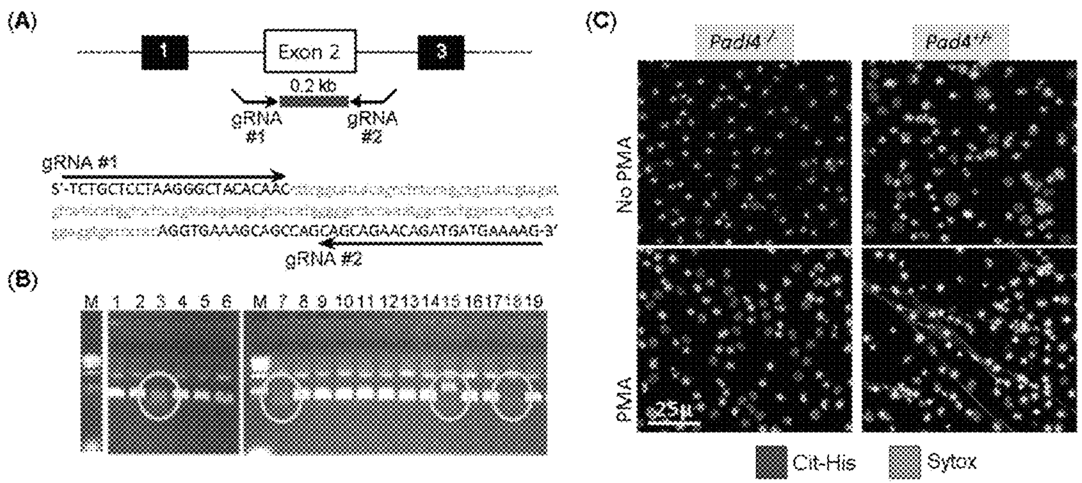
FIGS. 15A-C
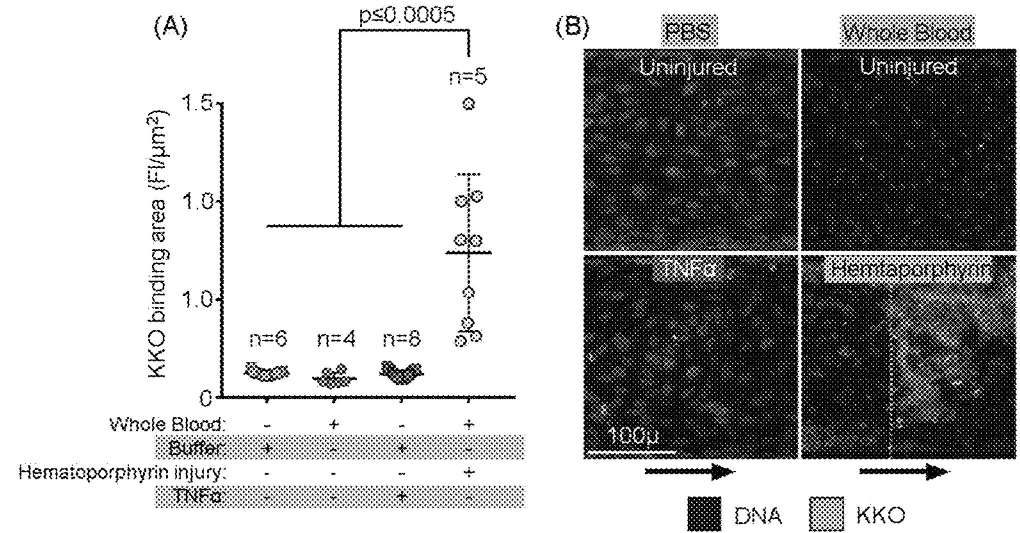
FIGS. 16A-B

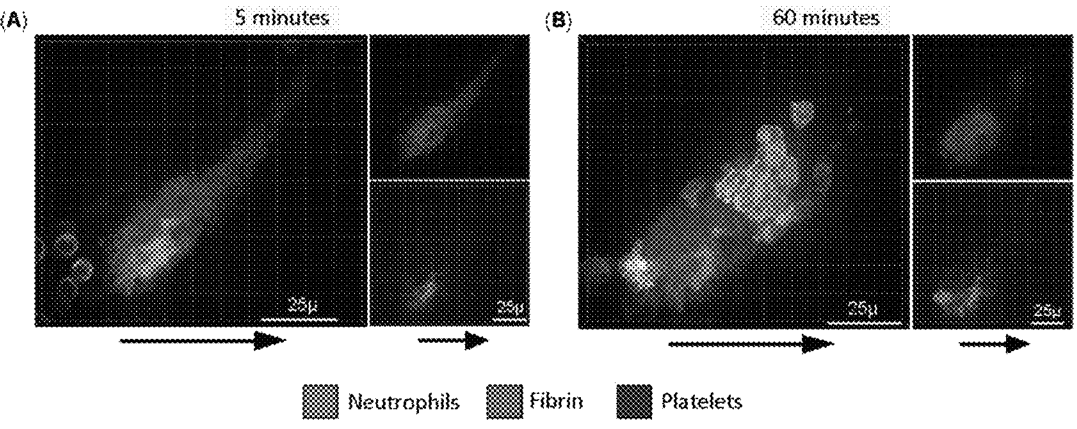
FIGS. 17A-B
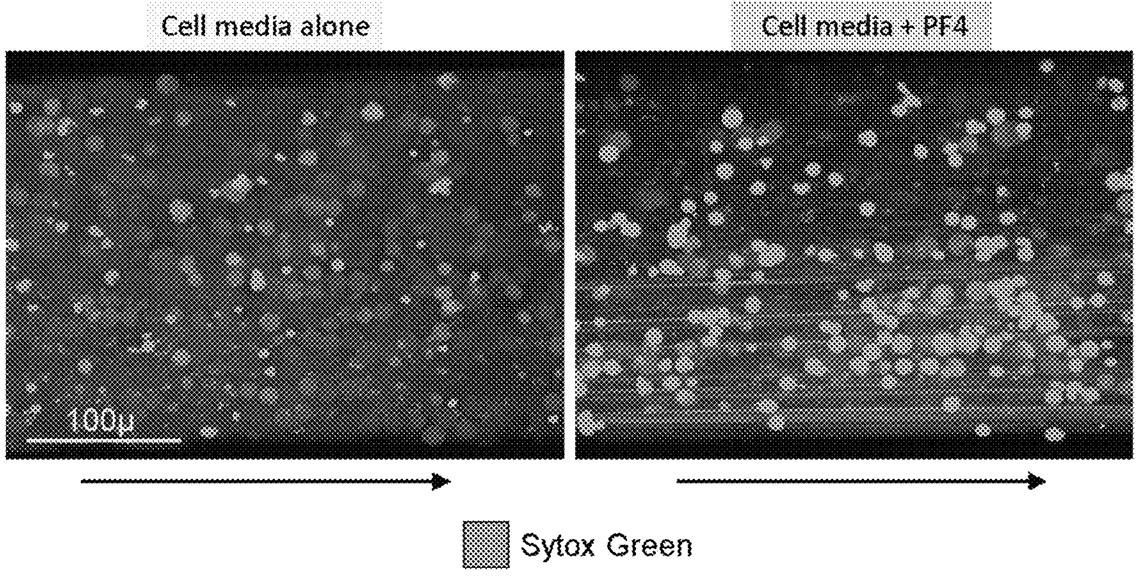
FIG. 18

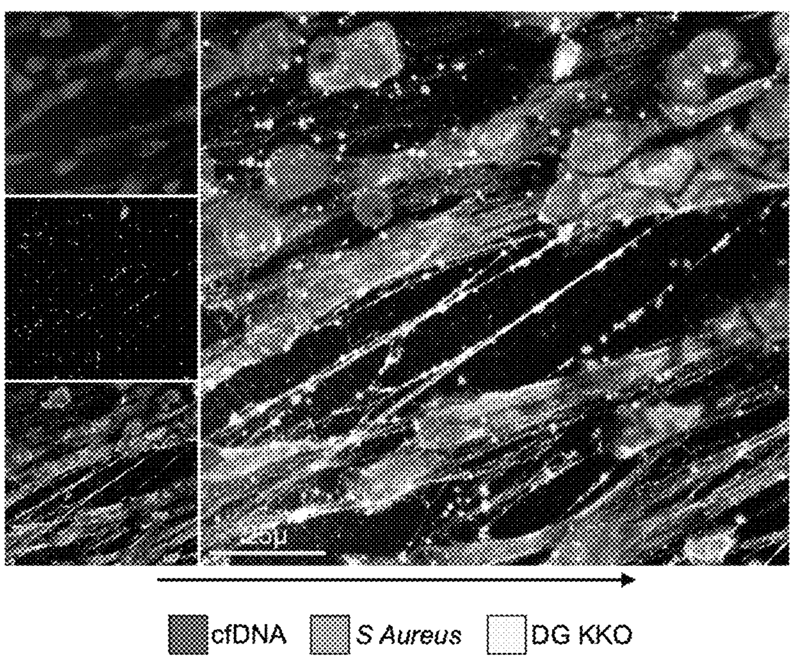
FIG. 19
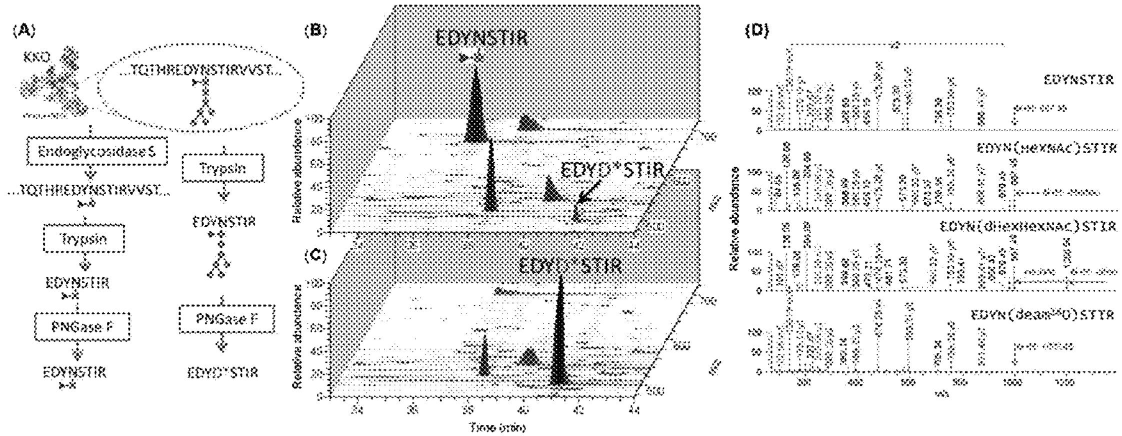
FIGS. 20A-C

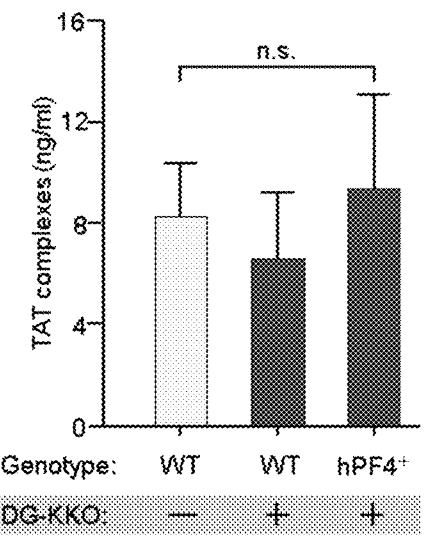
FIG. 21
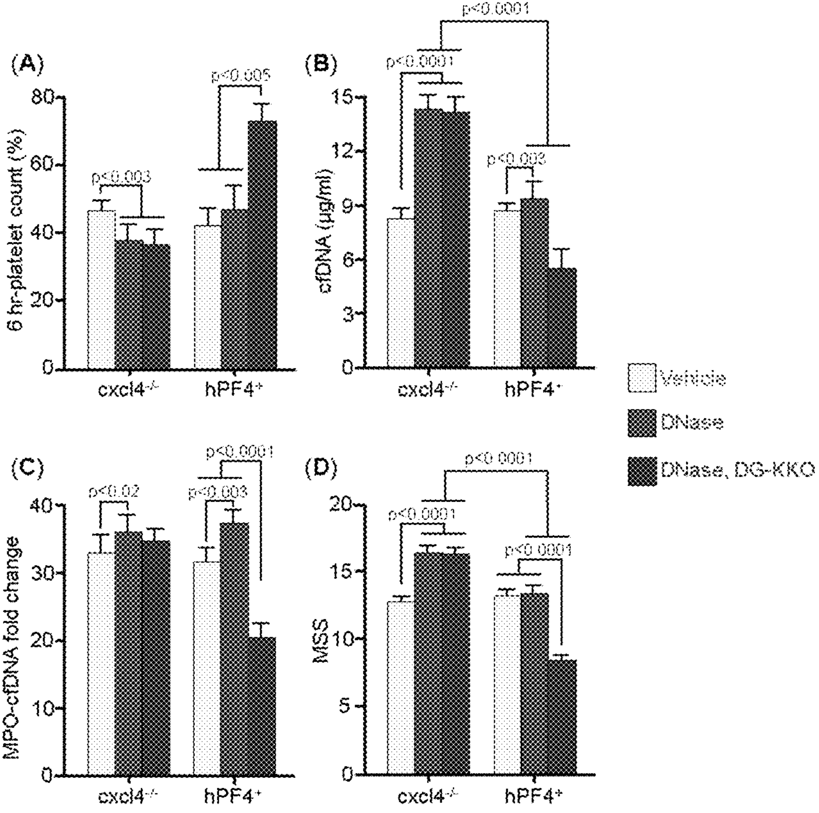
FIGS. 22A-D

NET STABILIZATION AS A THERAPY FOR SEPSIS

PRIORITY CLAIM

This application is a national phase application under 35 U.S.C. § 371 of International Application No. PCT/US2019/048709, filed Aug. 29, 2019, which claims benefit of priority to U.S. Provisional Application Ser. No. 62/730,701, filed Sep. 13, 2018, the entire contents of each of which are hereby incorporated by reference.

This invention was made with government support under grant nos. R01 HL139448 and T32 HL007150 from the National Institutes of Health. The government has certain rights in the invention.

BACKGROUND

Pursuant to 37 C.F.R. 1.821(c), a sequence listing is submitted herewith as an ASCII compliant text file named "CHOPP0022US_ST25.txt", created on Apr. 7, 2026 and having a size of ~3.64 kilobytes. The content of the aforementioned file is hereby incorporated by reference in its entirety

1. Field of the Disclosure

The present disclosure relates generally to the fields of medicine, molecular biology and immunology. More particular, the disclosure relates to the use of agents that cross-link neutrophil extracellular traps (NETs) such as anti-platelet factor 4 (PF4) antibodies to treat and prevent sepsis.

2. Background

Prior study of the release of NETs and their interaction with PF4 in heparin-induced thrombocytopenia (HIT). HIT is an immune-mediated thrombocytopenic disorder, characterized by venous and arterial thrombi (Nand et al., 1997). Even with early recognition and initiation of appropriate therapy, thromboembolic complications can still occur (Wallis et al., 1999). The current standard of care for patients with suspected HIT involves intense anticoagulation that carries the risk of significant bleeding and only provides partial protection against recurrent thromboembolic events (Kelton et al., 2008). While avoidance of heparin exposure may prevent the development of HIT (Linkins et al., 2012), there are clinical settings where heparin remains irreplaceable (Zhou et al., 2012). An improved understanding of the pathobiology of HIT may help identify targeted therapies to prevent thrombosis without subjecting patients to the risk of intense anticoagulation. These insights may also be beneficial in the treatment of other inflammatory, prothrombotic conditions ranging from antiphospholipid syndrome (Cervera, R., 2017) to sepsis (Donze et al., 2014).

HIT is caused by the development of pathogenic antibodies (HIT antibodies) that recognize complexes of heparin and the platelet-specific human chemokine PF4 (CXCL4) (Rauova et al., 2006), which is released in high concentrations at sites of platelet activation and then binds to surface glycosaminoglycans (GAGs) on platelets (Rauova et al., 2009), monocytes (Rauova et al., 2010), endothelial cells (Hayes et al., 2017), and neutrophils (Arepally, G., 2017). HIT antibodies cross-react with PF4-GAG complexes after which their Fc termini engage FcγRIIa receptors, leading to cell activation (Poncz, M., 2005). Although the high risk of thrombosis observed in HIT has classically been attributed to the assembly of PF4-GAG complexes on platelets, these complexes also form on the surface of other cells types, including monocytes (Rauova et al., 2010) and neutrophils (Xiao et al., 2008). Moreover, the inventors recently showed that PF4 and HIT-like antibodies bind predominantly to the endothelial surface after vessel wall injury, leading to an increase in the extent of endothelial damage (Hayes et al., 2017).

There are multiple factors that suggest neutrophils may contribute to the pathogenesis of HIT. Human neutrophils express FcγRIIa (Qiao et al., 2015), and neutrophil activation via this receptor promotes increased phagocytosis, degranulation, and generation of reactive oxygen species (Mayadas et al., 2009). PF4 and HIT antibodies have been shown to induce integrin expression on neutrophils (Xiao et al., 2008) and enhance the formation of neutrophil-platelet aggregates (Khairy et al., 2004). Myeloperoxidase levels have also been found to be elevated in plasma obtained from patients with HIT compared to plasma from patients with other causes of thrombocytopenia (Khairy et al., 2004), suggesting that HIT is associated with neutrophil activation. In the setting of infection or inflammation, activated neutrophils can contribute to thrombus formation through neutrophil extracellular traps (NETs), released chromatin that can trap platelets, bind clotting factors, and deactivate natural anticoagulants (Martinod and Wagner, 2014). However, attempts to intervene in HIT by modulating neutrophil function has not been explored.

SUMMARY

The inventors propose that NET stabilization and prevention of release of toxic NET degradation products (NDPs) is a new therapeutic approach in HIT, that drugs that do so may either act like PF4 and physically compact the NETs protecting them from lysis by DNase I and other enzymes, enhancing their ability to entrap bacteria and likely by neutralizing lipopolysaccharides released from bacterial cell walls. PF4 is known to bind to polyanions and form cross-linked aggregates in instigating the prothrombotic disorder HIT, but the inventors now propose to be useful to treat sepsis. Moreover, antibodies that cross-link NETs are pathogenic in HIT, but if their Fc portions are modified to eliminate cell activation they may be a therapeutic intervention. Other antibodies that bind directly to DNA as seen with lupus-related antibodies may have similar application for therapeutic intervention in sepsis. An example of such a HIT-like antibody with such potential therapeutic use is termed KKO. In the case of such antibodies the Fc portion of these antibodies need to be altered to avoid untoward side-effects via Fc receptor activation and/or complement activation that would lead to a proinflammatory process.

Thus, in accordance with the present disclosure, there is provided a method of treating a subject having or at risk of developing a neutrophil extracellular trap (NET)-associated disease or syndrome comprising administering to said subject PF4 or a related cationic protein or an Fc-modified antibody or fragment thereof that binds immunologically to NETs directly or via the PF4 bound to the NETs reducing DNase lysis, improving NDP sequestration and microbial entrapment and likely neutralizing freed LPS from bacterial cell walls. The said Fc-modified antibody exhibits reduced binding to FcR and/or complement activation as compared to an unmodified antibody of the same class and isotype.

The subject may be a human or a non-human mammal. The subject may have the disease or syndrome or may be at risk of having the disease or syndrome. The method may further comprise treating said subject with a second therapy, such as an anti-sepsis therapy, such as an antibiotic, IV fluids, blood products, a vasopressor, or a steroid. The disease or syndrome may be sepsis, vasculitides, systemic lupus erythematosus, antiphospholipid syndrome, metastatic cancer, tumor lysis state, severe trauma or sickle cell disease.

The antibody may be a deglycosylated antibody, or an antibody modified by a mutation in the Fc domain by an amino acid substitution, or an IgG subclass switch. The antibody or antibody fragment may be administered intravenously, intra-arterially, intramuscularly or subcutaneously. The antibody or antibody fragment and/or the second therapy may be administered only once or more than once. The antibody may be an IgG or IgM. The antibody or antibody fragment may bind to the same PF4 epitope as antibody KKO or other site or directly to the DNA contained within the NET. The antibody may be a monoclonal antibody (moAb) or may be part of a population of polyclonal antibodies.

In another embodiment, there is provided an antibody or antibody fragment that binds immunologically to platelet factor 4 (PF4) or PF4/heparin, wherein said antibody exhibits reduced binding to FcR and/or complement activation as compared to an unmodified antibody of the same class and isotype. The antibody may be a deglycosylated antibody, or is an antibody modified by a mutation in the Fc domain by an amino acid substitution or is an IgG subclass switch. The antibody may be formulated in a pharmaceutically acceptable excipient, and/or may be formulated with an antibiotic, IV fluids, blood products, a vasopressor, or a steroid. The antibody may be an IgG or IgM. The antibody or antibody fragment may bind to the same epitope as antibody KKO. The antibody may be a moAb or may be part of a population of polyclonal antibodies.

Yet another embodiment provides a pharmaceutical formulation comprising platelet factor 4 (PF4) and one or more of an antibiotic, IV fluids, a blood product, a vasopressor, or a steroid.

In still yet another embodiment, there is provided a method of treating a subject having or at risk of developing a neutrophil extracellular trap (NET) associated disease or syndrome comprising administering to said subject platelet factor (PF4) or PF4/heparin. The subject may be a human or a non-human mammal. The disease or syndrome may be sepsis, vasculitides, systemic lupus erythematosus, antiphospholipid syndrome, metastatic cancer, tumor lysis state, severe trauma or sickle cell disease. The subject may have the disease or syndrome or may be at risk of having the disease or syndrome. The method may further comprise treating said subject with a second therapy, such as an anti-sepsis therapy, such as an antibiotic, IV fluids, blood products, a vasopressor, or a steroid. The PF4 may be administered intravenously, intra-arterially, intramuscularly or subcutaneously. The PF4 and/or the second therapy may be administered more than once.

Therapeutic combination of PF4 and an Fc-modified antibody like KKO that binds to PF4 bound to NETs is also contemplated. Combined intervention by both may be more effective than each alone. The disease or syndrome may be sepsis, vasculitides, systemic lupus erythematosus, antiphospholipid syndrome, metastatic cancer, tumor lysis state, severe trauma or sickle cell disease. The subject may have the disease or syndrome or may be at risk of having the disease or syndrome. The method may further comprise treating said subject with a second therapy, such as an anti-sepsis therapy, such as an antibiotic, IV fluids, blood products, a vasopressor, or a steroid. The PF4 plus antibody may be administered intravenously, intra-arterially, intramuscularly or subcutaneously. The PF4 plus antibody and/or the second therapy may be administered more than once.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein. FIGS. 1-7 and FIGS. 15-17 are background data as the concepts of applying observations made in the etiology of a prothrombotic state in HIT to a beneficial outcome in sepsis if the HIT antibody is Fc-modified. The others directly pertain to data supporting a beneficial role of human (h) PF4 and Fc-modified deglycosylated KKK (DG-KKO) in sepsis.

FIGS. 1A-G. Enhanced leukocyte-endothelial adhesion in HIT in the study of the role of neutrophils in HIT directed at NETs in sepsis. (FIG. 1A) Calcein-AM labeled blood incubated with KKO (red) or TRA (blue, an isotype control antibody for KKO) was infused through HUVEC-lined channels exposed to tumor necrosis factor (TNF) u. Representative widefield image of leukocytes (white) adhering to the endothelium is shown. Size bar and arrow indicating direction of flow are included. Image was obtained with an AXIO™ Observer Z1 inverted microscope using 10× magnification. (FIG. 1B) Leukocyte-endothelial adhesion was quantified for KKO (red) and TRA (blue). Six channels were studied in each TNFα-exposed arm (lighter colors) and 3-5 channels in the unexposed arms (darker colors). (FIG. 1C) The final number of adherent leukocytes at 15 minutes is shown as mean±1 standard deviation (SD). Comparative analysis was performed by Student's t-test. (FIG. 1D) Representative confocal image of neutrophils rolling in a venule before and after KKO infusion. Neutrophils were stained using anti-Ly-6G F(ab')$_2$ fragment (green). Size bar and arrow indicating direction of flow are included. Images were obtained with an Olympus BX61WI microscope with a 40×/0.8 numeric aperture water-immersion objective lens. (FIG. 1E) Neutrophil adhesion to cremaster arterioles and venules was studied in the HIT murine model prior to and 30 minutes after exposure to KKO. Adhesion was defined as neutrophil immobilization for ≥30 seconds. Seven and four animals were studied in the venular and arteriole arm, respectively. Statistical comparison of binding was preformed using a Kruskall-Wallis one-sided ANOVA. (FIG.

1F) Representative confocal image of neutrophil rolling and adhering to the femoral vein before and 15 minutes after the infusion of KKO. Images are as in FIG. 1D. Size bar and arrow indicating direction of flow are included. (FIG. 1G) Graph representing neutrophil adhesion to the femoral vein±KKO infusion as in FIG. 1F. N=4 per arm. Statistical comparison was performed by Student's t-test.

FIGS. 2A-C. Effect of HIT of neutrophil accumulation in cremaster vessels pre- and post-injury pursued for the same objective as FIGS. 1A-G. (FIG. 2A) Representative confocal images from cremaster arteriole and venule laser injuries showing platelets labeled with anti-CD41 (dark blue) and neutrophils labeled with anti-Ly-6G (green). Paired images from the same vessel taken at 5 and 60 mins following laser injury. KKO or TRA were infused intravenously beginning at minute 5 after injury. Size bar and arrow indicating direction of flow are included. Same microscope and acquisition software as in FIG. 1D. (FIGS. 2B-C) Graphs quantifying adherent neutrophils and platelets in the same thrombi, respectively. Twenty-eight injuries were made in twelve KKO-treated mice. Sixteen injuries were made in four TRA-treated mice. Twelve arteriole injuries were made in three untreated and three KKO-treated mice. Individual data points and mean±1 SD are shown. Comparative statistical analysis between 3 or more groups was performed by Kruskall-Wallis one-way ANOVA and comparisons between two groups was performed with a Student's t-test.

FIGS. 3A-B. Chemokine-dependency of neutrophil accumulation into venous thrombi in HIT pursued for the same objective as FIGS. 1A-G. (FIG. 3A) Representative confocal images of cremaster venule injuries showing platelet (blue), neutrophil (green) and KKO staining (red) at 1-60 minutes following laser injury. Typical injuries are shown from mice infused with TRA, KKO, and KKO+SCH527123, a CXCR2 antagonist (Holz et al., 2010). Size bar and arrow indicating direction of flow are included. Same microscope and acquisition software as described in FIG. 1D. (FIG. 3B) Graphs quantifying adherent neutrophils in venule thrombi 5 and 60 min following laser injury. Thirty-two injuries were made in 12 KKO-treated mice. Seventeen injuries were made in 3 TRA-treated mice. Eleven injuries were made in 3 KKO+SCH527123-treated mice. Individual data points and mean±1 SD are shown. Comparative statistical analysis was performed by Kruskall-Wallis one-way ANOVA.

FIGS. 4A-E. Microfluidic studies illustrating PF4-NET interactions and providing insight into PF4 stabilization of NETs applied to sepsis therapy. (FIG. 4A) Representative confocal images of NETs exposed to PF4 or buffer, demonstrating change in morphology. PF4 specifically adhered to the NET DNA, visualized by labeling with a polyclonal anti-PF4 antibody (α-PF4 Ab), causing the NETs to become compact. Side bar and arrow indicating direction of flow are included. Same microscope and acquisition software as in FIG. 1A. (FIG. 4B) Mean±1 SD of area covered by NETs exposed to the indicated PF4 concentration is shown on the left. Simultaneously measured mean fluorescent intensity (MFI) of SYTOX-labeled cfDNA is shown on the right. For both, N=3-6 channels per PF4 concentration, with visualization of 30-60 NETs per channel. Comparative statistical analysis was performed by Kruskall-Wallis one-way ANOVA. (FIG. 4C) Representative widefield images of NETs±PF4 (10 μg/ml), simultaneously infused with DNase I (100 U/ml). Near complete digestion of NETs not exposed to PF4 occurred within two minutes, whereas NETs compacted with PF4 remained intact. Size bar and arrows indicating direction of flow are included. (FIG. 4D) Graph showing representative changes in NET fluorescent intensity observed over a 5-minute infusion of DNase I (100 U/ml) in the presence of 0-10 μg/ml PF4. These studies were based on analysis of 3-4 channels for each condition with 30-60 NETs observed in each channel. (FIG. 4E) Confocal images were taken of 3 channels per condition following digestion and the residual mean volume±1 SD of 30-100 NETs per channel was measured. Comparative statistical analysis was done by Kruskall-Wallis one-way ANOVA.

FIGS. 5A-E. Microfluidic studies examining HIT-antibody PF4-NET complex interactions and providing insights antibody stabilizing PF4-NETs and applied to sepsis therapy. (FIG. 5A) Representative confocal images of activated neutrophils adherent to fibronectin-coated channels and stained for cfDNA (white) and KKO binding (red) in the absence and presence of 6.5 μg/ml PF4. Size bar and arrow indicating direction of flow are included. Same microscope and acquisition software as described in FIG. 1A. (FIG. 5B) Representative widefield images of adherent neutrophils as in FIG. 5A, but in the presence of 100 U/ml DNase I and 6.5 μg/ml PF4±25 μg/ml KKO over 2 minutes. Size bar and arrow indicating direction of flow are included. (FIG. 5C) Graph showing the decrease in NET area over a 3-minute DNase I digestion. (FIG. 5D) Mean±1 SD of the final area of NETs following a 5-minute infusion of DNase I (100 U/ml) in the presence of 6.5 μg/ml PF4 and KKO or an anti-PF4 antibody (uPF4), each at 25 μg/ml. N=12 in the PF4 and the PF4+KKO treated arms. N=3 in the uPF4 treated arm. Comparative statistical analysis was performed by Kruskall-Wallis one-way ANOVA. (FIG. 5E) PF4-induced resistance to DNase digestion under static conditions was measured using a previously described NET degradation assay (Hakkim et al., 2010). The graph shows the mean percent original fluorescent intensity±1 SD. N=9-10 per arm. Comparative statistical analysis between 3 or more groups was performed by Kruskall-Wallis one-way ANOVA and comparisons between two groups was performed with the Student's t-test.

FIGS. 6A-E. NETosis studies in the passive immunization Padi4$^{-/-}$/HIT mouse model. Peptidyl arginine deiminase, type IV (PAD4) is an enzyme necessary for the formation and release of NETs from neutrophils and its gene is known as Padi4 in mice with the creation of this mouse described in FIG. 15. (FIG. 6A) Platelet counts 4 hours after intraperitoneal injection of KKO or TRA in HIT or FcγRIIA$^{+}$, hPF4$^{-/-}$ ("HIT-") mice. The hPF4 transgene means that the mice express human PF4 in its platelets. Such mice are needed as virtually all HIT antibodies do not bind mice PF4, only human PF4, and that requires a polyanion like heparin to be present as well. Padi4 status is indicated. Mean±1 SD is shown. Number of mice studied per arm is indicated in bars. Comparative statistical analysis was performed by Kruskall-Wallis one-way ANOVA. (FIG. 6B) Same as in FIG. 6A, but for arteriole thrombus size after KKO infusion in HIT mice with Padi4 status indicated. Statistical analysis performed with a Student's t-test. (FIGS. 6C-D) Graphs showing the number of adherent neutrophils and the platelet volumes in cremaster venule thrombi in HIT mice 60 minutes after laser injury. Individual data points and mean±1 SD are shown. 6 injuries were made in 3 TRA-treated HIT mice, 42 injuries were made in 10 KKO-treated Padi4$^{-/-}$ HIT mice, 5 injuries were made in 1 TRA-treated Padi4$^{-/-}$ mouse, 24 injuries were made in 13 KKO-treated HIT mice, and 37 injuries were made in 6 KKO-treated HIT mice following infusion of DNase. Comparative statistical analysis was performed with a Kruskall-Wallis one-way ANOVA. (FIG. 6E) Representative confocal images demonstrating the extent of platelet and neutrophil accumulation at the site of cremaster venule thrombi following HIT-induction, 5 and 60 minutes after the inciting laser injury and infusion of KKO in Padi4$^{-/-}$ mice compared to Padi4$^{+/+}$ mice±DNase. Size bar and arrow indicating direction of flow are included. Same microscope and acquisition software as in FIG. 1D.

FIGS. 7A-7B. Myeloperoxidase (MPO) and cell-free DNA (cfDNA levels in clinical samples. Measurements of (FIG. 7A) cfDNA levels and (FIG. 7B) MPO-DNA complex levels from normal controls (Ctl), patients diagnosed with ITP, and patients evaluated for HIT that either had a confirmed diagnosis ("HIT") or were unlikely to have HIT ("Non-HIT"). Individual measurements and mean±1 SD are shown. Comparative statistical analysis was performed by Kruskall-Wallis one-way ANOVA.

FIGS. 8A-8F. Effects of PF4 infusion on circulating NDP levels following LPS exposure in WT and cxcl4$^{-/-}$ mice. WT and cxcl4$^{-/-}$ mice received LPS (35 mg/kg, IP) and plasma samples were obtained at the indicated time points. (FIG. 8A) Mean plasma cfDNA levels are shown as ±1 standard deviation (SD). N=7-14 mice per arm. P values are indicated comparing WT and cxcl4$^{-/-}$ mice using a Mann-Whiney U test. (FIG. 8B) is the same as FIG. 8A, but for MPO levels at 3 to 8 hours post-LPS. (FIG. 8C) Histone levels comparing western blot intensity to that of the positive control band. N=9-10 mice per arm. P values are indicated comparing WT and cxcl4$^{-/-}$ mice by Mann-Whiney U test. (FIG. 8D) LPS studies comparing WT and cxcl4$^{-/-}$ mice following implantation of osmotic pumps containing PBS alone or 80 μg of hPF4. Mean±1 SD are shown N=5-8 mice per arm. (FIG. 8E) Same as FIG. 8D but following a single dose of hPF4 (80 μg, IV). N=5-8 mice per arm. (FIG. 8F) LPS studies comparing plasma levels of cfDNA-MPO complex in cxcl4$^{-/-}$ mice that received tail vein injections containing PBS along or 80 μg of PF4. N=4-5 mice per arm. P values are indicated comparing WT and cxcl4$^{-/-}$ mice by Mann-Whiney U test.

FIGS. 9A-9B. Effect of PF4 on endothelial cells and microbial entrapment by NETs in vitro. Channels lined with TNFα-stimulated HUVECs were infused with isolated human neutrophils treated with TNFα (1 ng/ml) with and without hPF4 (25 μg/ml). (FIG. 9A) Channels were incubated with the neutrophils for 16 hours after which the number of residual adherent endothelial cells was counted. At the top, representative images of remaining attached endothelial cells channels per condition. Size-bar and arrows indicating direction of flow are included. At the bottom, mean of endothelial cell counts in three 10× high-powered fields (HPFs) per condition±1 SD. Statistical analysis was performed using a Student's test. (FIG. 9B) Left shows representative images of NET-lined channels infused with fluorescently-labeled *S. aureus* with observed bacterial capture. Size-bar and arrows indicating direction of flow are included. Right shows mean±1 SD quantified of the mean fluorescent intensity (MFI). For both left and right, top are studies without added DNase I and bottom in the presence of DNase I (100 U/ml). N=5-10 channels per condition. Analysis performed by a Kruskal-Wallis one-way ANOVA.

FIGS. 10A-10G. Binding of DG-KKO to PF4/NET complexes in vitro. (FIG. 10A) Graphs quantifying binding of increasing concentrations of KKO (gray) and DG-KKO (red) to heparin using fluorescent plate assay. (FIG. 10B) Same as FIG. 10A but using flow cytometry to quantify antibody binding to the platelet surface. (FIG. 10C) Mean±1 SD of P-selectin MFI in human whole blood samples incubated with the indicated concentration of antibody, reflecting the degree of platelet activation. N=3. (FIG. 10D) Mean±1 SD of the % decrease in platelets counts in HIT mice injected with 400 μg of the indicated antibody, measured every 12 hours for 3 days. N=10. (FIG. 10E) Representative confocal images of released NETs as in FIGS. 2A-C exposed to no PF4 or 6.5 μg/ml of PF4, labeled with the nucleic acid stain Sytox green (green) demonstrating change in morphology. The indicated channels were then infused with fluorophore-labeled DG-KKO (white). Size-bar and arrows indicating direction of flow are included. Image were obtained at 10× magnification. (FIG. 10F) Representative widefield images of adherent neutrophils as in FIG. 10A, but in the presence of 100 U/ml DNase I and 6.5 μg/ml PF4±25 μg/ml of DG-KKO. (FIG. 10G) Mean±1 SD of the relative area of NETs compacted with PF4 (6.5 μg/ml) alone or PF4 plus either DG-KKO or a polyclonal anti-PF4 antibody control (Ctl) (each, 25 μg/ml KKO) post an infusion of DNase I (100 U/ml, 3 minutes) compared to pre-infusion. N=7-10 channels per condition. Comparative statistical analysis performed by Kruskall-Wallis one-way ANOVA.

FIGS. 11A-11F. DG-KKO treatment in WT, cxcl4$^{-/-}$ and hPF4$^{+}$ mice undergoing LPS endotoxemia. Mice were injection with LPS (35 mg/kg, IP). 30 minutes later they received tail vein injections containing vehicle alone or 5 mg/kg of DG-KKO or DG-TRA isotype control. Six hours following LPS injection, a subset of mice were euthanized and IVC blood samples were collected. N=3-10 in each arm. (FIG. 11A) Relative to baseline (dashed gray line), 6 hour-time point platelet counts. Mean±1 SD shown. ND=not done. Comparative statistical analysis was performed with Sidak's multiple comparison test. (FIGS. 11B-E) Same as FIG. 11A, but for cfDNA concentration, cfDNA-MPO-fold change relative to negative control, MCP1 levels, and MSS, respectively. (FIG. 11F) are animal survival results for these LPS studies in the hPF4$^{+}$ mice. Results were analyzed with Kaplan Meier survival analysis. See FIG. 9 for survival results after DG-KKO in the WT and cxcl4$^{-/-}$ mice undergoing LPS endotoxemia.

FIGS. 12A-12D. DG-KKO treatment in cxcl4$^{-/-}$ and hPF4$^{+}$ mice undergoing CLP injury. All the mice underwent CLP procedure. Some mice, 1 hour following surgery, received an intradermal dose of the antibiotic ceftriaxone (100 mg/kg). Mice also were divided by therapeutic intervention, receiving either vehicle only or 5 mg/kg of KKO or DG-KKO or TRA or DG-TRA. After 48 hours, platelet counts and plasma NDP levels and survival were quantified. N=10 animals per arm. Statistical analysis performed with Sidak's multiple comparison t-test. (FIG. 12A) Relative platelet counts 6-hours post-CLP injury measured as in FIG. 11A. (FIGS. 12B-C) Same as FIG. 11B and FIG. 11C, respectively, but after a CLP injury. (FIG. 12D) Animal survival results for these CLP studies. Statistical analysis performed with Kaplan Meier survival analysis.

FIGS. 13A-13D. Treatment with PF4 or PF4 plus KKO or DG-KKO in WT mice undergoing CLP injury. CLP injuries were done as in FIGS. 5A-E, but with WT mice that either received vehicle, PF4 at either 20 or 40 mg/kg, or combination therapy of PF4 (20 mg/kg) plus either 5 mg/kg KKO or DG-KKO. N=10 animals per arm. (FIG. 13A) Relative platelet counts as in FIG. 12A. FIG. 13B-C are as in FIGS. 12B and 12C, respectively. (FIG. 13D) MSS in studies for up to 48 hrs after the injury. Mean±1 SD shown. In FIGS. 13A-D, statistical analysis was performed with Sidak's multiple comparison t-test.

Figure 14:
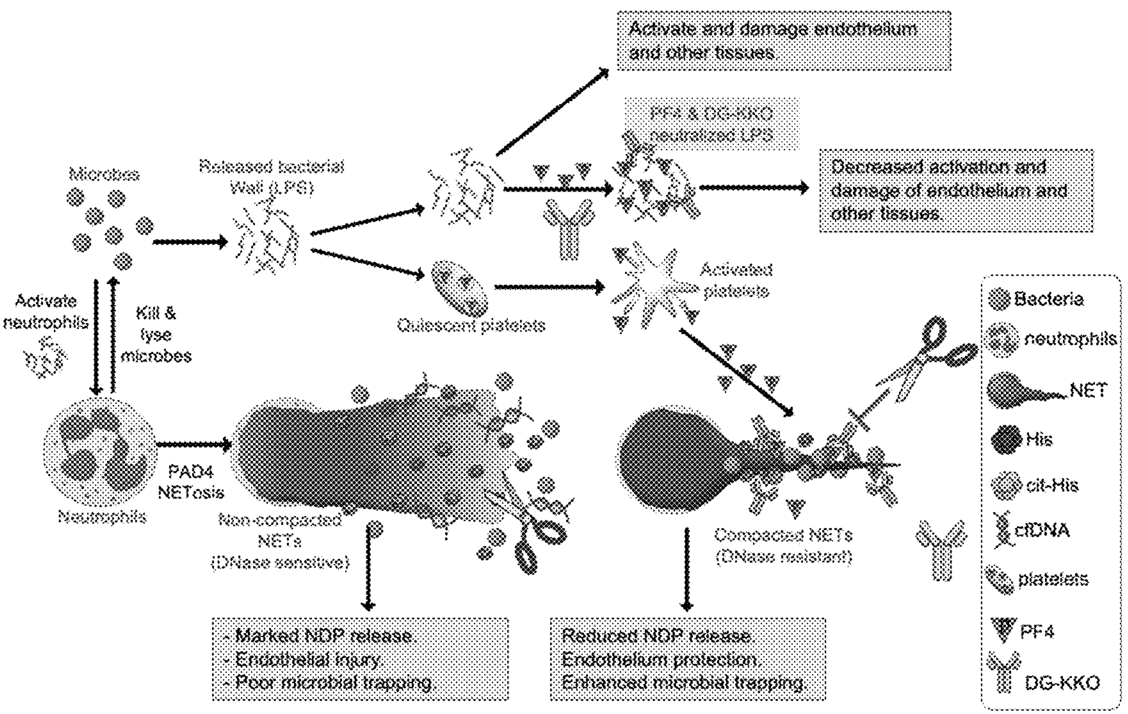
FIG. 14. Schematic of DG-KKO therapy in sepsis. Interactions between microbes, neutrophils and platelets with the effects of released PF4 and DG-KKO or any other antibody that can crossaggregate NETs and neutralize LPS are shown.

The three effects are 1) neutralizing LPS, 2) stabilizing NETs, and 3) enhancing microbial entrapment and localizing the toxic materials released from them within Nets.

FIGS. 15A-C. CRISPR/Cas9 gene-editing generation of Padi4$^{-/-}$ mice. (FIG. 15A) A schematic showing the first three exons of the murine Padi4 gene and the binding of CRISPR gRNAs designed to disrupt a 0.2 kb region (red) of the Padi4 gene encompassing Exon 2. The sequence shown is SEQ ID NO: 5. (FIG. 15B) Electrophoresis gels demonstrating the disruption of Exon 2 PCR amplification in 4 clones, and below the gels is the DNA sequence analysis from a wild-type mouse with the portion of Exon 2 deleted in clone 18 represented in grey, lower-case letters. At the bottom is the normal murine PAD4 amino acid (aa) sequence in red with caps indicating sequence preserved in Clone 18, and small letters indicating the aa sequence lost in Clone 18 (SEQ ID NO: 6). The truncated PAD4 sequence expected in clone 18 is shown below with the preserved first 8 aa in red, followed by a frameshift mutation (-) leading to 9 altered aa in blue with a premature stop codon indicated by an * (SEQ ID NO: 7). (FIG. 15C) Representative images of bone marrow-isolated neutrophils obtained from clone 18 Padi4$^{-/-}$ mice and Padi4$^{+/+}$ siblings, plated on a poly-L-lysine coated slide, incubated with buffer alone or PMA (100 nM) overnight. Samples were stained with SYTOX green to visualize DNA shown in green, and anti-histone H3 (citrulline R2+R8+R17) to visualize citrullinated histones (cit-His) shown in red. SYTOX and cit-His staining of unstimulated cells shows intact nuclei with cit-His staining only observed in Padi4$^{+/+}$ cells. Staining of PMA stimulated cells shows extracellular DNA strands and increased cit-H3 in Padi4$^{+/+}$ cells. The microscope and acquisition software were as described in FIG. TA.

FIGS. 16A-B. TNFα stimulation does not enhance KKO binding to human umbilical vein endothelial cells (HUVECs). (FIG. 16A) Graph showing the mean±1 SD of KKO adhesion to microfluidic channels coated with a confluent layer of HUVECs after infusion of whole blood or physiological buffered saline (PBS) containing PF4 (25 μg/ml) and ALEXA FLUOR™ 488-conjugated KKO. Two fluorescent measurements were obtained from each channel. The number of channels per arm is indicated on the graph. The channels were either unstimulated, treated with TNFα prior to infusion, or subjected to photochemical hematoporphyrin injury. When whole blood was flowed through TNFα-treated channels, the channels clotted, leading to interference with fluorescence measurements. Therefore, the inventors only infused these channels with PBS. Comparative statistical analysis was done with a with a Kruskal-Wallis one-way ANOVA. (FIG. 16B) Representative confocal images of an unstimulated channel infused with PBS, an uninjured channel infused with whole blood, a TNFα-stimulated channel infused with PBS, and a whole blood infused channel subjected to photochemical injury on the right half of the presented field. In this image, KKO only adheres to the injured portion of the channel to the right of the gray dotted line. Scale bar and arrows showing direction of flow are indicated.

FIGS. 17A-B. Fibrin generation occurs in in cremaster laser injuries. (FIG. 17A) Cremaster venule thrombus at 5 minutes after injury, but prior to KKO exposure in HIT mice. Scale bar and arrows showing direction of flow are indicated. Fibrin and platelet accumulation are shown alone at the right. A composite image including the neutrophil stain is shown on left. (FIG. 17B) Same injury 60 minutes following KKO administration.

FIG. 18. cfDNA released from neutrophils adherent to HUVECs in a microfluidic chamber. Representative fields of released cfDNA from LPS-stimulated neutrophils in a HUVEC lined microfluidic channel demonstrating the compaction and aggregation of the cfDNA by the addition of hPF4 (25 μg/ml). Arrow indicates direction of flow. Size bar included as well. Images obtained with a ZEISS™ LSM 710 confocal microscope. Original magnification was 20×.

FIG. 19. Entrapment of *S aureus* bacteria on DG-KKO/PF4-NET complexes in a microfluidic well. Representative confocal image of SYTOX orange-stained NETs compacted with PF4 (100 μg/ml) and bound by 647-labeled DG-KKO, infused with 488-labeled S *Aureus* bioparticles (40 μg/ml), showing direct adhesion of *S aureus* bioparticle to DG-KKO complexed to PF4-NETs. Images obtained with a ZEISS™ LSM 710 confocal microscope. Original magnification 40×. Scale bar and arrow showing direction of flow are indicated.

FIGS. 20A-C. MS/HPLC analysis confirms the deglycosylation of KKO. (FIG. 20A) Schematic describing DG-KKO generation by incubation with endoglycosidase S and preparation for analysis with mass spectroscopy with treatment with trypsin and PNGase F (on left) compared to control KKO. (FIG. 20B) Analysis of peptide fragments generated following antibody incubation with endoS showing a large peak at 37 minutes representing 93% of the sample corresponding to a fucosylated peptide generated following digestion of DG-KKO, and a small peak at 42 minutes representing the deiminated peptide generated from KKO. (FIG. 20C) Analysis of peptide fragments generation from digestion of KKO, showing no peak at 37 minutes, but a large peak at 42 minutes corresponding to the deiminated peptide. (FIG. 20D) Amino acid sequences of peptides generated from the digestion of KKO and DG-KKO. The top two sequences cumulatively represent 3% of the sample. The fucosylated peptide (3$^{rd}$ from the top) was 93% of the peptides obtained from digestion of DG-KKO. The deiminated peptide (4$^{th}$ from the top) represented ~6% of the peptides generated from DG-KKO and 100% of the peptides generated from KKO.

FIG. 21. TAT levels in DG-KKO-treated LPS-exposed mice. Mice were injected with LPS (35 mg/kg, IP). 30 minutes later they received tail vein injections containing vehicle alone or 5 mg/kg DG-KKO. 6 hours following LPS injection, mice were euthanized and IVC blood samples were collected and plasma was isolated. ELISA was used to quantify TAT complexes concentrations in the plasma samples. N=3-9 animals per arm. n.s.=no significant difference. Statistical analysis was performed with a Kruskal-Wallis one-way ANOVA.

FIGS. 22A-D. DG-KKO effects on platelet count, NDP release and survival in LPS±DNase I-exposed hPF4$^{+}$ mice. Mice received LPS (35 mg/kg body weight, IP) and DNase I (20 mg/kg, IP). Mean±1 SD of (FIG. 22A) platelet counts, (FIG. 22B) cfDNA, (FIG. 22C) MPO-cfDNA, and (FIG. 22D) MSS were measured at 6 hours post-exposure. N=10 animals per arm. Analysis performed with Sidak's multiple comparison t-test.

DESCRIPTION OF ILLUSTRATIVE EMBODIMENTS

The inventors' studies of the role of PF4 in HIT lead to the unique observation that PF4 physically compacts NETs and protects them from deoxyribonuclease 1 (DNase I) digestion without displacing histones bound to the NETs. Moreover, unlike a polyclonal anti-PF4 antibody, a monoclonal HIT-like antibody KKO further stabilized PF4-bound NETs and lead to additional resistance to DNase I, decreased release of NET degradation products (NDPs), like histones, a marked enhancement in microbial entrapment and neutralizing LPS released from bacterial walls. These observations lead to the inventors' unique proposal that such stabilization of NETs, prevention of NDP-release, enhanced microbial entrapment and LPS neutralization may be protective in sepsis where such products target and injure multiple organs.

The Inventors have gone on to show that PF4 and an FC-modified deglycosated form of KKO (DG-KKO) can in vitro protect NETs from DNase lysis, and markedly enhances trapping of microbes and have demonstrated such for *Staphylococcus aureus* and now *Escherichia coli*. They show that each alone and together could markedly improve outcome in murine models of sepsis including an LPS endotoxemia model and a cecum ligation and puncture (CLP) polymicrobial model but only in mice that express human (h) PF4. They go on to show that unmodified KKO is of no benefit and appears to accelerate death in hPF4 mice undergoing the CLP model, further supporting the proposed mechanism of how PF4 and/or DG-KKO infusions effect sepsis as a unique therapeutic intervention.

I. Neutrophils

Neutrophils are the most abundant type of leukocytes and the most abundant (40% to 70%) type of white blood cells in most mammals. They form an essential part of the innate immune system. Their functions vary in different animals. They are formed from stem cells in the bone marrow. They are short-lived and highly motile as they can enter parts of tissue where other cells/molecules cannot. Neutrophils include mature, segmented neutrophils and more immature banded neutrophils (or bands). They form part of the polymorphonuclear cells family (PMNs) together with basophils and eosinophils.

The name "neutrophil" derives from staining characteristics on hematoxylin and eosin (H&E) histological or cytological preparations. Whereas basophilic white blood cells stain dark blue and eosinophilic white blood cells stain bright red, neutrophils stain a neutral pink. Normally, neutrophils contain a nucleus divided into 2-5 lobes.

Neutrophils are a type of phagocyte and are normally found in the bloodstream and tissues. During the beginning (acute) phase of inflammation, particularly as a result of bacterial infection, environmental exposure, and some cancers, neutrophils are one of the first-responders of inflammatory cells to migrate towards the site of inflammation. They migrate through the blood vessels, then through interstitial tissue, following chemical signals such as Interleukin-8 (IL-8), C5a, fMLP, Leukotriene B4 and $H_2O_2$ in a process called chemotaxis. They are the predominant cells in pus, accounting for its whitish/yellowish appearance.

Neutrophils are recruited to the site of injury within minutes following trauma and are the hallmark of acute inflammation; however, due to some pathogens being indigestible, they can be unable to resolve certain infections without the assistance of other types of immune cells.

When adhered to and spread on a surface, neutrophil granulocytes have an average diameter of 12-15 micrometers (μm) in peripheral blood smears. In suspension, human neutrophils have an average diameter of 8.85 μm.

With the eosinophil and the basophil, neutrophils form the class of polymorphonuclear cells, named for the nucleus' multilobulated shape (as compared to lymphocytes and monocytes, the other types of white cells). The nucleus has a characteristic lobed appearance, the separate lobes connected by chromatin. The nucleolus disappears as the neutrophil matures, which is something that happens in only a few other types of nucleated cells. In the cytoplasm, the Golgi apparatus is small, mitochondria and ribosomes are sparse, and the rough endoplasmic reticulum is absent. The cytoplasm also contains about 200 granules, of which a third are azurophilic. Neutrophils are sexually dimorphic. Neutrophils from women exhibit a small additional X chromosome structure, known as a "neutrophil drumstick."

Neutrophils will show increasing segmentation (many segments of the nucleus) as they mature. A normal neutrophil should have 3-5 segments. Hypersegmentation is not normal but occurs in some disorders, most notably vitamin B12 deficiency. This is noted in a manual review of the blood smear and is positive when most or all of the neutrophils have 5 or more segments.

Neutrophils are the most abundant white blood cells in humans (approximately $10^{11}$ are produced daily); they account for approximately 50-70% of all white blood cells (leukocytes). The stated normal range for human blood counts varies between laboratories, but a neutrophil count of $2.5\text{-}7.5\times10^9$/L is a standard normal range. People of African and Middle Eastern descent may have lower counts, which are still normal. A report may divide neutrophils into segmented neutrophils and bands. When circulating in the bloodstream and inactivated, neutrophils are spherical. Once activated, they change shape and become more amorphous or amoeba-like and can extend pseudopods as they hunt for antigens.

The average lifespan of inactivated human neutrophils in the circulation has been reported by different approaches to be between 5 and 90 hours. Upon activation, they marginate (adhere to the blood vessel endothelium) and undergo selectin-dependent capture followed by integrin-dependent adhesion in most cases, after which they migrate into tissues, where they survive for 1-2 days.

Neutrophils are much more numerous than the longer-lived monocyte/macrophage phagocytes. A pathogen (disease-causing microorganism or virus) is likely to first encounter a neutrophil. Some experts hypothesize that the short lifetime of neutrophils is an evolutionary adaptation. The short lifetime of neutrophils minimizes propagation of those pathogens that parasitize phagocytes because the more time such parasites spend outside a host cell, the more likely they will be destroyed by some component of the body's defenses. Also, because neutrophil antimicrobial products can also damage host tissues, their short life limits damage to the host during inflammation. Neutrophils will be removed after phagocytosis of pathogens by macrophages. PECAM-1 and phosphatidylserine on the cell surface are involved in this process.

Neutrophils undergo a process called chemotaxis via amoeboid movement, which allows them to migrate toward sites of infection or inflammation. Cell surface receptors allow neutrophils to detect chemical gradients of molecules such as interleukin-8 (IL-8), interferon gamma (IFN-γ), C3a, C5a, and Leukotriene B4, which these cells use to direct the path of their migration.

Neutrophils have a variety of specific receptors, including ones for complement, cytokines like interleukins and IFN-γ, chemokines, lectins, and other proteins. They also express receptors to detect and adhere to endothelium and Fc receptors for opsonin.

In leukocytes responding to a chemoattractant, the cellular polarity is regulated by activities of small Rho guanosine triphosphatases (Rho GTPases) and the phosphoinositide 3-kinases (PI3Ks). In neutrophils, lipid products of PI3Ks regulate activation of Rho GTPases and are required for cell motility. They accumulate asymmetrically to the plasma membrane at the leading edge of polarized cells. Spatially regulating Rho GTPases and organizing the leading edge of the cell, PI3Ks and their lipid products could play pivotal roles in establishing leukocyte polarity, as compass molecules that tell the cell where to crawl.

It has been shown in mice that in certain conditions neutrophils have a specific type of migration behavior referred to as neutrophil swarming during which they migrate in a highly coordinated manner and accumulate and cluster to sites of inflammation.

Being highly motile, neutrophils quickly congregate at a focus of infection, attracted by cytokines expressed by activated endothelium, mast cells, and macrophages. Neutrophils express and release cytokines, which in turn amplify inflammatory reactions by several other cell types.

In addition to recruiting and activating other cells of the immune system, neutrophils play a key role in the front-line defense against invading pathogens. Neutrophils have three methods for directly attacking micro-organisms: phagocytosis (ingestion), degranulation (release of soluble anti-microbials), and generation of NETs, as discussed further below.

Neutrophils are phagocytes, capable of ingesting micro-organisms or particles. For targets to be recognized, they must be coated in opsonins—a process known as antibody opsonization. They can internalize and kill many microbes, each phagocytic event resulting in the formation of a phagosome into which reactive oxygen species and hydrolytic enzymes are secreted. The consumption of oxygen during the generation of reactive oxygen species has been termed the "respiratory burst," although unrelated to respiration or energy production.

The respiratory burst involves the activation of the enzyme NADPH oxidase, which produces large quantities of superoxide, a reactive oxygen species. Superoxide decays spontaneously or is broken down via enzymes known as superoxide dismutases (Cu/ZnSOD and MnSOD), to hydrogen peroxide, which is then converted to hypochlorous acid (HClO), by the green heme enzyme myeloperoxidase. It is thought that the bactericidal properties of HClO are enough to kill bacteria phagocytosed by the neutrophil, but this may instead be a step necessary for the activation of proteases.

Neutrophils also release an assortment of proteins in three types of granules by a process called degranulation. The contents of these granules have antimicrobial properties, and help combat infection:

| Granule type | Protein |
|---|---|
| Azurophilic granules (or "primary granules") | Myeloperoxidase (MPO), bactericidal/permeability-increasing protein (BPI), defensins, and the serine proteases neutrophil elastase (NE) and cathepsin G |
| Specific granules (or "secondary granules") | Alkaline phosphatase, lysozyme, NADPH oxidase, collagenase, lactoferrin, histaminase, and cathelicidin |
| Tertiary granules | Cathepsin, gelatinase and collagenase |

Low neutrophil counts are termed neutropenia. This can be congenital (developed at or before birth) or it can develop later, as in the case of aplastic anemia or some kinds of leukemia. It can also be a side-effect of medication, most prominently chemotherapy. Neutropenia makes an individual highly susceptible to infections. It can also be the result of colonization by intracellular neutrophilic parasites.

The absolute neutrophil count (ANC) is also used in diagnosis and prognosis. ANC is the gold standard for determining severity of neutropenia, and thus neutropenic fever. Any ANC <1500 cells/mm$^3$ is considered neutropenia, but <500 cells/mm$^3$ is considered severe. There is also new research tying ANC to myocardial infarction as an aid in early diagnosis.

II. Nets, Netosis and PF4

A. NETS

NETs are networks of extracellular chromatin fibers, primarily composed of the histone-bound DNA from neutrophils. NETs were first recognized to bind and entrap microbes. As noted above, neutrophils are the immune system's first-line of defense against infection and have conventionally been thought to kill invading pathogens through two strategies: engulfment of microbes and secretion of anti-microbials. In 2004, a novel third function was identified—formation of NETs. NETs allow neutrophils to kill extracellular pathogens while minimizing damage to the host cells. Upon in vitro activation with the pharmacological agent phorbol myristate acetate (PMA), IL-8 or lipopolysaccharide (LPS). In both HIT and sepsis, inflammation-activated neutrophils release NETs.

High-resolution scanning electron microscopy has shown that NETs consist of stretches of DNA and globular protein domains including histones and a modified version, citrullinated histones. These form fibrils with diameters of 15-25 nm. These aggregate into larger threads with a diameter of 50 nm in part presumably by binding PF4. Under flow conditions, NETs can form much larger structures, reaching hundreds of nanometers in length and width.

Analysis by immunofluorescence corroborated that NETs contain proteins from azurophilic granules (NE, cathepsin G and MPO), specific granules (lactoferrin), tertiary granules (gelatinase), and the cytoplasm.

NETs disarm pathogens with antimicrobial proteins via NE, cathepsin G and histones that have a high affinity for DNA. NETs provide for a high local concentration of antimicrobial components and bind, disarm, and kill microbes extracellularly independent of phagocytic uptake. In addition to their antimicrobial properties, NETs may serve as a physical barrier that prevents further spread of the pathogens. Furthermore, delivering the granule proteins into NETs may keep potentially injurious proteins like proteases from diffusing away and inducing damage in tissue adjacent to the site of inflammation.

More recently, it has also been shown that not only bacteria but also pathogenic fungi such as *Candida albicans* induce neutrophils to form NETs that capture and kill *C. albicans* hyphal as well as yeast-form cells. NETs have also been documented in association with *Plasmodium falciparum*: infections in children.

While it was originally proposed that NETs would be formed in tissues at a site of bacterial/yeast infection, NETs have also been shown to form within blood vessels during sepsis (especially in the lung capillaries and liver sinusoids). Intra-vascular NET formation is tightly controlled and is regulated by platelets, which sense severe infection via platelet TLR4 and then become activated, undergoing important changes, including releasing large amounts of PF4 from their alpha-granules. Platelets, likely via several mechanisms, bind to and activate neutrophils, contributing to NET formation. Platelet-induced NET formation occurs very rapidly (in minutes) and may not result in death of the neutrophils. NETs formed in blood vessels can catch circulating bacteria as they pass through the vessels. Trapping of bacteria under flow has been imaged directly in flow chambers in vitro and intravital microscopy demonstrated that bacterial trapping occurs in the liver sinusoids and lung capillaries (sites where platelets are bound to neutrophils, releasing PF4).

B. NETosis

NET activation and release, or NETosis, is a dynamic process that can come in two forms, suicidal and vital NETosis. Overall, many of the key components of the process are similar for both types of NETosis, however, there are key differences in stimuli, timing, and ultimate end result. The full NETosis activation pathway is still under investigation but a few key proteins have been identified and slowly a full picture of the pathway is emerging. The process is thought to begin with NADPH oxidase activation of PAD4 via reactive-oxygen species (ROS) intermediaries. PAD4 is responsible for the citrullination of histones in the neutrophil, resulting in decondensation of chromatin by chemically modifying histones so that they do not bind DNA as tightly, a process termed citrullination. Azurophilic granule proteins such as MPO and NE then enter the nucleus and further the decondensation process, resulting in the rupture of the nuclear envelope. The uncondensed chromatin enter the cytoplasm where additional granule and cytoplasmic proteins are added to the early-stage NET. The end result of the process then depends on which NETosis pathway is activated.

Suicidal NETosis. Suicidal NETosis was first described in a 2007 study that noted that the release of NETs resulted in neutrophil-death through a different pathway than apoptosis or necrosis. In suicidal NETosis, the intracellular NET formation is followed by the rupture of the plasma membrane, releasing it into the extracellular space. This NETosis pathway can be initiated through activation of Toll-like Receptors (TLRs), Fc receptors, and complement receptors with various ligands such as antibodies, PMA, and so on. The current understanding is that upon activation of these receptors, downstream signaling results in the release of calcium from the endoplasmic reticulum. This intracellular influx of calcium in turn activates NADPH oxidase, resulting in activation of the NETosis pathway as described above. Of note, suicidal NETosis can take hours, even with high levels of PMA stimulation, while vital NETosis that can be completed in a matter of minutes.

Vital NETosis. Vital NETosis can be stimulated by bacterial LPS, other "bacterial products, TLR4-activated platelets, or complement proteins in tandem with TLR2 ligands." Vital NETosis is made possible through the blebbing of the nucleus, resulting in a DNA-filled vesicle that is exocytosed and leaves the plasma membrane intact. Its rapid formation and release do not result in neutrophil death, however, the cell is without DNA, raising questions about whether a cell without DNA can be considered alive. It has been noted that neutrophils can continue to phagocytose and kill microbes after vital NETosis, highlighting the neutrophil's anti-microbial versatility.

Regulation. The formation of NETs is regulated by the lipoxygenase pathway—during certain forms of activation (including contact with bacteria) neutrophil 5-lipoxygenase forms 5-HETE-phospholipids that inhibit NET formation. Evidence from laboratory experiments suggests that NETs are cleaned away by macrophages that phagocytose and degrade them.

NET-associated host damage. NETs can also have a deleterious effect on the host, because the exposure of extracellular histone complexes and other NDPs. NETs could also play a role in inflammatory diseases, as NETs could be identified in preeclampsia, a pregnancy related inflammatory disorder in which neutrophils are known to be activated. NETs have also been reported in the colon mucosa of patients with the inflammatory bowel disease ulcerative colitis. NETs have also been associated with the production of IgG antinuclear double stranded DNA antibodies in children infected with *P. falciparum* malaria. As mentioned above, NETs also have a role in thrombosis. Important to this application, an overwhelming wave of NET release and their subsequent lysis by circulating DNases from the host and bacteria contribute to morbidity and mortality in sepsis. Animal models have shown that histones for example cause a similar toxic model in mice as the injection of LPS. These observations suggest that NETs might play an important role in the pathogenesis of infectious, inflammatory and thrombotic disorders and sepsis. Approaches to ameliorate the effect of NETs in sepsis may have therapeutic benefits. Such approaches include preventing the release of NETs by targeting PAD4 or enhancing NET lyses by infusion of DNases, but such strategies have meet with mixed results in experimental models likely because in these models, these is already massive NET formation so blocking PAD4 is likely going to be too late in patients presenting with sepsis and that lysing the NETs would overwhelm the recipient with NDPs. The inventors propose a new approach to prevent NETs from contributing to sepsis in HIT and that is to stabilize the released NETs and prevent the release of noxious NDPs from them into the patient.

III. Net Related Diseases/Syndromes

A. Sepsis

Sepsis is a life-threatening condition of organ dysfunction that arises when the body has a dysfunctional response to an infection causing injury to its own tissues and organs. Common signs and symptoms include fever, increased heart rate, increased breathing rate, and confusion. There also may be symptoms related to a specific infection, such as a cough with pneumonia, or painful urination with a kidney infection. In the very young, old, and people with a weakened immune system, there may be no symptoms of a specific infection and the body temperature may be low or normal, rather than high. Severe sepsis is sepsis causing poor organ function or insufficient blood flow. Insufficient blood flow may be evident by low blood pressure, high blood lactate, or low urine output. Septic shock is low blood pressure due to sepsis that does not improve after reasonable amounts of intravenous fluids are given.

Sepsis is caused by an immune response triggered by an infection. Most commonly, the infection is bacterial, but it may also be from fungi, viruses, or parasites. Common locations for the primary infection include lungs, brain, urinary tract, skin, and abdominal organs. Risk factors include extremely young or old, a weakened immune system from conditions such as cancer or diabetes, major trauma, or burns. An older method of diagnosis was based on meeting at least two systemic inflammatory response syndrome (SIRS) criteria due to a presumed infection. In 2016, SIRS was replaced with qSOFA which is two of the following three: increased breathing rate, change in level of consciousness, and low blood pressure. Blood cultures are recommended preferably before antibiotics are started, however, infection of the blood is not required for the diagnosis.

Medical imaging should be used to look for the possible location of infection. Other potential causes of similar signs and symptoms include anaphylaxis, adrenal insufficiency, low blood volume, heart failure, and pulmonary embolism, among others.

Sepsis is usually treated with intravenous fluids and antibiotics. Typically, antibiotics are given as soon as possible. Often, ongoing care is performed in an intensive care unit. If fluid replacement is not enough to maintain blood pressure, medications that raise blood pressure may be used. Mechanical ventilation and dialysis may be needed to support the function of the lungs and kidneys, respectively. To guide treatment, a central venous catheter and an arterial catheter may be placed for access to the bloodstream. Other measurements such as cardiac output and superior vena cava oxygen saturation may be used. People with sepsis need preventive measures for deep vein thrombosis, stress ulcers and pressure ulcers, unless other conditions prevent such interventions. Some might benefit from tight control of blood sugar levels with insulin. The use of corticosteroids is controversial. Activated drotrecogin alfa, originally marketed for severe sepsis, has not been found to be helpful, and was withdrawn from sale in 2011.

Disease severity partly determines the outcome. The risk of death from sepsis is as high as 30%, from severe sepsis as high as 50%, and from septic shock as high as 80%. The number of cases worldwide is unknown as there is little data from the developing world. Estimates suggest sepsis affects millions of people a year. In the developed world approximately 0.2 to 3 people per 1000 are affected by sepsis yearly, resulting in about a million cases per year in the United States. Rates of disease have been increasing. Sepsis is more common among males than females. The medical condition has been described since the time of Hippocrates. The terms septicemia and blood poisoning refer to the microorganisms or their toxins in the blood and are no longer commonly used.

In addition to symptoms related to the provoking cause, sepsis is frequently associated with either fever, low body temperature, rapid breathing, elevated heart rate, confusion, and edema. Early signs are a rapid heart rate, decreased urination, and high blood sugar. Signs of established sepsis include confusion, metabolic acidosis (which may be accompanied by faster breathing and lead to a respiratory alkalosis), low blood pressure due to decreased systemic vascular resistance, higher cardiac output, and dysfunctions of blood coagulation (where clotting may lead to organ failure).

The drop in blood pressure seen in sepsis may lead to shock. This may result in light-headedness. Bruising or intense bleeding may occur.

The most common primary sources of infection resulting in sepsis are the lungs, the abdomen, and the urinary tract. Typically, 50% of all sepsis cases start as an infection in the lungs. No definitive source is found in one third to one half of cases.

Infections leading to sepsis usually are bacterial but may be fungal or viral. Gram-positive bacteria were the predominant cause of sepsis before the introduction of antibiotics in the 1950s. After the introduction of antibiotics, gram-negative bacteria became the predominant cause of sepsis from the 1960s to the 1980s. After the 1980s, gram-positive bacteria, most commonly staphylococci, are thought to cause more than 50% of cases of sepsis. Other commonly implicated bacteria include *Staphylococcus* (S) *aureus, Escherichia* (E) *coli, Pseudomonas aeruginosa*, and *Klebsiella* species. Fungal sepsis accounts for approximately 5% of severe sepsis and septic shock cases; the most common cause of fungal sepsis is infection by *Candida* species of yeast, a nosocomial infection frequently acquired in hospitals.

Early recognition and focused management may improve the outcomes in sepsis. Current professional recommendations include a number of actions ("bundles") to be followed as soon as possible after diagnosis. Within the first three hours someone with sepsis should have received antibiotics and, intravenous fluids if there is evidence of either low blood pressure or other evidence for inadequate blood supply to organs (as evidenced by a raised level of lactate); blood cultures also should be obtained within this time period. After six hours the blood pressure should be adequate, close monitoring of blood pressure and blood supply to organs should be in place, and the lactate should be measured again if initially, it was raised. A related bundle, the "Sepsis Six", is in widespread use in the United Kingdom; this requires the administration of antibiotics within an hour of recognition, blood cultures, lactate and hemoglobin determination, urine output monitoring, high-flow oxygen, and intravenous fluids.

Apart from the timely administration of fluids and antibiotics, the management of sepsis also involves surgical drainage of infected fluid collections and appropriate support for organ dysfunction. This may include hemodialysis in kidney failure, mechanical ventilation in lung dysfunction, transfusion of blood products, and drug and fluid therapy for circulatory failure. Ensuring adequate nutrition—preferably by enteral feeding, but if necessary, by parenteral nutrition—is important during prolonged illness. Medication to prevent deep vein thrombosis and gastric ulcers also may be used.

B. Vasculitides

Vasculitides are a heterogeneous group of autoimmune diseases, all characterized by inflammation of blood vessels (vasculitis) and subsequent ischemia and damage to the organs supplied by these vessels. Vasculitis may occur as a primary disease (idiopathic) or as a secondary response to an underlying disease (e.g., hepatitis B infection). While the inflammatory process may be confined to one organ, it may also involve several organ systems. Vasculitis should be considered in patients presenting with palpable purpura, pulmonary infiltrates, unexplained ischemic events, and multisystem disease. The detection of antineutrophil cytoplasmic antibodies (ANCA) in the blood is an important diagnostic marker; however, there are also ANCA-negative vasculitis syndromes. Immunosuppressive treatment is implemented to stop vascular inflammation. Specific (e.g., antiviral drugs) or symptomatic (e.g., NSAID) management may be necessary. If the vasculitis is secondary to an underlying disease, appropriate treatment of the underlying disease should be initiated. Treatment generally involves corticosteroids, and optionally methotrexate or cyclophosphamide. Surgical intervention may be required in the case of severe stenosis of major arteries.

C. Antiphospholipid Syndrome

Antiphospholipid syndrome or antiphospholipid antibody syndrome (APS or APLS), is an autoimmune, hypercoagulable state caused by antiphospholipid antibodies. APS provokes blood clots (thrombosis) in both arteries and veins as well as pregnancy-related complications such as miscarriage, stillbirth, preterm delivery, and severe preeclampsia. The diagnostic criteria require one clinical event (i.e., thrombosis or pregnancy complication) and two antibody blood tests spaced at least three months apart that confirm the presence of either lupus anticoagulant or anti-$\beta_2$-glycoprotein-I (since $\beta_2$-glycoprotein-I antibodies are a subset of anti-cardiolipin antibodies, an anti-cardiolipin assay can be performed as a less specific proxy).

APS can be primary or secondary. Primary APS occurs in the absence of any other related disease. Secondary APS occurs with other autoimmune diseases, such as systemic lupus erythematosus (SLE). In rare cases, APS leads to rapid organ failure due to generalized thrombosis; this is termed "catastrophic antiphospholipid syndrome" (CAPS or Asherson syndrome) and is associated with a high risk of death.

APS often requires treatment with anticoagulant medication such as heparin to reduce the risk of further episodes of thrombosis and improve the prognosis of pregnancy. Warfarin/Coumadin is not used during pregnancy because it can cross the placenta, unlike heparin, and is teratogenic.

The presence of antiphospholipid antibodies (aPL) in the absence of blood clots or pregnancy-related complications does not indicate APS (see below for the diagnosis of APS).

APS can cause arterial or venous blood clots, in any organ system, or pregnancy-related complications. In APS patients, the most common venous event is deep vein thrombosis of the lower extremities, and the most common arterial event is stroke. In pregnant women affected by APS, there is an increased risk of recurrent miscarriage, intrauterine growth restriction, and preterm birth. A frequent cause of such complications is placental infarctions. In some cases, APS seems to be the leading cause of mental and/or development retardation in the newborn, due to an aPL-induced inhibition of trophoblast differentiation. The APS responsible for most of the miscarriages in later trimesters seen in concomitant systemic lupus erythematosus and pregnancy.

Other common findings, although not part of the APS classification criteria, are low platelet count, heart valve disease, and livedo *reticularis*. There are also associations between aPL antibodies and headaches, migraines, and oscillopsia. Some studies have shown the presence of antiphospholipid antibodies in the blood and spinal fluid of patients with psychological symptoms. Very few patients with primary APS go on to develop SLE.

APS is tested for in the laboratory using both liquid phase coagulation assays (lupus anticoagulant) and solid phase ELISA assays (anti-cardiolipin antibodies). Genetic thrombophilia is part of the differential diagnosis of APS and can coexist in some APS patients. Presence of genetic thrombophilia may determine the need for anticoagulation therapy. Thus, genetic thrombophilia screening can consist of further studies for factor V Leiden variant and the prothrombin G20210A mutation, factor VIII, and levels, levels of protein C, free and total protein S, factor VIII, antithrombin, plasminogen, tissue plasminogen activator (TPA) and plasminogen activator inhibitor-1 (PAI-1). The testing of antibodies to the possible individual targets of aPL such as P2 glycoprotein 1 and antiphosphatidyl serine is currently under debate as testing for anticardiolipin appears to be currently sensitive and specific for diagnosis of APS even though cardiolipin is not considered an in vivo target for antiphospholipid antibodies.

Often, this disease is treated by giving aspirin to inhibit platelet activation, and/or warfarin as an anticoagulant. The goal of the prophylactic treatment with warfarin is to maintain the patient's INR between 2.0 and 3.0. It is not usually done in patients who have had no thrombotic symptoms.

Anticoagulation appears to prevent miscarriage in pregnant women. In pregnancy, low molecular weight heparin and low-dose aspirin are used instead of warfarin because of warfarin's teratogenicity. Women with recurrent miscarriage are often advised to take aspirin and to start low molecular weight heparin treatment after missing a menstrual cycle. In refractory cases plasmapheresis may be used.

D. Trauma

Physical trauma is a serious and body-altering physical injury, such as the removal of a limb. Blunt force trauma, a type of physical trauma caused by impact or other force applied from or with a blunt object, whereas penetrating trauma is a type of physical trauma in which the skin or tissues are pierced by an object. Trauma can also be described as both unplanned, such as an accident, or planned, in the case of surgery. Both can be characterized by mild to severe tissue damage, blood loss and/or shock, and both may lead to subsequent infection, including sepsis. The present invention provides to treatment of trauma, including both pretreatment (in the case of a medical procedure) and treatment after trauma injury as occurred.

1. Surgery

Surgery uses operative manual and instrumental techniques on a patient to investigate and/or treat a pathological condition such as disease or injury, to help improve bodily function or appearance, or sometimes for some other reason. The present invention can address trauma resulting from surgeries, as defined further below.

As a general rule, a procedure is considered surgical when it involves cutting of a patient's tissues or closure of a previously sustained wound. Other procedures that do not necessarily fall under this rubric, such as angioplasty or endoscopy, may be considered surgery if they involve common surgical procedure or settings, such as use of a sterile environment, anesthesia, antiseptic conditions, typical surgical instruments, and suturing or stapling. All forms of surgery are considered invasive procedures; so-called non-invasive surgery usually refers to an excision that does not penetrate the structure being addressed (e.g., laser ablation of the cornea) or to a radiosurgical procedure (e.g., irradiation of a tumor). Surgery can last from minutes to hours.

Surgical procedures are commonly categorized by urgency, type of procedure, body system involved, degree of invasiveness, and special instrumentation. Elective surgery is done to correct a non-life-threatening condition, and is carried out at the patient's request, subject to the surgeon's and the surgical facility's availability. Emergency surgery is surgery which must be done quickly to save life, limb, or functional capacity. Exploratory surgery is performed to aid or confirm a diagnosis. Therapeutic surgery treats a previously diagnosed condition.

Amputation involves cutting off a body part, usually a limb or digit. Replantation involves reattaching a severed body part. Reconstructive surgery involves reconstruction of an injured, mutilated, or deformed part of the body. Cosmetic surgery is done to improve the appearance of an otherwise normal structure. Excision is the cutting out of an organ, tissue, or other body part from the patient. Transplant surgery is the replacement of an organ or body part by insertion of another from different human (or animal) into the patient. Removing an organ or body part from a live human or animal for use in transplant is also a type of surgery.

When surgery is performed on one organ system or structure, it may be classed by the organ, organ system or tissue involved. Examples include cardiac surgery (performed on the heart), gastrointestinal surgery (performed within the digestive tract and its accessory organs), and orthopedic surgery (performed on bones and/or muscles).

Minimally invasive surgery involves smaller outer incision(s) to insert miniaturized instruments within a body cavity or structure, as in laparoscopic surgery or angioplasty.

By contrast, an open surgical procedure requires a large incision to access the area of interest. Laser surgery involves use of a laser for cutting tissue instead of a scalpel or similar surgical instruments. Microsurgery involves the use of an operating microscope for the surgeon to see small structures. Robotic surgery makes use of a surgical robot, such as Da Vinci or Zeus surgical systems, to control the instrumentation under the direction of the surgeon.

2. Traumatic Hemorrhage

Traumatic hemorrhage accounts for much of the wide-ranging international impact of injury, causing a large proportion of deaths and creating great morbidity in the injured. Despite differences in pre-hospital care, the acute management of traumatic hemorrhage is similar around the world and follows well accepted published guidelines. A critically injured patient's care occurs as four, often overlapping segments: the resuscitative, operative, and critical care phases. The diagnosis and control of bleeding should be a high priority during all of the phases of trauma care and is especially important in the patient who is in hemorrhagic shock. Early attempts at hemorrhage control include direct control of visible sources of severe bleeding with direct pressure, pressure dressings, or tourniquets; stabilization of long bone and pelvic fractures; and keeping the patient warm. During the resuscitative phase, warmed intravenous fluids, hypotensive resuscitation prior to surgical control of hemorrhage, and appropriate transfusion of blood and blood products are provided. In the operative phase, surgical control of the hemorrhage and any other injury, and additional transfusion is provided. Finally, the critical care phase provides for post-operative support and tissue perfusion.

E. Tumor Lysis Syndrome

Tumor lysis syndrome (TLS) is a group of metabolic abnormalities that can occur as a complication during the treatment of cancer, where large amounts of tumor cells are killed off (lysed) at the same time by the treatment, releasing their contents into the bloodstream. This occurs most commonly after the treatment of lymphomas and leukemias. In oncology and hematology, this is a potentially fatal complication, and patients at increased risk for TLS should be closely monitored before, during, and after their course of chemotherapy.

Tumor lysis syndrome is characterized by high blood potassium (hyperkalemia), high blood phosphate (hyperphosphatemia), low blood calcium (hypocalcemia), high blood uric acid (hyperuricemia), and higher than normal levels of blood urea nitrogen (BUN) and other nitrogen-containing compounds (azotemia). These changes in blood electrolytes and metabolites are a result of the release of cellular contents of dying cells into the bloodstream from breakdown of cells. In this respect, TLS is analogous to rhabdomyolysis, with comparable mechanism and blood chemistry effects but with different cause. In TLS, the breakdown occurs after cytotoxic therapy or from cancers with high cell turnover and tumor proliferation rates. The metabolic abnormalities seen in tumor lysis syndrome can ultimately result in nausea and vomiting, but more seriously acute uric acid nephropathy, acute kidney failure, seizures, cardiac arrhythmias, and death.

Symptoms include hyperkalemia, hyperphosphatemia, hypocalcemia, hyperuricemia and hyperuricosuria, acute uric acid nephropathy (AUAN), lactic acidosis and pretreatment spontaneous tumor lysis syndrome.

Treatment is first targeted at the specific metabolic disorder. One is acute kidney failure prior to chemotherapy. Since the major cause of acute kidney failure in this setting is uric acid build-up, therapy consists of rasburicase to wash out excessive uric acid crystals as well as a loop diuretic and fluids. Sodium bicarbonate should not be given at this time. If the patient does not respond, hemodialysis may be instituted, which is very efficient in removing uric acid, with plasma uric acid levels falling about 50% with each six-hour treatment. Another is acute kidney failure after chemotherapy. The major cause of acute kidney failure in this setting is hyperphosphatemia, and the main therapeutic means is hemodialysis. Forms of hemodialysis used include continuous arteriovenous hemodialysis (CAVHD), continuous venovenous hemofiltration (CVVH), or continuous venovenous hemodialysis (CVVHD).

F. Systemic Lupus Erythematosus (SLE)

SLE, also known simply as lupus, is an autoimmune disease in which the body's immune system mistakenly attacks healthy tissue in many parts of the body. Symptoms vary between people and may be mild to severe. Common symptoms include painful and swollen joints, fever, chest pain, hair loss, mouth ulcers, swollen lymph nodes, feeling tired, and a red rash which is most commonly on the face. Often there are periods of illness, called flares, and periods of remission during which there are few symptoms.

The cause of SLE is not clear. It is thought to involve genetics together with environmental factors. Among identical twins, if one is affected there is a 24% chance the other one will be as well. Female sex hormones, sunlight, smoking, vitamin D deficiency, and certain infections, are also believed to increase the risk. The mechanism involves an immune response by autoantibodies against a person's own tissues. These are most commonly anti-nuclear antibodies and they result in inflammation. Diagnosis can be difficult and is based on a combination of symptoms and laboratory tests. There are a number of other kinds of lupus erythematosus including discoid lupus erythematosus, neonatal lupus, and subacute cutaneous lupus erythematosus.

There is no cure for SLE. Treatments may include NSAIDs, corticosteroids, immunosuppressants, hydroxychloroquine, and methotrexate. Alternative medicine has not been shown to affect the disease. Life expectancy is lower among people with SLE. SLE significantly increases the risk of cardiovascular disease with this being the most common cause of death. With modern treatment about 80% of those affected survive more than 15 years. Women with lupus have pregnancies that are higher risk but are mostly successful.

Rate of SLE varies between countries from 20 to 70 per 100,000. Women of childbearing age are affected about nine times more often than men. While it most commonly begins between the ages of 15 and 45, a wide range of ages can be affected. Those of African, Caribbean, and Chinese descent are at higher risk than white people. Rates of disease in the developing world are unclear. Lupus is Latin for "wolf": the disease was so-named in the 13th century as the rash was thought to appear like a wolf's bite.

SLE is one of several diseases known as "the great imitator" because it often mimics or is mistaken for other illnesses. SLE is a classical item in differential diagnosis, because SLE symptoms vary widely and come and go unpredictably. Diagnosis can thus be elusive, with some people having unexplained symptoms of SLE for years.

Common initial and chronic complaints include fever, malaise, joint pains, muscle pains, and fatigue. Because these symptoms are so often seen in association with other diseases, these signs and symptoms are not part of the diagnostic criteria for SLE. When occurring in conjunction with other signs and symptoms (see below), however, they are considered suggestive.

While SLE can occur in both males and females, it is found far more often in women, and the symptoms associated with each sex are different. Females tend to have a greater number of relapses, a low white blood cell count, more arthritis, Raynaud's phenomenon, and psychiatric symptoms. Males tend to have more seizures, kidney disease, serositis (inflammation of tissues lining the lungs and heart), skin problems, and peripheral neuropathy.

Antinuclear antibody (ANA) testing and anti-extractable nuclear antigen (anti-ENA) form the mainstay of serologic testing for SLE. Several techniques are used to detect ANAs. Clinically the most widely used method is indirect immunofluorescence (IF). The pattern of fluorescence suggests the type of antibody present in the people's serum. Direct immunofluorescence can detect deposits of immunoglobulins and complement proteins in the people's skin. When skin not exposed to the sun is tested, a positive direct IF (the so-called lupus band test) is an evidence of systemic lupus erythematosus.

ANA screening yields positive results in many connective tissue disorders and other autoimmune diseases and may occur in normal individuals. Subtypes of antinuclear antibodies include anti-Smith and anti-double stranded DNA (dsDNA) antibodies (which are linked to SLE) and anti-histone antibodies (which are linked to drug-induced lupus). Anti-dsDNA antibodies are highly specific for SLE; they are present in 70% of cases, whereas they appear in only 0.5% of people without SLE. The anti-dsDNA antibody titers also tend to reflect disease activity, although not in all cases. Other ANA that may occur in people with SLE are anti-U1 RNP (which also appears in systemic sclerosis and mixed connective tissue disease), SS-A (or anti-Ro) and SS-B (or anti-La; both of which are more common in Sjögren's syndrome). SS-A and SS-B confer a specific risk for heart conduction block in neonatal lupus.

Other tests routinely performed in suspected SLE are complement system levels (low levels suggest consumption by the immune system), electrolytes and kidney function (disturbed if the kidney is involved), liver enzymes, and complete blood count.

The lupus erythematosus (LE) cell test was commonly used for diagnosis, but it is no longer used because the LE cells are only found in 50-75% of SLE cases, and they are also found in some people with rheumatoid arthritis, scleroderma, and drug sensitivities. Because of this, the LE cell test is now performed only rarely and is mostly of historical significance.

G. Sickle Cell Disease (SCD)

SCD is a mutation in the beta globin chain that results in the $6^{th}$ amino acid being valine instead of a glutamic acid. The loss of charge results in hemoglobin polymerization inside red cells under low oxygen tension. While SCD provides protection from cerebral falciparum malaria, it is also a severe hemolytic anemia associated with recurrent vaso-occlusive episodes (VOEs) and multi-organ damage. SCD is now recognized to have a major inflammatory component and patients consequently need to avoid steroid exposure or risk getting severe VOEs. They must also avoid exposure to neutrophil stimulating granulocyte colony growth factor (G-CSF) for the same reason. Antibodies to selectins on the surface of neutrophils to impair their function has been used to decrease VOEs. It has been shown that NETs occur in SCD and that strategies to decrease NETs decrease the inflammatory and SCD severity in murine models.

IV. Treatments for Sepsis

A. Prior Efforts to Improve Outcome in Sepsis

Therapeutic interventions to improve outcome in sepsis beyond standard supportive measures mentioned above have not materialized. Activated protein C, thought to stabilize the endothelial lining and protecting against organ damage, was first thought to have therapeutic value, but in further studies had too much bleeding complications and no improvement in survival. Others have proposed used of fresh frozen plasma as a therapeutic intervention, but again no clear benefit has been shown other than it being an osmotic load to maintain cardiovascular volume. Heparin has been touted too as a potential therapeutic agent, but studies have had mixed results. Heparin, as one of its effects, likely binds to the histones and other anionic proteins complexed to the DNA on NETs and likely enhances the lyses of NETs and frees NDPs so that by this pathway may worsen outcome in sepsis. The inventors believe that, instead, NETs should be protected from lysis in part by compaction and concurrently the NDPS should be sequestered within the compacted DNA to be effective in improving outcome in sepsis.

As mentioned above, PF4 compacts NETs and the inventors have shown that PF4 improves survival and lowers NDP product release in an LPS endotoxemic model of sepsis. Others have shown that PF4 also binds to the wall of bacteria and also bind to released LPS from such walls. But such outcome required studies in the setting of PF4-deficient mice. Likely in sepsis, patients have very high levels of circulating free PF4 from massive platelet degranulation and so infusion of PF4 may or may not be effective on its own. In their studies, the inventors found that in mice studies infusion of a modified KKO that crossbinds PF4-NETs complexes and also known to crossbind PF4-LPS, appears to be much more effective and also can be used in combination with infusions of PF4, if the Fc portion of the antibody is inactivated.

B. Antibodies to PF4/Polyanions Like Heparin, NETs and LPS

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In particular embodiments, the antibody is purified: (1) to greater than 95% by weight of antibody as determined by the Lowry method, and most particularly more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

The basic four-chain antibody immunoglobulin (Ig) unit is a heterotetrameric glycoprotein composed of two identical light (L) chains and two identical heavy (H) chains. An IgM antibody consists of 5 basic heterotetramer units along with an additional polypeptide called J chain, and therefore contain 10 antigen binding sites, while secreted IgA antibodies can polymerize to form polyvalent assemblages comprising 2-5 of the basic 4-chain units along with J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable region ($V_H$) followed by three constant domains ($C_H$) for each of the alpha and gamma chains and four $C_H$ domains for mu and isotypes. Each L chain has at the N-terminus, a variable region ($V_L$) followed by a constant domain ($C_L$) at its other end. The $V_L$ is aligned with the $V_H$ and the CL is aligned with the first constant domain of the heavy chain ($C_{H1}$). Particular amino acid residues are believed to form an interface between the light chain and heavy chain variable regions. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The L chain from any vertebrate species can be assigned to one of two clearly distinct types, called kappa and lambda based on the amino acid sequences of their constant domains ($C_L$). Depending on the amino acid sequence of the constant domain of their heavy chains ($C_H$), immunoglobulins can be assigned to different classes or isotypes. There are five classes of immunoglobulins: IgA, IgD, IgE, IgG, and IgM, having heavy chains designated alpha, delta, epsilon, gamma and mu, respectively. They gamma and alpha classes are further divided into subclasses on the basis of relatively minor differences in $C_H$ sequence and function, humans express the following subclasses: IgG1, IgG2, IgG3, IgG4, IgA1, and IgA2.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC), antibody-dependent cellular phagocytosis (ADCP), antibody-dependent neutrophil phagocytosis (ADNP), and antibody-dependent complement deposition (ADCD).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. et al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_{sub}$H when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "moAb" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each moAb is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present disclosure may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567) after single cell sorting of an antigen specific B cell, an antigen specific plasmablast responding to an infection or immunization, or capture of linked heavy and light chains from single cells in a bulk sorted antigen specific collection. The "monoclonal antibodies" may also be isolated from phage antibody libraries using the techniques described in Clackson et al., Nature, 352:624-628 (1991) and Marks et al., J. Mol. Biol., 222: 581-597 (1991), for example.

1. General Methods

It will be understood that monoclonal antibodies binding to PF4 will have several applications. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies generally begin along the same lines as those for preparing polyclonal antibodies. The first step for both these methods is immunization of an appropriate host or identification of subjects who are immune due to prior natural infection or vaccination with a licensed or experimental vaccine. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants in animals include complete Freund's adjuvant (a non-specific stimulator of the immune response containing killed *Mycobacterium tuberculosis*), incomplete Freund's adjuvants and aluminum hydroxide adjuvant and in humans include alum, CpG, MFP59 and combinations of immunostimulatory molecules ("Adjuvant Systems", such as AS01 or AS03). Additional experimental forms of inoculation to induce PF4-specific B cells is possible, including nanoparticle vaccines, or gene-encoded antigens delivered as DNA or RNA genes in a physical delivery system (such as lipid nanoparticle or on a gold biolistic bead), and delivered with needle, gene gun, transcutaneous electroporation device. The antigen gene also can be carried as encoded by a replication competent or defective viral vector such as adenovirus, adeno-associated virus, poxvirus, herpesvirus, or alphavirus replicon, or alternatively a virus like particle.

In the case of human antibodies against natural pathogens, a suitable approach is to identify subjects that have been exposed to the pathogens, such as those who have been diagnosed as having contracted the disease, or those who have been vaccinated to generate protective immunity against the pathogen or to test the safety or efficacy of an experimental vaccine. Circulating anti-pathogen antibodies can be detected, and antibody encoding or producing B cells from the antibody-positive subject may then be obtained.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate monoclonal antibodies.

Following immunization, somatic cells with the potential for producing antibodies, specifically B lymphocytes (B cells), are selected for use in the moAb generating protocol. These cells may be obtained from biopsied spleens, lymph nodes, tonsils or adenoids, bone marrow aspirates or biopsies, tissue biopsies from mucosal organs like lung or GI tract, or from circulating blood. The antibody-producing B lymphocytes from the immunized animal or immune human are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art. HMMA2.5 cells or MFP-2 cells are particularly useful examples of such cells.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. In some cases, transformation of human B cells with Epstein Barr virus (EBV) as an initial step increases the size of the B cells, enhancing fusion with the relatively large-sized myeloma cells. Transformation efficiency by EBV is enhanced by using CpG and a Chk2 inhibitor drug in the transforming medium. Alternatively, human B cells can be activated by co-culture with transfected cell lines expressing CD40 Ligand (CD154) in medium containing additional soluble factors, such as IL-21 and human B cell Activating Factor (BAFF), a Type II member of the TNF superfamily. Fusion methods using Sendai virus have been described, and those using polyethylene glycol (PEG), such as 37% (v/v) PEG. The use of electrically induced fusion methods also is appropriate and there are processes for better efficiency. Fusion procedures usually produce viable hybrids at low frequencies, about $1\times10^{-6}$ to $1\times10^{-8}$, but with optimized procedures one can achieve fusion efficiencies close to 1 in 200. However, relatively low efficiency of fusion does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture medium. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the medium is supplemented with hypoxanthine and thymidine as a source of nucleotides (HAT medium). Where azaserine is used, the medium is supplemented with hypoxanthine. Ouabain is added if the B cell source is an EBV-transformed human B cell line, in order to eliminate EBV-transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide monoclonal antibodies. The cell lines may be exploited for MoAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as severe combined immunodeficient (SCID) mice, to prevent tumor rejection. The injected animal develops tumors secreting the specific moAb produced by the fused cell hybrid. The body fluids of the animal, such as serum or ascites fluid, can then be tapped to provide monoclonal antibodies in high concentration. The individual cell lines could also be cultured in vitro, where the Monoclonal antibodies are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

Monoclonal antibodies produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, moAb fragments encompassed by the present disclosure can be synthesized using an automated peptide synthesizer.

It also is contemplated that a molecular cloning approach may be used to generate monoclonal antibodies. Single B cells labelled with the antigen of interest can be sorted physically using paramagnetic bead selection or flow cytometric sorting, then RNA can be isolated from the single cells and antibody genes amplified by RT-PCR. Alternatively, antigen-specific bulk sorted populations of cells can be segregated into microvesicles and the matched heavy and light chain variable genes recovered from single cells using physical linkage of heavy and light chain amplicons, or common barcoding of heavy and light chain genes from a vesicle. Matched heavy and light chain genes form single cells also can be obtained from populations of antigen specific B cells by treating cells with cell-penetrating nanoparticles bearing RT-PCR primers and barcodes for marking transcripts with one barcode per cell. The antibody variable genes also can be isolated by RNA extraction of a hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

2. Antibodies of the Present Disclosure

Antibodies according to the present disclosure may be defined, in the first instance, by their binding specificity, i.e., binding to PF4 in the presence of a polyanion such as heparin or that bind to specific components of NETs such as the DNA or lipopolysaccharides. Preliminary data focus on antibodies to PF4 with a polyanion, but similar concepts can apply to those directly binding DNA or to other NET components like histones. Those of skill in the art, by assessing the binding specificity/affinity of a given antibody using techniques well known to those of skill in the art, can determine whether such antibodies fall within the scope of the instant claims. For example, the epitope to which a given antibody bind may consist of a single contiguous sequence of 3 or more (e.g., 3, 4, 5, 6, 7, 8, 9, 10, 11, 12, 13, 14, 15, 16, 17, 18, 19, 20) amino acids located within the antigen molecule (e.g., a linear epitope in a domain). Alternatively, the epitope may consist of a plurality of non-contiguous amino acids (or amino acid sequences) located within the antigen molecule (e.g., a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Cross-blocking can be measured in various binding assays such as ELISA, biolayer interferometry, or surface plasmon resonance. Other methods include alanine scanning mutational analysis, peptide blot analysis (Reineke (2004) Methods Mol. Biol. 248: 443-63), peptide cleavage analysis, high-resolution electron microscopy techniques using single particle reconstruction, cryoEM, or tomography, crystallographic studies and NMR analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/ antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267: 252-259; Engen and Smith (2001) Anal. Chem. 73: 256A-265A.

The term "epitope" refers to a site on an antigen to which B and/or T cells respond. B-cell epitopes can be formed both from contiguous amino acids or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (monoclonal antibodies) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce monoclonal antibodies having the desired characteristics. MAP may be used to sort the antibodies of the disclosure into groups of antibodies binding different epitopes.

The present disclosure includes antibodies that may bind to the same epitope, or a portion of the epitope. Likewise, the present disclosure also includes antibodies that compete for binding to a target or a fragment thereof with any of the specific exemplary antibodies described herein. One can easily determine whether an antibody binds to the same epitope as, or competes for binding with, a reference antibody by using routine methods known in the art. For example, to determine if a test antibody binds to the same epitope as a reference, the reference antibody is allowed to bind to target under saturating conditions. Next, the ability of a test antibody to bind to the target molecule is assessed. If the test antibody is able to bind to the target molecule following saturation binding with the reference antibody, it can be concluded that the test antibody binds to a different epitope than the reference antibody. On the other hand, if the test antibody is not able to bind to the target molecule following saturation binding with the reference antibody, then the test antibody may bind to the same epitope as the epitope bound by the reference antibody.

The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, as variants having altered CH1, hinge, CH2, CH3 or CH4 regions, so as to form, for example antibodies, etc., having variant Fc regions that exhibit enhanced or impaired effector or binding characteristics. The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc., content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment, the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002), J. Biol. Chem. 277(30): 26733-26740; Davies J. et al. (2001), Biotechnology & Bioengineering 74(4): 288-294). Methods of altering carbohydrate contents are known to those skilled in the art, see, e.g., Wallick, S. C. et al. (1988), J. Exp. Med. 168(3): 1099-1109; Tao, M. H. et al. (1989), J. Immunol. 143(8): 2595-2601; Routledge, E. G. et al. (1995), Transplantation 60(8):847-53; Elliott, S. et al. (2003), Nature Biotechnol. 21:414-21; Shields, R. L. et al. (2002), J. Biol. Chem. 277(30): 26733-26740).

A derivative antibody or antibody fragment can be generated with an engineered sequence or glycosylation state to confer preferred levels of activity in antibody dependent cellular cytotoxicity (ADCC), antibody-dependent cellular phagocytosis (ADCP), antibody-dependent neutrophil phagocytosis (ADNP), or antibody-dependent complement deposition (ADCD) functions as measured by bead-based or cell-based assays or in vivo studies in animal models.

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

3. Engineering of Antibody Sequences

In various embodiments, one may choose to engineer sequences of the identified antibodies for a variety of reasons, such as improved expression, improved cross-reactivity or diminished off-target binding. The inventors specifically focus on removing secondary events due to the Fc portion of the antibodies that may lead to triggering a proinflammatory or related downstream pathway. They are also modifying antibodies to decrease antigenicity and enhance antigen target affinity. Modified antibodies may be made by any technique known to those of skill in the art, including expression through standard molecular biological techniques, or the chemical synthesis of polypeptides. Methods for recombinant expression are addressed elsewhere in this document. The following is a general discussion of relevant goals techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full-length IgG antibodies can be generated by subcloning heavy and light chain Fv DNAs from the cloning vector into an IgG plasmid vector, transfected into 293 (e.g., Freestyle) cells or CHO cells, and antibodies can be collected and purified from the 293 or CHO cell supernatant. Other appropriate host cells systems include bacteria, such as *E. coli*, insect cells (S2, Sf9, Sf29, High Five), plant cells (e.g., tobacco, with or without engineering for human-like glycans), algae, or in a variety of non-human transgenic contexts, such as mice, rats, goats or cows.

Expression of nucleic acids encoding antibodies, both for the purpose of subsequent antibody purification, and for immunization of a host, is also contemplated. Antibody coding sequences can be RNA, such as native RNA or modified RNA. Modified RNA contemplates certain chemical modifications that confer increased stability and low immunogenicity to mRNAs, thereby facilitating expression of therapeutically important proteins. For instance, N1-methyl-pseudouridine (NImΨ) outperforms several other nucleoside modifications and their combinations in terms of translation capacity. In addition to turning off the immune/eIF2α phosphorylation-dependent inhibition of translation, incorporated N1mΨ nucleotides dramatically alter the dynamics of the translation process by increasing ribosome pausing and density on the mRNA. Increased ribosome loading of modified mRNAs renders them more permissive for initiation by favoring either ribosome recycling on the same mRNA or de novo ribosome recruitment. Such modifications could be used to enhance antibody expression in vivo following inoculation with RNA. The RNA, whether native or modified, may be delivered as naked RNA or in a delivery vehicle, such as a lipid nanoparticle.

Alternatively, DNA encoding the antibody may be employed for the same purposes. The DNA is included in an expression cassette comprising a promoter active in the host cell for which it is designed. The expression cassette is advantageously included in a replicable vector, such as a conventional plasmid or minivector. Vectors include viral vectors, such as poxviruses, adenoviruses, herpesviruses, adeno-associated viruses, and lentiviruses are contemplated. Replicons encoding antibody genes such as alphavirus replicons based on VEE virus or Sindbis virus are also contemplated. Delivery of such vectors can be performed by needle through intramuscular, subcutaneous, or intradermal routes, or by transcutaneous electroporation when in vivo expression is desired.

The rapid availability of antibody produced in the same host cell and cell culture process as the final cGMP manufacturing process has the potential to reduce the duration of process development programs. LONZA™ has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), $F(ab')_2$) that are produced, for example, by the proteolytic cleavage of the monoclonal antibodies, or single-chain immunoglobulins producible, for example, via recombinant means. F(ab') antibody derivatives are monovalent, while $F(ab')_2$ antibody derivatives are bivalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

Another embodiment of the present disclosure comprises a moAb with a reduced glycosylation profile. Glycosylation of an Fc region is typically either N-linked or O-linked. N-linked refers to the attachment of the carbohydrate moiety to the side chain of an asparagine residue. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site. The glycosylation pattern may be altered, for example, by deleting one or more glycosylation site(s) found in the polypeptide, and/or adding one or more glycosylation site(s) that are not present in the polypeptide. Cell lines can be altered to reduce or eliminate certain post-translational modifications, such as glycosylation, using genome editing technology such as Clustered Regularly Interspaced Short Palindromic Repeats (CRISPR). For example, CRISPR technology can be used to eliminate genes encoding glycosylating enzymes in 293 or CHO cells used to express recombinant monoclonal antibodies.

It is possible to engineer the antibody variable gene sequences obtained from human B cells to enhance their manufacturability and safety. Potential protein sequence liabilities can be identified by searching for sequence motifs associated with sites containing:

1) Unpaired Cys residues,
2) N-linked glycosylation,
3) Asn deamidation,
4) Asp isomerization,
5) SYE truncation,
6) Met oxidation,
7) Trp oxidation,
8) N-terminal glutamate,
9) Integrin binding,
10) CD11c/CD18 binding, or
11) Fragmentation Such motifs can be eliminated by altering the synthetic gene for the cDNA encoding recombinant antibodies.

Protein engineering efforts in the field of development of therapeutic antibodies clearly reveal that certain sequences or residues are associated with solubility differences (Fernandez-Escamilla et al., *Nature Biotech.,* 22 (10), 1302-1306, 2004; Chennamsetty et al., *PNAS,* 106 (29), 11937-11942, 2009; Voynov et al., *Biocon. Chem.,* 21 (2), 385-392, 2010) Evidence from solubility-altering mutations in the literature indicate that some hydrophilic residues such as aspartic acid, glutamic acid, and serine contribute significantly more favorably to protein solubility than other hydrophilic residues, such as asparagine, glutamine, threonine, lysine, and arginine.

Antibodies can be engineered for enhanced biophysical properties. One can use elevated temperature to unfold antibodies to determine relative stability, using average apparent melting temperatures. Differential Scanning Calorimetry (DSC) measures the heat capacity, Cp, of a molecule (the heat required to warm it, per degree) as a function of temperature. One can use DSC to study the thermal stability of antibodies. DSC data for monoclonal antibodies is particularly interesting because it sometimes resolves the unfolding of individual domains within the moAb structure, producing up to three peaks in the thermogram (from unfolding of the Fab, $C_H2$, and $C_H3$ domains). Typically unfolding of the Fab domain produces the strongest peak. The DSC profiles and relative stability of the Fc portion show characteristic differences for the human $IgG_1$, $IgG_2$, $IgG_3$, and $IgG_4$ subclasses (Garber and Demarest, *Biochem. Biophys. Res. Commun.* 355, 751-757, 2007). One also can determine average apparent melting temperature using circular dichroism (CD), performed with a CD spectrometer. Far-UV CD spectra will be measured for antibodies in the range of 200 to 260 nm at increments of 0.5 nm. The final spectra can be determined as averages of 20 accumulations. Residue ellipticity values can be calculated after background subtraction. Thermal unfolding of antibodies (0.1 mg/mL) can be monitored at 235 nm from 25-95° C. and a heating rate of 1° C./min. One can use dynamic light scattering (DLS) to assess for propensity for aggregation. DLS is used to characterize size of various particles including proteins. If the system is not disperse in size, the mean effective diameter of the particles can be determined. This measurement depends on the size of the particle core, the size of surface structures, and particle concentration. Since DLS essentially measures fluctuations in scattered light intensity due to particles, the diffusion coefficient of the particles can be determined. DLS software in commercial DLA instruments displays the particle population at different diameters. Stability studies can be done conveniently using DLS. DLS measurements of a sample can show whether the particles aggregate over time or with temperature variation by determining whether the hydrodynamic radius of the particle increases. If particles aggregate, one can see a larger population of particles with a larger radius. Stability depending on temperature can be analyzed by controlling the temperature in situ. Capillary electrophoresis (CE) techniques include proven methodologies for determining features of antibody stability. One can use an iCE approach to resolve antibody protein charge variants due to deamidation, C-terminal lysines, sialylation, oxidation, glycosylation, and any other change to the protein that can result in a change in pI of the protein. Each of the expressed antibody proteins can be evaluated by high throughput, free solution isoelectric focusing (IEF) in a capillary column (cIEF), using a Protein Simple Maurice instrument. Whole-column UV absorption detection can be performed every 30 seconds for real time monitoring of molecules focusing at the isoelectric points (pls). This approach combines the high resolution of traditional gel IEF with the advantages of quantitation and automation found in column-based separations while eliminating the need for a mobilization step. The technique yields reproducible, quantitative analysis of identity, purity, and heterogeneity profiles for the expressed antibodies. The results identify charge heterogeneity and molecular sizing on the antibodies, with both absorbance and native fluorescence detection modes and with sensitivity of detection down to 0.7 μg/mL.

One can determine the intrinsic solubility score of antibody sequences. The intrinsic solubility scores can be calculated using CamSol Intrinsic (Sormanni et al., *J Mol Biol* 427, 478-490, 2015). The amino acid sequences for residues 95-102 (Kabat numbering) in HCDR3 of each antibody fragment such as a scFv can be evaluated via the online program to calculate the solubility scores. One also can determine solubility using laboratory techniques. Various techniques exist, including addition of lyophilized protein to a solution until the solution becomes saturated and the solubility limit is reached, or concentration by ultrafiltration in a microconcentrator with a suitable molecular weight cut-off. The most straightforward method is induction of amorphous precipitation, which measures protein solubility using a method involving protein precipitation using ammonium sulfate (Trevino et al., *J Mol Biol,* 366: 449-460, 2007). Ammonium sulfate precipitation gives quick and accurate information on relative solubility values. Ammonium sulfate precipitation produces precipitated solutions with well-defined aqueous and solid phases and requires relatively small amounts of protein. Solubility measurements performed using induction of amorphous precipitation by ammonium sulfate also can be done easily at different pH values. Protein solubility is highly pH dependent, and pH is considered the most important extrinsic factor that affects solubility.

Autoreactivity. Generally, it is thought that autoreactive clones should be eliminated during ontogeny by negative selection, however it has become clear that many human, naturally-occurring antibodies with autoreactive properties persist in adult mature repertoires, and the autoreactivity may enhance the antiviral function of many antibodies to pathogens. It has been noted that HCDR3 loops in antibodies during early B cell development are often rich in positive charge and exhibit autoreactive patterns (Wardemann et al., *Science* 301, 1374-1377, 2003). One can test a given antibody for autoreactivity by assessing the level of binding to human origin cells in microscopy (using adherent HeLa or HEp-2 epithelial cells) and flow cytometric cell surface staining (using suspension Jurkat T cells and 293S human embryonic kidney cells). Autoreactivity also can be surveyed using assessment of binding to tissues in tissue arrays.

Preferred residues ("Human Likeness"). B cell repertoire deep sequencing of human B cells from blood donors is being performed on a wide scale in many recent studies. Sequence information about a significant portion of the human antibody repertoire facilitates statistical assessment of antibody sequence features common in healthy humans. With knowledge about the antibody sequence features in a human recombined antibody variable gene reference database, the position specific degree of "Human Likeness" (HL) of an antibody sequence can be estimated. HL has been shown to be useful for the development of antibodies in clinical use, like therapeutic antibodies or antibodies as vaccines. The goal is to increase the human likeness of antibodies to reduce potential adverse effects and anti-antibody immune responses that will lead to significantly decreased efficacy of the antibody drug or can induce serious health implications. One can assess antibody characteristics of the combined antibody repertoire of three healthy human blood donors of about 400 million sequences in total and created a novel "relative Human Likeness" (rHL) score that focuses on the hypervariable region of the antibody. The rHL score allows one to easily distinguish between human (positive score) and non-human sequences (negative score). Antibodies can be engineered to eliminate residues that are not common in human repertoires.

4. Single-Chain Antibodies

A single chain variable fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma or B cell. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alanine, serine and glycine. However, other residues can function as well. Phage display has been used as a means of rapidly selecting tailored linkers for single-chain antibodies (scFvs) from protein linker libraries. A random linker library can be constructed in which the genes for the heavy and light chain variable domains are linked by a segment encoding an 18-amino acid polypeptide of variable composition. The scFv repertoire (approx. $5\times10^6$ different members) is displayed on filamentous phage and subjected to affinity selection with hapten. The population of selected variants has been shown to exhibit significant increases in binding activity but retained considerable sequence diversity. Screening subsequently yields a catalytically active scFv that was produced efficiently in soluble form. Sequence analysis reveals a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane. The use of such cross-linkers is well understood in the art. Another embodiment involves the use of flexible linkers.

U.S. Pat. No. 4,680,338 describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

5. Purification

In certain embodiments, the anti-PF4 antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE. It will therefore be appreciated that under differing electrophoresis conditions, the apparent molecular weights of purified or partially purified expression products may vary.

6. HIT-Like, Anti-PF4 Antibodies

Anti-PF4 antibodies are well known in the art. For example, Arepally et al., *Blood* 95(5): 1533-40 (2000) reported the characterization of an $IgG_{2b\kappa}$ antibody called KKO that was developed to recapitulate disease-causing antibodies in HIT. The same Investigators obtained U.S. Pat. No. 9,615,872, which disclosed compositions, kits and methods comprising a moAb which shares key functional properties with the polyclonal antibodies which participate in the pathogenesis of HIT/thrombosis (HIT/HITT) in a mammal. These antibodies bind with a PF4/heparin complex relative to the binding of the antibody with PF4 or heparin alone. The antibodies also bind specifically with PF4 in a complex with other GAGs besides heparin, and also activates platelets. The antibodies are stated to be useful in methods for diagnosing and treating HIT/HITT in a mammal, but no mention of sepsis is made. A humanized version of the moAb was also described, along with a process for humanizing the moAb of the invention. See also U.S. Pat. Nos. 6,964,854 and 7,728,115 for disclosures relating to anti-PF4 antibodies. This KKO antibody is available from the American Type Culture Collection (PTA-6133) and is available for purchase from ThermoFisher (catalog no. MA5-17641).

B. PF4

PF4 is a small cytokine belonging to the CXC chemokine family and is also known as chemokine (C-X-C motif) ligand 4 (CXCL4). This chemokine is the most abundant alpha-granular protein and is released from alpha-granules of activated platelets during platelet aggregation and promotes blood coagulation by moderating the effects of heparin-like molecules. Due to these roles, it is predicted to play a role in thrombosis and likely other related processes. It is usually found in a complex with proteoglycan.

The gene for human PF4 is located on human chromosome 4. The human protein sequence is referenced at NP_002610 and NP_001350281. The human mRNA is referenced at NM_002619 and NM_001363352.

PF4 is a 70-amino acid protein that is released from the alpha-granules of activated platelets and binds with high affinity to heparin. Its major physiologic role appears to be neutralization of heparin-like negatively charged molecules on the platelets and endothelial surfaces o and allowing platelets to approach the endothelial lining, promoting coagulation.

PF4 may be a chemoattractant for neutrophils, fibroblasts and monocytes, and interacts with a splice variant of the chemokine receptor CXCR3, known as CXCR3B. The heparin:PF4 complex is the antigen in heparin-induced thrombocytopenia, an idiosyncratic autoimmune reaction to the administration of the anticoagulant heparin. PF4 autoantibodies have also been found in patients with thrombosis and features resembling HIT, but no prior administration of heparin. It is increased in patients with systemic sclerosis that also have interstitial lung disease. PF4 kills malaria parasites within erythrocytes by selectively lysing the parasite's digestive vacuole.

C. Pharmaceutical Compositions

Also provided herein are pharmaceutical compositions and formulations comprising PF4 and/or deglycosylated anti-PF4/heparin antibodies and a pharmaceutically acceptable carrier. Pharmaceutical compositions and formulations as described herein can be prepared by mixing the active ingredients (i.e., PF4 or deglycosylated anti-PF4/heparin antibody) having the desired degree of purity with one or more optional pharmaceutically acceptable carriers (Remington's Pharmaceutical Sciences 22nd edition, 2012), in the form of aqueous solutions. Pharmaceutically acceptable carriers are generally nontoxic to recipients at the dosages and concentrations employed, and include, but are not limited to buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as polyethylene glycol (PEG). Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in U.S. Patent Publication Nos. 2005/0260186 and 2006/0104968. In one aspect, a sHASEGP is combined with one or more additional glycosaminoglycanases such as chondroitinases.

D. Combination Therapies

In certain embodiments, the compositions and methods of the present embodiments involve PF4 and/or deglycosylated anti-PF4/heparin antibodies in combination with at least one additional therapy. The additional therapy may be antibiotics, IV fluids, blood products, vasopressors, steroids, anesthesia, Early Goal Directed therapy, NETosis-inhibiting drugs or drugs that accelerate NET lysis.

A PF4 protein and/or deglycosylated anti-PF4/heparin antibody therapy may be administered before, during, after, or in various combinations relative to an additional cancer therapy, such as immune checkpoint therapy. The administrations may be in intervals ranging from concurrently to minutes to days to weeks. In some embodiments where the PF4 or deglycosylated anti-PF4/heparin antibody therapy is provided to a patient separately from an additional therapeutic agent, one would generally ensure that a significant period of time did not expire between the time of each delivery, such that the two compounds would still be able to exert an advantageously combined effect on the patient. In such instances, it is contemplated that one may provide a patient with the antibody therapy and the anti-cancer therapy within about 12 to 24 or 72 h of each other and, more particularly, within about 6-12 h of each other. In some situations, it may be desirable to extend the time period for treatment significantly where several days (2, 3, 4, 5, 6, or 7) to several weeks (1, 2, 3, 4, 5, 6, 7, or 8) lapse between respective administrations.

Various combinations may be employed. For the example below the PF4 or the deglycosylated anti-PF4/heparin antibody therapy is "A" and the other therapy is "B":

| | | | | | |
|---|---|---|---|---|---|
| A/B/A | B/A/B B/B/A | A/A/B | A/B/B B/A/A | A/B/B/B | B/A/B/B |
| B/B/B/A | B/B/A/B | A/A/B/B | A/B/A/B | A/B/B/A | B/B/A/A |
| B/A/B/A | B/A/A/B | A/A/A/B | B/A/A/A | A/B/A/A | A/A/B/A |

Administration of any compound or therapy of the present embodiments to a patient will follow general protocols for the administration of such compounds, taking into account the toxicity, if any, of the agents. Therefore, in some embodiments there is a step of monitoring toxicity that is attributable to combination therapy.

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods for PF4 and KKO Studies in HIT

Mice and human samples. HIT mice were transgenic for both platelet-specific hPF4 ($hPF4^+$) and human FcγRIIa ($Fc\gamma RIIa^+$) (Reilly et al., 2001). All HIT mice were also on a $cxcl4^{-/-}$ background (Kowalska et al., 2010), as murine PF4 is not recognized by HIT antibodies (Eslin et al., 2004). Genetic alterations were confirmed by PCR analyses (Zhang et al., 2001). The inventors used the CRISPR-Cas9 genome editing system (Cong and Zhang, 2015) to disrupt Padi4 exon2 in HIT mice ($Padi4^{-/-}$/HIT mice, FIG. 15A). Guide RNA (gRNA) flanking the targeted exon was designed to minimize off-target interactions (Doench et al., 2016) (5'-CCTAAGGGCTACACAACCTT-3' (SEQ ID NO: 1) and 5'-GCTGGCTGCTTTCA CCTGTAC-3' (SEQ ID NO: 2)) and injected into harvested embryos at concentrations of 50 ng/μl along with Cas9 mRNA 100 ng/μl at the Children's Hospital of Philadelphia (CHOP).

Oligonucleotide primers designed to amplify the 0.2 kb region of the gene encasing Exon 2 (5'-CATCTGTTCTGCTGCTGGCTG-3' (SEQ ID NO: 3), 5'-CTCCTAAGGGCTACACAACCTTC-3' (SEQ ID NO: 4)) were used to confirm the presence of the desired gene disruption. Functional abrogation of PAD4 activity was confirmed by stimulating neutrophils isolated from the bone marrow of $Padi4^{-/-}$ mice and plated on poly-L-lysine-coated slides (SIGMA-ALDRICH™) with 100 nM of phorbol-12 myristate 13-acetate (PMA, SIGMA-ALDRICH™) overnight at 37° C. and then staining the cells with SYTOX green (1 μM) and anti-citrullinated histone H3 antibody Ab5103 (anti-citH3, SIGMA-ALDRICH™) at a dilution of 1:500 to visualize NET release (FIG. 15C). Both $Padi4^{+/+}$/HIT and $Padi4^{-/-}$/HIT mice were studied at 10-30 weeks of age. Only male mice were used in the cremaster vessel injury experiments; however, in previous studies, the inventors have not appreciated any sex differences in thrombosis in the passive immunization HIT murine model following photochemical carotid artery injury (Rauova et al., 2010).

Deidentified plasma samples were obtained from patients with suspected HIT (Cuker et al., 2010). All subjects were evaluated with a polyspecific PF4/heparin ELISA (Immucor) (Arepally et al., 2000) and a serotonin-release assay (Cuker et al., 2014; Arepally et al., 1995), and classified as having or not having HIT by a panel of three independent expert adjudicators who based their decision on laboratory results and clinical findings. Control plasma was obtained from healthy individuals and patients diagnosed with immune thrombocytopenia (ITP) (Lambert and Gernsheimer, 2017). Citrated plasma was stored at −80° C. and myeloperoxidase-DNA (MPO-DNA) complex levels and cfDNA levels were also measured as previously described. (Caudrillier et al., J Clin Invest. 2012 July; 122(7):2661-71). IgG was isolated from plasma from HIT patients and healthy donors using protein G agarose (Pierce) (Rauova et al., 2006).

NET-lined microfluidic channel studies. Experiments were performed using a BIOFLUX™ 200 Controller (Fluxion) as described (Tutwiler et al., 2016). The BIOFLUX™ channels were visualized with an AXIO™ Observer Z1 inverted microscope (ZEISS™) equipped with a motorized stage and an HXP-120 C metal halide illumination source. The microscope and image acquisition were controlled by BIOFLUX™ Montage software with a MetaMorph-based platform (MOLECULAR DEVICES™). Isolated human neutrophils ($2\times10^6$ cells/ml) were incubated with 1 ng/ml tumor-necrosis factor (TNF) a (GIBCO™) at room temperature for 10 minutes and then flowed through channels coated with 50 μg/ml of fibronectin (SIGMA-ALDRICH™), to which they adhere, and then incubated with 100 ng/ml PMA overnight at 37° C. Cell-free DNA (cfDNA) release was visualized with 1 μM SYTOX green or orange, and the channels were infused with recombinant PF4 (0-200 μg/ml), expressed and purified as the inventors described (Sachais et al., 2012), with or without unfractionated porcine heparin (0.4 U/ml, BD Biosciences) at 2-5 dynes/$cm^2$. To confirm that the cfDNA structures adherent to the microfluidic channel walls were NETs, the inventors performed co-immunolocalization in which channels±PF4 (25 μg/ml) were incubated with either anti-citH3 at 4° C. overnight or anti-MPO at 37° C. for 1 hour, and then incubated with an ALEXA FLUOR™ 594 conjugated secondary antibody for 1 hour at 37° C. prior to imaging with a ZEISS™ LSM 710 laser-scanning confocal microscope. Structures with co-localization of cfDNA and MPO or citrullinated histones were deemed to be NETs. PF4-NET complexes were then incubated with 25 μg/ml of KKO, a HIT-like moAb (19), or a polyclonal anti-PF4 antibody (ABCAM™) for 1 hour at 37° C. NET digestion studies were carried out by infusing the channels with 100 U/ml DNase I, SIGMA-ALDRICH™) at 2 dynes/$cm^2$ after which the channels were washed with phosphate-buffered saline (PBS, GIBCO™) and fixed with 2% paraformaldehyde (BD Biosciences). To avoid laser-induced changes to the conformation of DNA (Drexler and Ruiz-Gomez, 2015), the inventors minimized laser exposure during their experiments. To account for this effect when studying whether KKO binding to PF4/NET complexes increased resistance to DNase, the inventors compared NET digestion by analyzing videos in which channels with and without KKO were included in the same visual field and exposed to UV light for the same amount of time. Channels were blocked with PBS with 2% bovine serum albumin (BSA, SIGMA-ALDRICH™), and PF4-NET complexes were visualized by incubating SYTOX-labeled NETs with a rabbit anti-human PF4 antibody at 37° C. for 1 hour, rinsing the channels with PBS flowed at 5 dynes/$cm^2$ for 5 minutes, and then incubating with a goat anti-rabbit secondary antibody (ABCAM™) at 37° C. for 1 hour. KKO was labeled with ALEXA FLUOR™ 647 (THERMO FISHER SCIENTIFIC™) prior to NET channel infusion. NET complexes were imaged with a ZEISS™ LSM 710 laser-scanning confocal microscope. Similar studies were done using 100 U/ml bacterial-derived micrococcal nuclease (New England Biolabs). Data were analyzed using ImageJ opensource image processing software (Schindelin et al., 2012).

Endothelialized channel microfluidic studies. Human umbilical vein endothelial cells (HUVECs, LONZA™) at passage 3-4 ($5\times10^6$ cells), were seeded onto fibronectin-coated (50 μg/ml, SIGMA-ALDRICH™) channels of 48-well BIOFLUX™ plates (Fluxion), allowed to adhere, and then cultured at 37° C. under 5% $CO_2$ in endothelial cell growth media (LONZA™) for 2-3 days to become confluent. HUVECs were incubated with TNFα (1-10 ng/ml) to simulate inflammation. Whole blood samples obtained from healthy human donors were fluorescently labeled with 2 mM calcein AM to visualize leukocytes and platelets and then incubated with KKO or the isoimmune control TRA (each 25 μg/ml) for 15 minutes. The samples were then recalcified with $CaCl_2$) (11 mM final concentration) and flowed through the channels at 5 dynes/$cm^2$. When using ImageJ to count endothelial-adherent cells, size exclusion thresholds were used to distinguish platelets from leukocytes. To assess KKO binding to TNFα-stimulated endothelium, the HUVEC-lined channels were infused with PBS containing PF4 (10 μg/ml) and KKO (25 μg/ml) conjugated with ALEXA FLUOR™ 488 (Invitrogen) at 5 dynes/$cm^2$. Following the infusion, the channels were washed with PBS and fixed with 2% paraformaldehyde (BD Biosciences). KKO binding was quantified based on fluorescent measurements obtained from a ZEISS™ LSM 710 laser scanning confocal microscope. Levels of KKO-endothelial binding were compared to those observed after the whole blood samples containing PF4 and KKO were infused through HUVEC channels that had been subjected to hematoporphyrin (50 μg/ml, Sigma Aldrich) photochemical injury, as the inventors' group has previously described (Hayes et al., 2017).

Femoral vein neutrophil rolling studies. HIT mice were anesthetized with nembutal and a skin flap extending from the ankle to thigh was removed to expose the femoral vein. SYTOX orange (2 nM) and $F(ab')_2$ fragments (0.2 mg/g mouse) directed against Ly6-G and CD41 were infused as 100 μl boluses via a catheter placed into the jugular vein to detect cfDNA, neutrophils, and platelets respectively. Confocal microscopy was used as described previously (Neyman et al., 2008) to obtain videos of neutrophil rolling and adhesion in the femoral vein at baseline and 10 minutes after 1 μg/g of KKO was infused via the jugular catheter. Data were collected and confocal time-lapsed images were analyzed using Slidebook 6.0 (Intelligent Imaging Innovations) to compare neutrophil behavior before and after KKO exposure.

Statistical analysis. Differences between 2 groups were compared using a 2-sided Student's t test with Welsh's correction or a Mann-Whitney U test. Normal distribution was tested using the D'Agostino & Pearson normality test. Differences between >2 groups were determined by one- or two-way ANOVA (as appropriate) and a Kruskall-Wallis test was performed when data was not normally distributed. Multiplicity corrected p values are reported for multiple comparisons. Statistical analyses were performed using MICROSOFT™ Excel 2011 and GRAPHPAD™ Prism 7.0 (GRAPHPAD™ Software). Differences were considered statistically significant when P values were ≤0.05.

Study approval. Animal procedures were approved by the Institutional Animal Care and Use Committee (IACUC) at CHOP in accordance with NIH guidelines and the Animal Welfare Act. Anonymized human blood was collected after signed, informed consent was provided by healthy donors, and approval for studies using human blood was obtained from CHOP's Human Review Board in accordance with Declaration of Helsinki Principles.

Antibodies and other labeled probes. KKO, the anti-PF4/heparin moAb, and TRA, a mouse $IgG^{2bK}$ isotype control moAb (Arepally et al., 2000), were purified from hybridoma supernatants. Anti-Fibrin 59D8 moAb was provided by Harmut Weiler of the Blood Center of Wisconsin (Reilly et al., 2001) PF4 was visualized using a polyclonal rabbit anti-human PF4 antibody (Ab9561, ABCAM™). A rabbit anti-citrullinated histone 3 (cit-H3, Ab5103, ABCAM™) was used to visualize citrullinated H3 and rabbit anti-myeloperoxidase antibody (MPO, EMD Millipore), was used to label NETs. Both of these antibodies were labeled for visualization with a goat anti-rabbit IgG H&L ALEXA FLUOR™ 594 (ab150080, ABCAM™). $F(ab')_2$ fragments of the anti-mouse CD41 moAb MWReg30 and of the anti-mouse Ly-6G antibody 1A8 (BD Biosciences) were used to detect murine platelets and neutrophils, respectively, in the cremaster laser injury model. HIT antibodies purified from patient plasma samples were visualized with an anti-human IgG Fc secondary antibody (eBioscience). All antibodies were either labeled using ALEXA FLUOR™ antibody-labeling kits according to manufacturer's instructions or species-appropriate ALEXA FLUOR™-conjugated secondary antibodies (all from THERMO FISHER SCIENTIFIC™). Extracellular DNA was visualized using SYTOX green or orange nucleic acid stain (THERMO FISHER SCIENTIFIC™)

Isolated human neutrophils. Human blood was collected after informed consent from healthy aspirin-free volunteers through a 19-gauge butterfly needle into 4 ml vacutainers coated with 7.2 mg of ethylenediaminetetraacetic acid (Becton Dickinson). Blood samples were stored at room temperature and used within 1 hour. Neutrophils were isolated with negative bead selection using the MACSXPRESS™ Neutrophil Isolation Kit (MILTENYI™ Biotec). The supernatant was collected and centrifuged at 300 g for 10 minutes, and the cell pellet was resuspended in 2 ml ammonium-chloride-potassium (ACK) lysing buffer (THERMO FISHER SCIENTIFIC™) for 5 minutes to lyse erythrocytes, after which the cells were washed with 10 ml of Hank's balanced salt solution (HBSS, THERMO FISHER SCIENTIFIC™), and then resuspended in HBSS containing calcium chloride (1.3 mM) and then manually counted, with trypan blue dye exclusion (GIBCO™) for cell viability.

Bioassay for NET digestion. PF4-induced NET resistance to digestion was quantified using a modified version of a previously described assay (Neyman et al., 2008). Isolated human neutrophils resuspended in HBSS, were stimulated with TNFα (1 ng/ml) for 5 minutes and transferred to a fibronectin coated (50 μg/ml) 96 well plate with $2\times10^5$ cells placed in each well. The samples were incubated with 100 nM of PMA ≥4 hours at 37° C. to stimulate NET release. NETs were incubated with PF4 (0-50 μg/ml)±KKO (25 μg/ml). Released cfDNA was labeled with SYTOX green (1 μM), and a baseline reading was obtained with fluorescence spectrometry, excitation 485 nm and emission 537 nm (SPECTRAMAX™ M2, MOLECULAR DEVICES™). The samples were then incubated with 1 U/mL DNase I (SIGMA-ALDRICH™) for 30 minutes at 37° C. and a repeat fluorescence reading was obtained. The percent original fluorescent intensity was measured for each well with higher values reflecting increased resistance to DNase I.

Glass slide NET compaction and digestion studies. To assess NET behavior without exposure to fibronectin, isolated human neutrophils resuspended in HBSS at a concentration of $2\times10^6$ cells/ml were allowed to settle on uncoated microscope cover glass slides (Fisherbrand) placed in a 24 well tissue-culture plate (Falcon) for 30 minutes at 37° C. The supernatant was aspirated and 500 μl of HBSS containing PF4 (0-50 μg/ml) was added to the wells and incubated at 37° C. for 1 hour. The supernatant was again aspirated and 500 μl of DNase I (100 U/ml) was added to the wells and incubated on a standard analog rocker (VWR™) at 37° C. for 1 hour. Images of the NETs before and after compaction and digestion were obtained with AXIO™ Observer Z1 inverted wide field microscope (ZEISS™) and data were analyzed using ImageJ open source image processing software (Schindelin et al., 2012).

Cremaster laser injury studies. Intravital microscopy was performed as described (2) using $Padi4^{+/+}$ and $Padi4^{-/-}$ HIT mice. Arterioles and venules of 20-40μ diameter were studied, and injury was induced with an SRS NL100 pulsed nitrogen dye laser (440 nm) focused on the vessel wall and pulsed until the vessels were perforated as indicated by the release of a small number of erythrocytes. Prior to injury induction, SYTOX green or orange (1 μM) and $F(ab')_2$ fragments (0.2 mg/g mouse) dissolved in phosphate buffered saline (PBS, GIBCO™) and infused as 100 μl boluses via a catheter placed into the jugular vein. After 1-3 injures were made, 1 μg/g of KKO or TRA was infused, and an additional 3-4 injuries were made with maximum experimental time per mouse being 2 hours. In some studies, the mice were treated with the CXCR2 antagonist SCH527123 (10 mg/kg, APEXBIO™) resuspended in distilled $H_2O$ with 5% dimethyl sulfoxide (SIGMA-ALDRICH™). In other studies, the mice were treated with an IV bolus of bovine pancrease-derived DNase 1 (100 U/mouse, SIGMA-ALDRICH™) suspended in PBS immediately prior to KKO injection and laser injury.

Widefield and confocal microscopy were performed as described previously (3). Data were collected and confocal time-lapsed images of platelet and neutrophil accumulation were analyzed using Slidebook 6.0 (Intelligent Imaging Innovations). Confocal Z-stacks were obtained immediately following injury at 5 minutes and again 60 minutes following KKO or TRA infusion. Data were analyzed with Slidebook 6.0 to measure platelet thrombus volumes.

Example 2—Results of PF4 and KKO in HIT

Enhanced neutrophil adhesion to the venular endothelium in HIT. Neutrophils are activated when exposed to PF4 and HIT antibodies (Xiao et al., 2008). To determine if this activation might impact neutrophil-endothelial cell interactions, the inventors infused calcein-AM labeled whole blood through HUVEC-lined microfluidic channels and quantified cell adhesion over time. The inventors observed scant leukocyte-endothelium adhesion in unstimulated channels that was unchanged by the addition of the HIT-like moAb KKO or the isotype control TRA (data not shown). However, when the HUVEC cells were pre-treated with TNFα, there was a two-fold increase in the number of adherent leukocytes in samples incubated with KKO, which induces the release of endogenous PF4 from platelets (Arepally et al., 2000), compared to samples treated with the isotype control TRA (FIGS. 1A-C). The inventors did not observe that TNFα treatment led to an increase in KKO binding to the HUVECs (FIG. 16) supporting that the increase in leukocyte adhesion seen in vivo was at least in part a result of leukocyte rather than endothelial activation. The inventors then asked if these findings could be recapitulated in vivo using a murine HIT model following injection of KKO (21). Within 30 minutes of KKO infusion, they observed increased neutrophil rolling and adhesion to uninjured cremaster muscle venules, but no neutrophil rolling or adhesion occurred in uninjured cremaster arterioles before or after the animals were exposed to KKO (FIGS. 1D-E). The inventors similarly observed an increase in neutrophil adhesion in the femoral vein 10 minutes following treatment with KKO (FIGS. 1F-G).

Enhanced neutrophil involvement in venular thrombosis in HIT. The inventors next asked whether exposure to HIT antibodies influences neutrophil incorporation into thrombi in vivo in the murine model of HIT. Cremaster vessels were injured at time 0 and adherent neutrophils and platelets were quantified at 5 minutes. The mice were then infused with KKO or TRA, and the thrombi were reexamined at 60 minutes. While there was an increase in platelet accumulation in arterioles following HIT induction, only a small number of neutrophils were incorporated into arteriolar thrombi, with a small but significant increase following treatment with KKO (FIG. 2). At sites of venular injury prior to HIT-induction, there was platelet and fibrin accumulation (FIG. 2B and FIG. 17, respectively) but only a small number of neutrophils adhered to these thrombi (FIGS. 2A and 2C). In contrast, following HIT induction, there was marked increase in neutrophil accumulation within venular thrombi (FIG. 2C) with a minimal change in fibrin accumulation (FIG. 17) and platelet volume (FIG. 2B). The rise in neutrophil accumulation was not observed following TRA infusion (FIGS. 2A-C).

A CXCR2-dependent retrograde migration of neutrophil into venular thrombi in HIT. To better understand the process of neutrophil accumulation in venular thrombi in HIT, the inventors induced laser injuries in venules following KKO infusion and monitored platelet and neutrophil accumulation in these lesions over 5 minutes. While platelets quickly adhered directly to the site of venous injury, most neutrophils initially bound to the endothelium 30-40 microns downstream of the injury (FIG. 3A). This finding is likely due to a combination of increased neutrophil adhesiveness induced by KKO exposure, documented in FIGS. 1A-E, in addition to activation of the endothelium downstream of cremaster laser injuries in HIT that the inventors have previously described (Hayes et al., 2017) These neutrophils subsequently migrated in a retrograde direction into the evolving thrombus (FIG. 3A) and 60 minutes following the initial injury, a significantly higher number of neutrophils were present in venular thrombi in mice exposed to KKO compared to those infused with the isotype control TRA (FIGS. 3A-B). The inventors hypothesized that retrograde migration of adherent neutrophils into the thrombi was induced by a chemoattractant released by activated platelets in the clots. Activated platelets release several chemokines from their a granules that cause neutrophil migration by engaging neutrophil surface CXCR2 (Chapman et al., 2007). To test whether the retrograde recruitment of neutrophils to venular thrombi in HIT was chemokine-dependent, the inventors treated the mice with the CXCR2 antagonist SCH527123 (Chapman et al., 2007) prior to the induction of HIT. They observed that thrombi in mice treated with SCH527123 before KKO infusion contained significantly fewer neutrophils within their thrombi (FIGS. 3A-B). Furthermore, these neutrophils were located at the periphery of the platelet-rich thrombi and not embedded within them.

In vitro studies of PF4-NET interactions. After observing marked HIT-induced neutrophil infiltration in venular thrombi, the inventors hypothesized that adherent neutrophils contribute to venous thrombi in HIT, in part, through the release of NETs, as described in deep venous thrombosis (Brill et al., 2012). Moreover, platelet activation, one of the hallmarks of HIT, can initiate NETosis in inflammatory states (Jenne et al., 2013; McDonald et al., 2012). Activated platelets release high levels of PF4, which forms high-molecular weight aggregates with various polyanions, producing antigens that are recognized by HIT antibodies (Cines et al., 2007). The inventors postulated that when PF4 is released in HIT, due to its cationic charge, it will bind to cfDNA present in NETs and impact NET biology. To investigate PF4-NET interactions in real time, the inventors studied neutrophils adherent to fibronectin-coated microfluidic channels stimulated with PMA to release NETs. They confirmed that these cfDNA structures were NETs by using co-immunofluorescent staining to show that they contained citrullinated histones and MPO (not shown). The NET-lined channels were then infused at venular flow rates with buffer containing PF4 at concentrations readily attained at sites of platelets activation (5-100 μg/ml) (Xiao et al., 2008). Prior to exposure to PF4, NETs labeled with SYTOX were round and transparent, with a cloud like appearance that the inventors termed "fluffy". When infused with Hanks' Balanced Salt Solution (HBSS, THERMO FISHER SCIENTIFIC™), or human plasma, the NETs extended, and when flow was stopped they rebounded to their former shape. Following treatment with either buffer or plasma containing PF4, the NETs became opaque and narrow with a sharply tapered tail that did not change shape when flow was stopped. (FIG. 4A). Maximum compaction, with a 50% reduction in NET area, was achieved when the NETs were flowed with HBSS containing PF4 concentrations of ≥10 μg/ml (FIG. 4B, left, for PF4≤25 μg/ml and not shown for >25 μg/ml). Confocal imaging of the compacted NETs, labeled with an anti-PF4 antibody and a fluorophore-conjugated secondary antibody, confirmed that PF4 bound to these structures (FIG. 4A). Total NET DNA content measured by fluorescence intensity was preserved following PF4 infusion, excluding the possibility that the compacted NET appearance was due to the dissolution of DNA (FIG. 4B, right). Co-immunofluorescent studies of NETs following PF4 infusion demonstrated that compaction does not lead to displacement of citrullinated histones or MPO (not shown).

The inventors next asked whether PF4-induced changes in NET morphology could impact NET behavior. While PF4-free NETs were highly susceptible to DNase I at a concentration of 100 U/ml, with near complete digestion in <2 minutes, PF4-bound NETs were resistant to DNase I, with near-complete protection at PF4 concentrations of ≥10 μg/ml (FIGS. 4C-D). The infusion of human plasma containing PF4 was also found to confer resistance to DNase I-mediated digestion (not shown) and similar results were observed with the use of bacterial-derived micrococcal nuclease (not shown). Comparable nuclease resistance was also observed in a static system not coated with fibronectin, showing that fibronectin, which has a DNA binding domain and is known to interact with NETs (Monti et al., 2017), is not the cause of the observed changes in NET behavior (not shown).

Previous in vitro studies reported that NETs are degraded by exposure to heparin (Fuchs et al., 2010), suggesting that NETs should be reduced in patients with recent heparin exposure. The inventors found that at a therapeutic concentration of 0.4 U/ml (Brill-Edwards et al., 1993) or at a supratherapeutic concentration of 5000 U/ml, heparin did not degrade NETs in their microfluidic system; however, they observed that exposure to heparin, reversed compaction with restoration of fluffy morphology (not shown). Confocal imaging of NETs labeled with a polyclonal anti-PF4 antibody confirmed that heparin treatment removed PF4 from the NETs (not shown), and DNase I infusion studies confirmed that decompaction of NETs restored their susceptibility to endonuclease digestion (not shown). However, when NETs were exposed to a 25 μg/ml instead of 10 μg/ml of PF4, a concentration still within the range typically observed at sites of thrombosis (Rauova et al., 2006), NET compaction and DNase resistance were maintained during co-infusion with therapeutic concentrations of heparin (not shown).

In vitro effects of HIT antibodies on PF4-NET complexes. PF4 has previously been shown to form complexes with DNA aptamers that are HIT antigenic targets (Jaax et al., 2013). The inventors therefore examined whether PF4-NET complexes are also recognized by KKO and IgG isolated from HIT patient plasma using the microfluidic chambers to assess binding and function. The inventors found that KKO and HIT IgG suspended in HBSS did not interact with non-compacted NETs, but both bound to PF4-NET complexes (FIG. 5A). KKO dissolved in human plasma also bound specifically to PF4-NET complexes (not shown). Antibody binding did not induce greater NET compaction, but it enhanced resistance to DNase I digestion (FIG. 5B). This effect was found to be specific to HIT antibodies, as incubation with a polyclonal anti-PF4 antibody at 25 μg/ml did not provide similar protection from endonucleases (FIGS. 5C-D). Similar results were seen using NETs immobilized to fibronectin-coated 96-well plates (FIG. 5E) (Hakkim et al., 2010).

Thrombosis in the HIT murine model in the presence or absence of PAD4. The inventors then asked whether enhanced NET endonuclease resistance and the formation of PF4-NET-HIT antibody complexes, observed in vitro, contribute to in vivo thrombus development in the murine model of HIT. The inventors hypothesized that the release of NETs by thrombus-adherent neutrophils and their subsequent modification by PF4 and HIT antibodies may play a role in the prothrombotic state that develops in these animals. To better understand the way in which NETosis may contribute to thrombosis in HIT, the inventors studied $Padi4^{-/-}$/HIT mice that are incapable of releasing NETs (FIGS. 15A-C). Previous studies have shown that Padi4 knockout mice do not release NETs and are protected from venous thrombosis (Brill et al., 2012). Following KKO injection, the severity of thrombocytopenia in $Padi4^{-/-}$/HIT mice was comparable to that seen in $Padi4^{+/+}$/HIT controls. (FIG. 6A) The size of arteriolar thrombi following laser injury was unaffected by PAD4 deficiency (FIG. 6B) and neutrophil incorporation into venule thrombi following TRA injection was similar in $Padi4^{-/-}$ and $Padi4^{+/+}$ HIT mice. However, after KKO injection, the $Padi4^{-/-}$/HIT mice developed smaller venular thrombi following injury (FIGS. 6C-D) with incorporation of fewer neutrophils (FIG. 6E). This difference became more pronounced with the passage of time (FIG. 6C). Consistent with these studies in $Padi4^{-/-}$ HIT mice, $Padi4^{+/+}$ HIT mice treated with DNase I prior to KKO infusion, had a significant decrease in platelet thrombus volume 60 minutes following injury (FIG. 6C), suggesting that NETs play a role in thrombus growth and stabilization in this model.

Clinical indication of NETosis in HIT. It has been reported that circulating MPO levels are elevated in HIT (Khairy et al., 2004), potentially implicating neutrophils and NETosis in the pathobiology of HIT. The inventors confirmed this clinical finding comparing cfDNA and MPO-DNA complex levels in samples from patients at high- or at low-likelihood of having HIT (Cuker, A., 2012), healthy controls, and patients with immune-thrombocytopenia (ITP). Cell free DNA (not shown) and MPO-DNA complex levels (not shown) were significantly higher in individuals diagnosed with HIT compared to healthy controls and patients with an alternative cause of immune thrombocytopenia. Although there was a trend toward higher MPO-DNA complex levels in HIT patients compared to ill patients evaluated for HIT but found to have a low probability of having the disease, this finding did not reach statistical significance (p=0.1), demonstrating that cfDNA release and NETosis occur in multiple proinflammatory/prothrombotic states that commonly occur in hospitalized patients.

PF4 in improving outcome in LPS-induced endotoxemia in PF4-deficient $Cxcl4^{-/-}$ mice. The inventors previously published that PF4 is protective from mortality in LPS endotoxemia but had proposed that it was related to increased levels of activated Protein C levels (Kowalska et al., Blood, 2007). They now show that PF4 expression is also associated with decreased circulating levels of NDPs (MPO, histones and cfDNA (not shown). Moreover, treatment of $Cxcl4^{-/-}$ mice with exogenous PF4 either delivered by osmotic pump (OP) or intravenously (IV) also leads to decreased plasma levels of NDPs (not shown).

Use of KKO as a therapeutic agent in LPS-induced endotoxemia model. The Investigators posited that in most patients with sepsis significant amounts of PF4 will have already been released from activated platelets on patient presentation so that infused PF4 would not be very effective, but that cross-linking of the released NETs by an antibody like KKO may be effective if Fc-related sequelae can be avoided. The Investigator attempted to remove the Fc portion of KKO but were unable to cleave the molecule because it is an IgG2bκ isotype and instead deglycosylated the Fc portion of KKO as this partially decreases Fc-related biology. Healthy donor whole blood was incubated with KKO or DG-KKO. This ordinarily activates the platelets via released PF4 from the platelets that bind to the platelet surface with subsequent KKO binding and activation of the platelets via the FcγRIIA receptor. The activated platelets degranulate releasing more PF4 and a cyclical pattern leads to significant platelet activation as measured by surface P-selectin expression. The DG-KKO clearly was markedly less active in this assay consistent with loss of Fc-related activity (data not shown).

Deglycosylated KKO. The Investigators then wondered if KKO might be able to stabilize NETs in LPS-induced endotoxemic mice and infused DG-KKO into mice that expressed only hPF4 (as KKO only binds to human and not mice PF4 in the presence of heparin or another polyanion). Not shown is that $hPF4^{+}$ mice treated with DG-KKO are resistant to NDP release post-LPS exposure. Additionally, DG-KKO almost completely prevents the thrombocytopenia typically seen in the LPS-treated mice model. Moreover, not shown is that unlike DG-TRA, DG-KKO extends the lifespan of LPS-treated hPF4+ mice significantly.

Example 3—Discussion of PF4 and KKO in HIT

Over the past several years, it has become increasingly clear that the pathophysiology of HIT extends beyond platelet activation. It has previously been shown that HIT antibody interaction with other cells types including the endothelium (Hayes et al., 2017) and monocytes (Rauova et al., 2010), leads to cell activation and a prothrombotic state. Others have also demonstrated that HIT antibodies activate PF4-exposed neutrophils through their FcγRIIa receptors, leading to increased expression of Mac-1 on the cell surface and enhanced neutrophil aggregate formation (Xiao et al., 2008). In this report, the inventors explore specific pathways by which neutrophils may contribute to thrombosis in HIT and propose that they do so through multiple steps including the stimulation of neutrophil adhesion to inflamed endothelium, the promotion of neutrophil migration into venular thrombi, and the formation of antigenic PF4-NET-HIT antibody complexes.

The basis for enhanced binding of HIT-activated neutrophils to the endothelium in large vessels and the microcirculation requires further exploration. Prior studies have shown that HIT antibody exposure increases neutrophil surface expression of Mac-1 (Xiao et al., 2008).

Endothelial cells are also activated by PF4 and HIT antibodies, increasing surface expression of P- and E-selectins (Blank et al., 2002). The inventors' finding of enhanced in vitro neutrophil binding parallels the increased adhesion seen in vivo in the setting of the inventors' murine model of HIT, with or without endothelial cell injury. They speculate that neutrophil adhesion immediately downstream of growing venular injury may be due to increased turbulent flow around larger thrombi, that is known to enhance neutrophil adhesion to the endothelial lining (Begandt et al., 2017). It may also be due to the release of PF4 from activated platelets within the thrombus that results in increased assembly of antigenic complexes on the downstream endothelium, leading to more HIT antibody binding and endothelial activation (Hayes et al., 2017). The role of each of these mechanisms in the accumulation of neutrophils in injured venules requires additional investigation to identify opportunities for intervention.

After adhering to the endothelium downstream of thrombosis, many neutrophils migrate in a retrograde manner and are incorporated into the venular clots. Retrograde migration may occur in response to a chemotactic gradient emanating from degranulating platelets. A similar process termed "directed intravascular migration" has been described in ischemia-reperfusion injuries, in which degranulating platelets release CXCL7 (neutrophil activating peptide 2 (NAP2)) and CXCL5 (epithelial-derived neutrophil-activating peptide 78 (ENA-78)), leading to CXCR2-dependent neutrophil recruitment (Ghasemzadeh et al., 2013). The retrograde migration that the inventors observed in venular HIT thrombi is also similar to "neutrophil-swarming," a process in which large numbers of neutrophils rapidly accumulate at sites of infection or sterile injury where they release NETs (Kienle and Lammermann, 2016). In support of this hypothesis, the inventors show that the retrograde migration of neutrophils into venous thrombi can be abrogated with the blockade of CXCR2. Whether NAP2 and/or ENA-78, both released from platelets and bound by CXCR2 (Chapman et al., 2009), contribute to the chemogradient remains to be determined. Further investigation needs to be done to ascertain if this pattern of adhesion occurs in other prothrombotic disorders associated with venous thrombosis.

Many groups have proposed that NET release links neutrophil accumulation to thrombus progression (Brill et al., 2012; Wolach et al., 2018; Dyer et al., 2018). The inventors posit that NETs released in HIT are uniquely prothrombotic because the binding of PF4 and HIT antibodies causes them to become immunogenic. Previous studies have shown that nucleic acid binding leads to the exposure of the same antigenic epitopes present on PF4/heparin complexes (Jaax et al., 2013) Mice injected with PF4/nucleic acid complexes develop antibodies that cross-reacted with PF4/heparin complexes (Jaax et al., 2013). The inventors' microfluidic channel experiments support that PF4 forms complexes with chromatin DNA in the same way as PF4 binds heparin to form macroaggregates (Brandt et al., 2015). These studies showing that HIT IgG isolated from human plasma binds to these PF4-NET complexes, confirms that they contain HIT antigenic epitopes.

In addition to producing HIT antigenic complexes, the inventors have observed that PF4 binding leads to chromatin compaction that causes NETs to become DNase resistant. It has previously been shown that NET binding to the cationic peptide LL-37 leads to enhanced protection from nuclease digestion (Neumann et al., 2014), in a manner similar to what the inventors have observed with PF4. While DNase-resistant NETs may have increased antimicrobial activity, impaired NET degradation has been implicated in the pathogenesis of autoimmune diseases, including anti-phospholipid antibody syndrome and lupus (Leffler et al., 2012; Lewis et al., 2015). In these disorders, DNase resistance is thought to occur due to the development of anti-NET immunoglobulins that interfere with DNase binding to cfDNA. (Hakkim et al., 2010) In HIT, PF4 forms complexes with NETs that are bound by HIT antibodies that provide additional protection from DNases. These stable, compacted PF4-NET-HIT IgG aggregates then serve as a Fc-rich surface that can recruit and activate circulating hematopoietic cells via their FcγRIIa receptors and activate the complement cascade (Qiao et al., 2015).

To test this hypothesis, the inventors generated Padi4$^{-/-}$ HIT mice that do not undergo NETosis (Li et al., 2010; Brill et al., 2012; Lewis et al., 2015). In these animals, venular thrombi generated after HIT induction are markedly smaller than those observed in animals capable of NET release, with fewer incorporated neutrophils and decreased platelet volumes. This suggests that NETs contribute to the early stages of venule thrombus growth, enhancing both platelet accumulation and neutrophil recruitment. This effect was not observed in laser injury-induced arteriole thrombi, which have little neutrophil infiltration irrespective of PAD4 activity. Moreover, the loss of PAD4 activity—and likely NET formation—did not affect the severity of thrombocytopenia in HIT mice, suggesting that the development of venular thrombi is unrelated to the mechanism underlying the development of thrombocytopenia.

The inventors next treated HIT mice with DNase prior to cremaster laser injury to determine if NETs functionally contribute to thrombus formation in their model and found that this led to a significant decrease in cremaster venule thrombus platelet volumes. This finding further supports the inventors' hypothesis that NETs play a role in thrombus growth and stabilization in this model. However unlike in the Padi4$^{-/-}$/HIT mice, the number of thrombus-adherent neutrophils did not fall in accordance with the decrease in platelet volumes. This difference may occur because Padi4$^{-/-}$ mice never release NETs, whereas PF4-compacted NETs are incompletely degraded by DNase and may still expose PF4-NET-HIT IgG aggregates that can recruit circulating neutrophils. Nonetheless, the decrease in venular thrombus size raises the possibility that DNase treatment may be effective in preventing the venular prothrombotic state in HIT.

The inventors posited that these insights gained from studies of PF4 interaction with NETs in HIT as well as the interaction of HIT-like antibodies with PF4-NET complexes would translate into new therapeutics for sepsis. The inventors proposed that drugs that either directly compact NETs, protecting them from lysis (e.g., PF4) or drugs (e.g., DG-KKO) that indirectly bind to NETs via intermediate complexes (e.g., PF4-NETs) may prevent massive NET lysis in sepsis and decrease release of sequestered NDP products, both activities—the stabilization of NETs and the sequestering of NDPs—may be required for efficacy in preventing deleterious sequelae, including death, in sepsis. In vitro and murine in vivo LPS-endotoxemic studies support the application of these new therapeutics in sepsis.

References for Examples 1-3

The following references, to the extent that they provide exemplary procedural or other details supplementary to those set forth herein, are specifically incorporated herein by reference.

Nand S, Wong W, Yuen B, Yetter A, Schmulbach E, Gross Fisher S. Heparin-induced thrombocytopenia with thrombosis: incidence, analysis of risk factors, and clinical outcomes in 108 consecutive patients treated at a single institution. Am J Hematol. 1997; 56(1):12-6.

Wallis D E, Workman D L, Lewis B E, Steen L, Pifarre R, Moran J F. Failure of early heparin cessation as treatment for heparin-induced thrombocytopenia. Am J Med. 1999; 106(6):629-35.

Kelton J G, Hursting M J, Heddle N, Lewis B E. Predictors of clinical outcome in patients with heparin-induced thrombocytopenia treated with direct thrombin inhibition. Blood Coagul Fibrinolysis. 2008; 19(6):471-5.

Linkins L A, Dans A L, Moores L K, Bona R, Davidson B L, Schulman S, et al. Treatment and prevention of heparin-induced thrombocytopenia: Antithrombotic Therapy and Prevention of Thrombosis, 9th ed: American College of Chest Physicians Evidence-Based Clinical Practice Guidelines. Chest. 2012; 141(2 Suppl):e495S-530S.

Zhou A, Winkler A, Emamifar A, Gartland B, Duncan A, Antun A, et al. Is the incidence of heparin-induced thrombocytopenia affected by the increased use of heparin for VTE prophylaxis? Chest. 2012; 142(5):1175-78.

Cervera R. Antiphospholipid syndrome. Thromb Res. 2017; 151 Suppl 1:S43-S7.

Donze J D, Ridker P M, Finlayson S R, Bates D W. Impact of sepsis on risk of postoperative arterial and venous thromboses: large prospective cohort study. BMJ. 2014; 349:g5334.

Rauova L, Zhai L, Kowalska M A, Arepally G M, Cines D B, Poncz M. Role of platelet surface PF4 antigenic complexes in heparin-induced thrombocytopenia pathogenesis: diagnostic and therapeutic implications. Blood. 2006; 107(6):2346-53.

Rauova L, Arepally G, McKenzie S E, Konkle B A, Cines D B, Poncz M. Platelet and monocyte antigenic complexes in the pathogenesis of heparin-induced thrombocytopenia (HIT). J Thromb Haemost. 2009; 7 Suppl 1:249-52.

Rauova L, Hirsch J D, Greene T K, Zhai L, Hayes V M, Kowalska M A, et al. Monocyte-bound PF4 in the pathogenesis of heparin-induced thrombocytopenia. Blood. 2010; 116(23):5021-31.

Hayes V, Johnston I, Arepally G M, McKenzie S E, Cines D B, Rauova L, et al. Endothelial antigen assembly leads to thrombotic complications in heparin-induced thrombocytopenia. J Clin Invest. 2017; 127(3):1090-8.

Arepally G M. Heparin-induced thrombocytopenia. Blood. 2017; 129(21):2864-72.

Poncz M. Mechanistic basis of heparin-induced thrombocytopenia. Semin Thorac Cardiovasc Surg. 2005; 17(1):73-9.

Xiao Z, Visentin G P, Dayananda K M, Neelamegham S. Immune complexes formed following the binding of anti-platelet factor 4 (CXCL4) antibodies to CXCL4 stimulate human neutrophil activation and cell adhesion. Blood. 2008; 112(4):1091-100.

Qiao J, Al-Tamimi M, Baker R I, Andrews R K, Gardiner E E. The platelet Fc receptor, FcgammaRIIa. Immunol Rev. 2015; 268(1):241-52. Mayadas T N, Tsokos G C, Tsuboi N. Mechanisms of immune complex-mediated neutrophil recruitment and tissue injury. Circulation. 2009; 120(20): 2012-24.

Khairy M, Lasne D, Amelot A, Crespin M, Rendu F, Aiach M, et al. Polymorphonuclear leukocyte and monocyte activation induced by plasma from patients with heparin-induced thrombocytopenia in whole blood. Thromb Haemost. 2004; 92(6):1411-9. Martinod K, Wagner D D. Thrombosis: tangled up in NETs. Blood. 2014; 123(18): 2768-76.

Arepally G M, Kamei S, Park K S, Kamei K, Li Z Q, Liu W, et al. Characterization of a murine monoclonal antibody that mimics heparin-induced thrombocytopenia antibodies. Blood. 2000; 95(5):1533-40.

Li P, Li M, Lindberg M R, Kennett M J, Xiong N, Wang Y. PAD4 is essential for antibacterial innate immunity mediated by neutrophil extracellular traps. J Exp Med. 2010; 207(9):1853-62.

Reilly M P, Taylor S M, Hartman N K, Arepally G M, Sachais B S, Cines D B, et al. Heparin-induced thrombocytopenia/thrombosis in a transgenic mouse model requires human platelet factor 4 and platelet activation through FcgammaRIIA. Blood. 2001; 98(8):2442-7.

Kowalska M A, Rauova L, Poncz M. Role of the platelet chemokine platelet factor 4 (PF4) in hemostasis and thrombosis. Thromb Res. 2010; 125(4):292-6.

Eslin D E, Zhang C, Samuels K J, Rauova L, Zhai L, Niewiarowski S, et al. Transgenic mice studies demonstrate a role for platelet factor 4 in thrombosis: dissociation between anticoagulant and antithrombotic effect of heparin. Blood. 2004; 104(10):3173-80.

Zhang C, Thornton M A, Kowalska M A, Sachis B S, Feldman M, Poncz M, et al. Localization of distal regulatory domains in the megakaryocyte-specific platelet basic protein/platelet factor 4 gene locus. Blood. 2001; 98(3):610-7.

Cong L, Zhang F. Genome engineering using CRISPR-Cas9 system. Methods Mol Biol. 2015; 1239:197-217.

Doench J G, Fusi N, Sullender M, Hegde M, Vaimberg E W, Donovan K F, et al. Optimized sgRNA design to maximize activity and minimize off-target effects of CRISPR-Cas9. Nat Biotechnol. 2016; 34(2):184-91.

Cuker A, Arepally G, Crowther M A, Rice L, Datko F, Hook K, et al. The HIT Expert Probability (HEP) Score: a novel pre-test probability model for heparin-induced thrombocytopenia based on broad expert opinion. J Thromb Haemost. 2010; 8(12):2642-50.

Cuker A. Clinical and laboratory diagnosis of heparin-induced thrombocytopenia: an integrated approach. Semin Thromb Hemost. 2014; 40(1):106-14.

Arepally G, Reynolds C, Tomaski A, Amiral J, Jawad A, Poncz M, et al. Comparison of PF4/heparin ELISA assay with the 14C-serotonin release assay in the diagnosis of heparin-induced thrombocytopenia. Am J Clin Pathol. 1995; 104(6):648-54.

Lambert M P, Gernsheimer T B. Clinical updates in adult immune thrombocytopenia. Blood. 2017; 129(21):2829-35.

Tutwiler V, Madeeva D, Ahn H S, Andrianova I, Hayes V, Zheng X L, et al. Platelet transactivation by monocytes promotes thrombosis in heparin-induced thrombocytopenia. Blood. 2016; 127(4):464-72.

Sachais B S, Litvinov R I, Yarovoi S V, Rauova L, Hinds J L, Rux A H, et al. Dynamic antibody-binding properties in the pathogenesis of HIT. Blood. 2012; 120(5):1137-42.

Drexler G A, Ruiz-Gomez M J. Microirradiation techniques in radiobiological research. J Biosci. 2015; 40(3):629-43.

Schindelin J, Arganda-Carreras I, Frise E, Kaynig V, Longair M, Pietzsch T, et al. Fiji: an open-source platform for biological-image analysis. Nat Methods. 2012; 9(7):676-82.

Neyman M, Gewirtz J, Poncz M. Analysis of the spatial and temporal characteristics of platelet-delivered factor VIII-based clots. Blood. 2008; 112(4):1101-8.

Chapman R W, Minnicozzi M, Celly C S, Phillips J E, Kung T T, Hipkin R W, et al. A novel, orally active CXCR1/2 receptor antagonist, Sch527123, inhibits neutrophil recruitment, mucus production, and goblet cell hyperplasia in animal models of pulmonary inflammation. J Pharmacol Exp Ther. 2007; 322(2):486-93.

Brill A, Fuchs T A, Savchenko A S, Thomas G M, Martinod K, De Meyer S F, et al. Neutrophil extracellular traps promote deep vein thrombosis in mice. J Thromb Haemost. 2012; 10(1):136-44.

Jenne C N, Urrutia R, Kubes P. Platelets: bridging hemostasis, inflammation, and immunity. Int J Lab Hematol. 2013; 35(3):254-61.

McDonald B, Urrutia R, Yipp B G, Jenne C N, Kubes P. Intravascular neutrophil extracellular traps capture bacteria from the bloodstream during sepsis. Cell Host Microbe. 2012; 12(3):324-33.

Cines D B, Rauova L, Arepally G, Reilly M P, McKenzie S E, Sachais B S, et al. Heparin-induced thrombocytopenia: an autoimmune disorder regulated through dynamic autoantigen assembly/disassembly. J Clin Apher. 2007; 22(1):31-6.

Monti M, Iommelli F, De Rosa V, Carriero M V, Miceli R, Camerlingo R, et al. Integrin-dependent cell adhesion to neutrophil extracellular traps through engagement of fibronectin in neutrophil-like cells. PLoS One. 2017; 12(2):e0171362.

Fuchs T A, Brill A, Duerschmied D, Schatzberg D, Monestier M, Myers D D, Jr., et al. Extracellular DNA traps promote thrombosis. Proc Natl Acad Sci USA. 2010; 107(36):15880-5.

Brill-Edwards P, Ginsberg J S, Johnston M, Hirsh J. Establishing a therapeutic range for heparin therapy. Ann Intern Med. 1993; 119(2):104-9.

Jaax M E, Krauel K, Marschall T, Brandt S, Gansler J, Furll B, et al. Complex formation with nucleic acids and aptamers alters the antigenic properties of platelet factor 4. Blood. 2013; 122(2):272-81.

Hakkim A, Furnrohr B G, Amann K, Laube B, Abed U A, Brinkmann V, et al. Impairment of neutrophil extracellular trap degradation is associated with lupus nephritis. Proc Natl Acad Sci USA. 2010; 107(21):9813-8.

Cuker A. Update in the diagnosis and management of heparin-induced thrombocytopenia. Clin Adv Hematol Oncol. 2012; 10(7):453-5.

Blank M, Shoenfeld Y, Tavor S, Praprotnik S, Boffa M C, Weksler B, et al. Anti-platelet factor 4/heparin antibodies from patients with heparin-induced thrombocytopenia provoke direct activation of microvascular endothelial cells. Int Immunol. 2002; 14(2):121-9.

Begandt D, Thome S, Sperandio M, Walzog B. How neutrophils resist shear stress at blood vessel walls: molecular mechanisms, subcellular structures, and cell-cell interactions. J Leukoc Biol. 2017; 102(3):699-709.

Ghasemzadeh M, Kaplan Z S, Alwis I, Schoenwaelder S M, Ashworth K J, Westein E, et al. The CXCR1/2 ligand NAP-2 promotes directed intravascular leukocyte migration through platelet thrombi. Blood. 2013; 121(22):4555-66.

Kienle K, Lammermann T. Neutrophil swarming: an essential process of the neutrophil tissue response. Immunol Rev. 2016; 273(1):76-93.

Chapman R W, Phillips J E, Hipkin R W, Curran A K, Lundell D, Fine J S. CXCR2 antagonists for the treatment of pulmonary disease. Pharmacol Ther. 2009; 121(1):55-68.

Wolach O, Sellar R S, Martinod K, Cherpokova D, McConkey M, Chappell R J, et al. Increased neutrophil extracellular trap formation promotes thrombosis in myeloproliferative neoplasms. Sci Transl Med. 2018; 10(436).

Dyer M R, Chen Q, Haldeman S, Yazdani H, Hoffman R, Loughran P, et al. Deep vein thrombosis in mice is regulated by platelet HMGB1 through release of neutrophil-extracellular traps and DNA. Sci Rep. 2018; 8(1): 2068.

Brandt S, Krauel K, Jaax M, Renne T, Helm C A, Hammerschmidt S, et al. Polyphosphates form antigenic complexes with platelet factor 4 (PF4) and enhance PF4-binding to bacteria. Thromb Haemost. 2015; 114(6):1189-98.

Neumann A, Vollger L, Berends E T, Molhoek E M, Stapels D A, Midon M, et al. Novel role of the antimicrobial peptide LL-37 in the protection of neutrophil extracellular traps against degradation by bacterial nucleases. J Innate Immun. 2014; 6(6):860-8.

Leffler J, Stojanovich L, Shoenfeld Y, Bogdanovic G, Hesselstrand R, Blom A M. Degradation of neutrophil extracellular traps is decreased in patients with antiphospholipid syndrome. Clin Exp Rheumatol. 2014; 32(1):66-70.

Leffler J, Martin M, Gullstrand B, Tyden H, Lood C, Truedsson L, et al. Neutrophil extracellular traps that are not degraded in systemic lupus erythematosus activate complement exacerbating the disease. J Immunol. 2012; 188(7):3522-31.

Lewis H D, Liddle J, Coote J E, Atkinson S J, Barker M D, Bax B D, et al. Inhibition of PAD4 activity is sufficient to disrupt mouse and human NET formation. Nat Chem Biol. 2015; 11(3):189-91.

Holz O, Khalilieh S, Ludwig-Sengpiel A, Watz H, Stryszak P, Soni P, et al. SCH527123, a novel CXCR2 antagonist, inhibits ozone-induced neutrophilia in healthy subjects. Eur Respir J. 2010; 35(3):564-70.

Swamydas M, Lionakis M S. Isolation, purification and labeling of mouse bone marrow neutrophils for functional studies and adoptive transfer experiments. J Vis Exp. 2013(77):e50586.

Celi A, Merrill-Skoloff G, Gross P, Falati S, Sim D S, Flaumenhaft R, et al. Thrombus formation: direct real-time observation and digital analysis of thrombus assembly in a living mouse by confocal and widefield intravital microscopy. J Thromb Haemost. 2003; 1(1):60-8.

Neyman M, Gewirtz J, Poncz M. Analysis of the spatial and temporal characteristics of platelet-delivered factor VIII-based clots. Blood. 2008; 112(4):1101-8.

Fuchs T A, Brill A, Duerschmied D, Schatzberg D, Monestier M, Myers D D, Jr., et al. Extracellular DNA traps promote thrombosis. Proc Natl Acad Sci USA. 2010; 107(36):15880-5.

Example 4—Introduction to PF4 and DG-KKO in Sepsis

Examples 1-3 set the groundwork for the inventor's proposed use of PF4 and a modified version of the HIT-like pathogenic antibody KKO in sepsis. Sepsis is a dysregulated response to infection that leads to life-threatening organ damage. It affects millions of people each year and remains one of the most common causes of mortality worldwide (Angus et al., 2001; Mayr et al., 2014). Care consists of antibiotics and supportive measures (Coopersmith et al., 2018a), but these interventions do not target the host response that causes much of the morbidity in sepsis (Jackson et al., 2019), and the poor survival rate has not changed significantly for several decades (Gyawali et al., 2019). New emphasis is being placed on the identification of novel targeted interventions (Coopersmith et al., 2018b) and the innate immune response has become an area of great interest (Delano and Ward, 2016). Neutrophils, the most abundant circulating white blood cell (Kubes, P., 2018), play a crucial role in sepsis. They are recruited to inflamed vessels where they release NETs, webs of negatively charged cfDNA complexed with positively-charged histones and antimicrobial proteins, such as MPO and NE, that ensnare pathogens, limit bacterial spread (McDonald et al., 2012), and degrade inflammatory cytokines (Schauer et al., 2014; Mahajan et al., 2019). However, these positive effects occur at the expense of collateral tissue damage. NETs are lysed by circulating DNases (Jimenez-Alcazar et al., 2017), releasing NDPs that exert harmful effects. For example, cfDNA triggers the contact-pathway (Bhagirath et al., 2015) and fixes complement (Leffler et al., 2012), MPO induces oxidative tissue damage (Tian et al., 2017), NE cleaves tissue factor pathway inhibitor (TFPI) promoting thrombosis (Massberg et al., 2010), while histones cause platelet activation (Esmon, CT, 2011) and are toxic to endothelial cells (Xu et al., 2009). In septic patients, plasma levels of NDPs correlate with end-organ damage and mortality (Maruchi et al., 2018; Colon et al., 2019). It has been suggested that preventing NETosis might be beneficial Martinod et al., 2015), but the inventors believe that this strategy may be ineffective as septic patients likely have a large amount of NETs formed by the time they become clinically ill. The use of DNase I to accelerate NET degradation has been proposed as a therapeutic intervention (McDonald et al., 2017). However, results of prior studies with this intervention have been mixed (O'Brien et al., 2017), raising the concern that DNase I treatment may induce harm through the release of entrapped bacteria and NDPs (McDonald et al., 2012; Schauer et al., 2014; Mai et al., 2015) causing the symptoms of a Jarisch-Herxheimer reaction (Hurley, J C, 1995).

The inventors propose an alternative strategy of NET-directed therapy in sepsis, in which NETs are compacted and stabilized, leading to both enhanced bacterial entrapment and NDP sequestration. Platelet factor 4 (PF4, CXCL4), a positively-charged chemokine that accounts for approximately 2-3% of total protein found in circulating platelets (Eslin et al., 2004), may exert these effects. When platelets are activated, PF4 is released in concentrations that exceed 12 μg/ml in the vicinity of injury (Eslin et al., 2004). Although high-levels of PF4 have been identified in the α-granules of every examined mammalian species, suggesting that it serves a crucial function, its role remains unclear. Due to its strong positive charge, PF4 binds to and aggregates polyanions like heparin (Cines et al., 2007). The inventors had found that PF4 similarly aggregates NETs, physically compacting them (Cines et al., 2007), enhancing their resistance to endogenous and microbial nucleases (Lande et al., 2019), while markedly increasing bacterial entrapment. They speculated that these activities may significantly contribute to the inventors' previous observation that PF4-deficient mice (cxcl4$^{-/-}$) have increased mortality in LPS endotoxemia, whereas animals that overexpress hPF4$^{+}$ have improved survival (Kowalska et al., 2007). These findings suggest that PF4's protective role in sepsis may be the evolutionary force driving its conserved expression.

KKO is a moAb directed against hPF4-heparin complexes that induces thrombocytopenia and a prothrombotic state when injected into mice that express hPF4 and FcγRIIA, mimicking the clinical disorder heparin-induced thrombocytopenia (HIT) (Arepally et al., 2000). KKO binds hPF4-NET complexes, further enhancing DNase resistance (Gollomp et al., 2018). The inventors now speculate that treatment with an Fc-modified KKO that does not activate platelets via FcγRIIA or fix complement may augment the protective effect of PF4 in sepsis by stabilizing hPF4-NET complexes. To investigate this hypothesis, the inventors generated an Fc-modified KKO that retains the ability to bind hPF4-NET complexes but has a reduced capacity to stimulate the inflammatory response. In mice treated with LPS (Efron et al., 2015) and in the murine CLP model of polymicrobial sepsis (Efron et al., 2015), treatment with this modified KKO led to protection from thrombocytopenia, decreased plasma NDP levels, and reduced mortality.

Example 5—Methods for Studies of PF4 and DG-KKO in Sepsis

NET-lined microfluidic channel studies. NET-lined channels were generated as described (Gollomp et al., 2018). Human neutrophils were isolated as in the Supplement Method. Cells (2×10$^{6}$ cells/ml) were incubated with 10 ng/ml TNFα (GIBCO™) and allowed to adhere to channels coated with fibronectin (SIGMA-ALDRICH™) (Hayes et al., 2017). Channels were then incubated with 100 ng/ml PMA (SIGMA-ALDRICH™) in Hank's buffered salt solution (HBSS with calcium and magnesium, GIBCO™) overnight at 37° C. cfDNA was visualized with 1 μM SYTOX green or orange (THERMO FISHER SCIENTIFIC™) also suspended in HBSS. Channels were then infused with hPF4 (0-100 μg/ml). Some channels containing PF4-NET complexes were incubated with 25 μg/ml of KKO, DG-KKO, or a polyclonal anti-PF4 antibody (25 μg/ml, ABCAM™) for 1 hour at 37° C. NET digestion studies were performed by infusing the channels with 100 U/ml DNase I, SIGMA- ALDRICH™) as described (Gollomp et al., 2018). KKO and DG-KKO were labeled with ALEXA FLUOR™ 647 (THERMO FISHER SCIENTIFIC™) prior to channel infusion. All infusions were done at 2-5 dynes/$cm^2$. Experiments were performed using a BIOFLUX™ 200 Controller (Fluxion) (Tutwiler et al., 2016). The BIOFLUX™ channels were visualized with an AXIO™ Observer Z1 inverted ZEISS™ microscope equipped with a motorized stage and an HXP-120 C metal halide illumination source. The microscope and image acquisition were controlled by BIOFLUX™ Montage software with a MetaMorph-based platform (MOLECULAR DEVICES™). Data were analyzed using ImageJ open source image processing software (Gollomp et al., 2015).

In bacterial capture studies, ALEXA FLUOR™ 488-labeled, heat-killed *Staphylococcus* (S) *aureus* (40 μg/ml, Molecular Probes) suspended in HBSS, were infused for 30 minutes at 2 dynes/$cm^2$ into NET channels previously treated with HBSS alone±hPF4 at concentrations of 10 or 100 μg/ml. Bacterial adhesion was quantified as measured by an increase in channel mean fluorescent intensity. Some channels were then infused with DNase I (100 U/ml, SIGMA-ALDRICH™) for 15 minutes. The channels were then infused with Cellfix (BD Biosciences) for 15 minutes prior to imaging with a ZEISS™ LSM 710 laser-scanning confocal microscope.

Mice studied. Mice were WT C57B16 or littermates deficient in murine PF4 ($cxcl4^{-/-}$) or transgenic for platelet-specific expressed hPF4 on a $cxcl4^{-/-}$ background (termed $hPF4^+$ mice) (Reilly et al., 2001) as murine PF4 is not recognized by KKO and most patient HIT antibodies (Li et al., 2002). The inventors have previously found that $hPF4^+$ mice have approximately two times the amount of hPF4 per milligram of total platelet protein as human platelets, expressed exclusively in megakaryocytes and platelets (Lambert et al., 2007). $hPF4^+$ mice that express human FcγRIIA (McKenzie et al., 1999) were used in a HIT passive immunization model (Rauova et al., 2006) to assess DG-KKO's ability to induce thrombocytopenia. Genetic modifications were confirmed by PCR analyses (Zhang et al., 2001). All mice were studied between 10-20 weeks of age. There was an equal distribution of gender in the mice generated, and animals of each gender were randomly studied in the LPS and CLP sepsis, and the HIT passive immunization murine models.

LPS endotoxemia sepsis model. Baseline platelet counts from retro-orbital blood samples were measured using the Hemovet 950 (Drew Scientific). On the following day, WT, $cxcl4^{-/-}$ or $hPF4^+$ mice received an intraperitoneal (IP) injection of LPS (35 mg/kg). 30 minutes later, the mice received a tail vein injection containing of either vehicle alone or KKO, DG-KKO, TRA or DG-TRA at doses of 5 mg/kg diluted in 200 μl of phosphate buffered saline (PBS with $CaCl_2$ and $MgCl_2$, GIBCO™). Five hours after LPS treatment, blood was collected from the retro-orbital plexus and platelet counts were measured. A subset of mice was treated with IP with recombinant DNase I (20 mg/kg, SIGMA-ALDRICH™) 2 hours after LPS injection (Mai et al., 2015). Six hours following LPS injection, a subgroup of animals was sacrificed, blood was collected from the inferior vena cava (IVC), and plasma was isolated. cfDNA was measured using a SYTOX fluorescent plate assay (Sayah et al., 2015), cfDNA-MPO was measured using a previously described ELISA (Caudrillier et al., 2012), and MCP-1 levels were quantified with western blot, using anti-MCP-1 (Cell Signaling Technology, #2027). Another subgroup had MSS calculated and survival noted every 12 hours as described (Zhang et al., 2001) for up to 72 hours. When MSS exceeded 18, the animals were euthanized in accordance with IACUC protocol.

CLP polymicrobial sepsis model. CLP-induced sepsis was induced using a published method (Toscano et al., 2011) in WT, $cxcl4^{-/-}$ and $hPF4^+$ mice. Mice were anesthetized using IP ketamine (150 mg/kg) and xylazine (10 mg/kg) prior to surgical exposure of the cecum (Ruiz et al., 2016). The cecum was exteriorized and ligated with a 6.0 silk suture (6-0 PROLENE, 8680G; Ethicon) placed below the ileo-cecal valve and perforated with a 21-gauge needle (BD Biosciences) to induce mid-grade lethal sepsis (Hubbard et al., 2005; Ebong et al., 1999; Walley et al., 1996). After removing the needle, a small amount of feces was extruded. The cecum was relocated, and the fascia, abdominal musculature, and peritoneum were closed via simple running suture. The control mice were anesthetized and underwent laparotomy without puncture or cecal ligation. Following the procedure, 1 ml of saline was administered subcutaneously (Remick et al., 2000), and the animals received a tail vein injection of PBS, KKO, DG-KKO, TRA or DG-TRA at doses of 5 mg/kg. In some WT mice studies, the animals were given either 20 or 40 mg/kg of hPF4 by tail vein injection. All animals were treated with 0.05 mg/kg buprenorphine every 12 hours to maintain analgesia. In some experiments, ceftriaxone was injected intradermally following surgery (100 mg/kg, Tocris Bioscience). Six hours after surgery, in a subset of mice, blood was collected from the retro-orbital plexus and platelet counts were measured with a HemaVet 950FS (Drew Scientific). Another subset of animals was sacrificed at 48 hours, and blood was obtained from the IVC to measure NDP levels. Another subgroup had MSS calculated and survival noted every 12 hours as described (Sayah et al., 2015) for up to 120 hours.

Antibodies studied and recombinant hPF4. KKO is a mouse $IgG_{2b\kappa}$ anti-hPF4/heparin monoclonal antibody (Arepally et al., 2000). TRA is a monoclonal IgG isotype control antibody (Arepally et al., 2000). Both KKO and TRA were purified from hybridoma supernatants (Arepally et al., 2000). KKO and TRA were deglycosylated using EndoS (IGGZERO®, Genovis) (Hayes et al., 2017) adding 1 unit IGGZERO® to 1 μg of KKO or TRA incubated at 37° C. for 2 hours (Tutwiler et al., 2016). Liquid Chromatography with tandem mass spectrometry (LC-MS/MS) (Reilly et al., 2001) was used to confirm removal of the Fc glycan moieties from KKO (FIG. 17). Recombinant hPF4 was expressed in S2 cells (Li et al., 2002), and purified using affinity chromatography and protein liquid chromatography as previously described (Li et al., 2002). The end-product purity was found to be endotoxin free and was tested for size distribution by gel electrophoresis (SDS-PAGE). Its ability to bind to heparin and yield an immunogenic product was confirmed by ELISA as previously described (Li et al., 2002).

Description of antibodies and other labeled probes. KKO, an anti-PF4/heparin monoclonal antibody, and TRA were purified from hybridoma supernatants. All antibodies were either labeled using ALEXA FLUOR™ antibody-labeling kits according to manufacturer's instructions or species-appropriate ALEXA FLUOR™-conjugated secondary antibodies (all from THERMO FISHER SCIENTIFIC™). Monocyte chemoattractant protein (MCP)-1 was quantified using western blot with rabbit anti-MCP-1 (Cell Signaling Technology, cat no. 2029S) and mouse anti-GAPDH (Cell Signaling Technology, cat no. 97166T) as a control. Mouse TAT complexes were quantified using a commercially available ELISA (Assaypro).

Isolated of human neutrophils. Human blood was collected after informed consent from healthy aspirin-free volunteers through a 19-gauge butterfly needle into 4 ml vacutainers coated with 7.2 mg of ethylenediaminetetraacetic acid (Becton Dickinson). Blood samples were kept at room temperature and used within 1 hour. Neutrophils were isolated with negative bead selection using the MACSXPRESS™ Neutrophil Isolation Kit (MILTENYI™ Biotec). The supernatant was collected and centrifuged at 300 g for 10 minutes, and the cell pellet was resuspended in 2 ml ammonium-chloride-potassium (ACK) lysing buffer (THERMO FISHER SCIENTIFIC™) for 5 minutes to lyse erythrocytes, after which the cells were washed with 10 mls of Hank's balanced salt solution (HBSS, THERMO FISHER SCIENTIFIC™), and then resuspended in HBSS containing calcium chloride (1.3 mM) and then manually counted, with trypan blue dye exclusion (GIBCO™) for cell viability.

Bioassays for NDPs. Released cfDNA was visualized using SYTOX green or orange nucleic acid stain (THERMO FISHER SCIENTIFIC™) and quantified using Sytox green fluorescent plate assay. Briefly, plasma samples were diluted 1:10 in HBSS samples were incubated with SYTOX green (1 μM) and 50 μl were plated in duplicate in a solid black opaque 96-well plate (Corning). A baseline reading was obtained with fluorescence spectrometry, excitation 485 nm and emission 537 nm (SPECTRAMAX™ M2, MOLECULAR DEVICES™). Rabbit anti-cit-H3 (Ab5103, ABCAM™) was used in western blot to quantify cit-H3. Myeloperoxidase was quantified using a commercial ELISA kit cfDNA (Biolegend). MPO-DNA complex levels measured.

Statistical analysis. Differences between 2 groups were compared using a Mann-Whitney U test. Differences between more than 2 groups were determined with a Kruskall-Wallis test or with Sidak's multiple comparisons tests as appropriate. Multiplicity corrected P values are reported for multiple comparisons. Statistical analyses were performed using GRAPHPAD™ Prism 7.0 (GRAPHPAD™ Software). Differences were considered statistically significant when P values were $\leq 0.05$.

Study approval. Animal procedures were approved by the Institutional Animal Care and Use Committee (IACUC) at the Children's Hospital of Philadelphia (CHOP) in accordance with NIH guidelines and the Animal Welfare Act. Anonymized human blood was collected after signed, informed consent was provided by healthy donors. Approval for the use of human blood was obtained from CHOP's Human Review Board in accordance with Declaration of Helsinki Principles.

Example 6—Results for PF4 and DG-KKO Studies in Sepsis

The effect of PF4 on plasma levels of NDPs in murine endotoxemia. The inventors have previously observed that cxcl4$^{-/-}$ mice have increased mortality in LPS endotoxemia compared to hPF4$^{+}$ mice (Kowalska et al., 2007). The infusion of WT mice with platelets obtained from hPF4$^{+}$ animals improved survival (Kowalska et al., 2007). They have recently found that PF4 binds to NETs, leading them to become physically compact and DNase resistant (Gollomp et al., 2018). Therefore, the inventors examined whether NET compaction with NDP sequestration contribute to the protective effects of PF4. They measured NDP levels, including cfDNA, MPO, histone H3, and citrullinated histone H3 (cit-H3) in cxcl4' and hPF4$^{+}$ mice following LPS injection. cxcl4' mice had higher levels of cfDNA and MPO than hPF4$^{+}$ animals 3-8 hours post-LPS exposure (FIGS. 8A and 8B, respectively). H3 levels were on average higher in cxcl4/mice 8 hours following LPS injection, but this difference was not significant. In comparison, levels of cit-H3, a more specific marker of NETosis (Muller et al., 2015), were significantly elevated in cxcl4$^{-/-}$ animals (FIG. 8C). The inventors next explored whether infused hPF4 could recapitulate the protective effect of endogenous PF4 when administered via osmotic pumps or as a single intravenous (IV) bolus. They measured plasma levels of cfDNA and cfDNA-MPO complexes 6-hours post-LPS treatment and found both approaches led to decreased plasma NDPs (FIG. 8D-1F, respectively).

In vitro protective effects of PF4. In sepsis, end-organ injury involves damage to the microvasculature (Martin et al., 2016). Therefore, the inventors sought to determine if PF4-mediated compaction alters NETs' ability to harm the endothelium. To that end, they stimulated isolated human neutrophils with LPS and resuspended the cells in media with and without hPF4 and flowed the samples through human endothelial umbilical vein cell (HUVEC)-lined microfluidic channels that had been stimulated with tumor necrosis factor (TNF)α. The neutrophils readily adhered to the endothelial monolayer, releasing NETs. The presence of PF4 led to NET compaction, although the cfDNA continued to fill the width of the channels (FIG. 18). Flow was discontinued and the HUVECs were incubated with the NET-containing media for 16 hours, after which channels treated with PF4 contained a higher number of residual adherent endothelial cells, suggesting that PF4-bound NETs are less harmful to the endothelium (FIG. 9A).

The inventors then investigated how PF4 binding influences NETs' ability to trap bacteria, another important way NETs impact outcome in sepsis (McDonald et al., 2012). the inventors infused NET-lined channels with heat-inactivated, fluorescently-labeled *S aureus* and quantified bacterial capture with confocal microscopy. PF4-compacted NETs captured a higher number of bacteria that adhered directly to the NET fibers (FIG. 9B, top, FIG. 19). Moreover, when these channels were infused with recombinant human DNase I, PF4-free NETs were rapidly digested, liberating captured bacteria (FIG. 9B, bottom). In contrast, during DNase infusion, compacted PF4-bound NETs remained intact and did not release immobilized bacteria (FIG. 9B, bottom).

Studies of the in vitro effects of DG-KKO. By the time most patients present with the symptoms of sepsis, their platelets have released large amounts of PF4 (Lorenz and Brauer, 1988) that can avidly bind circulating cfDNA (Lande et al., 2019). The inventors' prior observation that the HIT-like monoclonal antibody KKO enhances DNase resistance of hPF4-NET complexes (Gollomp et al., 2018) raised the possibility that KKO may amplify the effect of endogenous PF4 and be of therapeutic benefit in sepsis. However, KKO fixes complement (Khanddelwal et al., 2016), activates platelets (Arepally et al., 2000), and stimulates leukocytes (Gollomp et al., 2018; Rauova et al., 2010), inducing a prothrombotic state in hPF4$^{+}$/FcγRIIA-expressing mice (Hayes et al., 2017) and increasing mortality in murine endotoxemia (see FIG. 12D). They modified KKO by deglycosylating the antibody (Collin and Olsen, 2001) to decrease Fc-mediated injury. Deglycosylated (DG)-KKO was >97% deglycosylated by liquid chromatography with tandem mass spectrometry (LC-MS/MS) (Huang et al., 2014). DG-KKO continued to bind hPF4-heparin and hPF4-NET complexes (FIGS. 10A and 10B, respectively), but had a reduced capacity to activate hPF4-exposed human platelets or induce thrombocytopenia in $hPF4^{+}/Fc\gamma RIIA^{+}$ mice (FIGS. 10C-D). In studies with NET-lined microfluidic channels, DG-KKO did not adhere to non-compacted NETs, but bound hPF4-compacted NETs (FIG. 10E). Like KKO, DG-KKO also increased hPF4-NET resistance to DNase I under flow conditions in microfluidic channels (FIGS. 10F and 103G) and did not impact the ability of PF4-NET complexes to capture bacteria (FIG. 9B).

DG-KKO reduces plasma NDPs and improves outcomes in murine LPS endotoxemia. The inventors next investigated whether treatment with DG-KKO improves outcomes in murine LPS endotoxemia. Thirty minutes post LPS-exposure, mice were given either DG-KKO, or a deglycosylated version of an isotype control antibody DG-TRA (Rauova et al., 2006) via tail vein injections. As both KKO and DG-KKO bind specifically to NET complexes containing hPF4 and not complexes with murine PF4 (FIG. 10E and Li et al., 2002), $hPF4^{+}$ mice were studied. The inventors observed that LPS-exposed $hPF4^{+}$ mice treated with DG-KKO were protected from thrombocytopenia (FIG. 11A). Moreover, animals treated with DG-KKO had lower plasma levels of cfDNA and cfDNA-MPO complexes (FIGS. 11B and 11C) and the inflammatory cytokine monocyte chemoattractant (MCP)-1 (FIG. 11D). DG-KKO treated animals did not have elevated plasma levels of thrombin anti-thrombin (TAT) complexes (FIG. 21), indicating that DG-KKO stabilization of NETs did not accelerate thrombin generation (Koyama et al., 2014). DG-KKO treated mice also had a more benign clinical course, demonstrated by significantly lower mean clinical mouse sepsis scores (MSS; Shrum et al., 2014) at 12 hours (FIG. 11E) and improved overall survival (FIG. 11F). In parallel LPS studies of $cxcl4^{-/-}$ mice, DG-KKO did not exert a protective effect (FIGS. 11A to 11F), supporting that DG-KKO acts through an hPF4-dependent pathway.

Early administration of DNase did not improve outcomes in LPS endotoxemia. The inventors compared the effects of DG-KKO to treatment with DNase in parallel LPS studies shown in FIG. 11 (FIG. 22). They observed that nuclease treatment led worse outcomes in $cxcl4^{-/-}$ mice and no improvement in $hPF4^{+}$ mice. $hPF4^{+}$ mice treated with both DG-KKO and DNase had higher NDP levels and MSSs compared to animals treated with DG-KKO alone (compare FIG. 11 and FIG. 22), supporting their contention that NET-compaction rather than enhanced lysis improves outcome in LPS endotoxemia.

DG-KKO improves outcomes in murine CLP polymicrobial sepsis model. Although treatment with LPS recapitulates many aspects of sepsis, it relies on treatment with a bacterial toxin rather than live pathogens. To determine if PF4 and DG-KKO mitigate NET-associated toxicities, the inventors repeated their endotoxemia experiments using CLP to induce polymicrobial sepsis (Dejager et al., 2011). They performed these experiments in $cxcl4^{-/-}$ and $hPF4^{+}$ mice with and without the administration of the antibiotic ceftriaxone given at a dose that does not improve outcome when used as a single agent (Azeh et al., 2002). They observed no protective effect of DG-KKO in $cxcl4^{-/-}$ mice following CLP (FIG. 12). In contrast, DG-KKO prevented the development of thrombocytopenia in $hPF4^{+}$ mice (FIG. 12A). These animals also had a reduction in plasma cfDNA and cfDNA-MPO complex levels (FIGS. 12B and 12C, respectively) and prolongation of survival (FIG. 12D). Animals co-treated with ceftriaxone and DG-KKO survived CLP (FIG. 12D), demonstrating that NDP sequestration may complement conventional antibiotic strategies in the treatment of polymicrobial sepsis. Studies with unmodified KKO showed that it had no effect in the $cxcl4^{-/-}$ mice, but accelerated death in $hPF4^{+}$ mice, supporting that Fc modification converts KKO from a pathogenic to a therapeutic agent in sepsis.

Co-administration of DG-KKO and hPF4 leads to improved outcomes in CLP in WT mice. The inventors next investigated whether DG-KKO is protective when co-administered with exogenous hPF4 in WT mice. These studies were designed to further support their proposed model and also define the exogenous dose of hPF4 needed to provide clinical benefit in conjunction with an Fc-modified KKO. They observed that WT mice treated with hPF4 alone at doses of 20 mg/kg were not significantly protected following CLP. However, treatment with 40 mg/kg led to decreased thrombocytopenia (FIG. 13A) and lower plasma levels of cfDNA and cfDNA-MPO (FIGS. 13B and 13C, respectively). No protective effect was observed when animals were infused with DG-KKO and bovine serum albumin (BSA). However, mice treated with a combination of DG-KKO and the lower dose of hPF4 (20 mg/kg) did well with the highest platelet counts (FIG. 13A), the lowest plasma NDP levels (FIGS. 13B and 13C), and improved MSSs (FIG. 13D). These results indicate it may be feasible to replicate their murine studies in larger animal models using a combination of exogenous hPF4 and DG-KKO to achieve maximal effect. These results also suggest that co-infusion of hPF4 with DG-KKO may be a superior therapeutic option to either treatment alone.

Example 7—Discussion of Studies of PF4 and DG-KKO in Sepsis

It has been shown that PF4-cfDNA complexes form in vivo during systemic sclerosis (Lande et al., 2019) and it is likely that they also occur in conditions such as sepsis that induce both NETosis and platelet degranulation (McDonald et al., 2017). The inventors have recently shown that PF4 binding enhances NET nuclease resistance without displacing histones (Gollomp et al., 2018). They now show that PF4 protects the endothelium from damage induced by NETs likely by limiting the release of histones as well as other toxic NDPs. They also demonstrate that PF4, which has previously been shown to bind to the surface of bacteria via electrostatic interactions (Krauel et al., 2011), enhances the ability of NETs to entrap *S. aureus*. Cumulatively, their in vitro studies demonstrate that PF4 binding decreases NET toxicity by inhibiting NDP release and enhancing microbial capture. Many species of bacteria release nucleases as a virulence factor to evade capture by NETs (Buchanan et al., 2006; de Burh et al., 2014). They speculated that PF4-mediated NET compaction may be a conserved response that increases NET functionality while decreasing collateral host tissue damage in sepsis. Many biological functions have been attributed to PF4 (Kowalska et al., 2010), but the inventors propose that PF4s' high affinity for polyanionic molecules is related to this critical protective pathway.

They considered whether treatment with exogenous PF4 might improve outcomes in sepsis. However, by the time patients become clinically ill, most septic patients are likely to have a high level of platelet activation and PF4 release (Maharaj and Chang, 2018). As platelet counts and PF4 levels per platelet vary greatly in the general population (Newall et al., 2009; Eicher et al., 2018), the inventors believe that some patients would have low circulating PF4 levels and might benefit from supplemental PF4 infusions, while others may already have sufficiently high levels and receive diminished benefit. Therefore, an alternative and perhaps more effective treatment strategy would be an intervention that stabilizes interactions between NETs and endogenous PF4 (FIG. 14).

It had been shown that PF4 binding to DNA aptamers exposes HIT antigenic sites (Jaax et al., 2013). Therefore, it was not surprising that the HIT-like monoclonal antibody KKO bound specifically to PF4-NET complexes, further enhancing their DNase resistance (Gollomp et al., 2018). KKO, is an $IgG_{2b\kappa}$ antibody that activates Fc receptors and induces complement-dependent cytotoxicity (CDC) (Khandelwal et al., 2018). Therefore, unmodified KKO is injurious in sepsis, as shown in their studies of $hPF4^{+}$ mice (FIG. 5D). $IgG_{2b\kappa}$ antibodies are resistant to cleavage to form $F(ab)_2$ fragments (Andrew and Titus, 2003) and in preliminary studies not shown, the inventors were unable to cleave KKO to generate such fragments. Instead, they treated KKO with EndoS to generate degylcosylated DG-KKO (Nandakumar and Holmdahl, 2008). Deglycosylated antibodies have been used in the treatment of immune-mediated disease and EndoS has been used to deglycosylate pathogenic anti-aquaporin-4 antibodies in neuromyelitis optica, converting them to therapeutic blocking antibodies (Tradtrantip et al., 2013).

The inventors found that DG-KKO had a decreased ability to activate FcγRIIA and fix complement. However, it retained the ability to stabilize PF4-NET complexes, while decreasing NDP release and protecting the endothelial lining, without interfering with NET bacterial entrapment. This translated to an hPF4-dependent improvement in laboratory findings of sepsis, especially NDP release and survival in murine models of sepsis. They speculate that KKO blocks DNase digestion of hPF4-NETs sterically so that DG-KKO may be a more efficacious product than a $F_{(ab)2}$ KKO fragment.

Two alternative NET-based approaches have been proposed to improve outcome in sepsis. One is treatment with DNases. However, their experiments with DNase I infusions are consistent with the results of prior murine CLP studies in which the early administration of DNase leads to increased inflammation and decreased survival (Mai et al., 2015). The inventors found that there was a greater increase in plasma NDP levels following DNase infusion in $Cxcl4^{-/-}$ mice compared to $hPF4^{+}$ mice, showing that PF4 protects NETs from DNase lysis in vivo. Moreover, DG-KKO continues to be protective in $hPF4^{+}$ mice even following DNase infusion suggesting that DG-KKO may remain effective even in the setting of bacteria that release high levels of nucleases.

The other NET-based therapeutic strategy that has been studied is the blockade of NETosis through peptidyl arginine deiminase (PAD) 4 inhibition. While PAD4 blockade may prove to be a useful treatment for autoimmune disease, it is an imperfect strategy in the treatment of sepsis as NETs entrap bacteria and may enhance their killing (Brinkmann et al., 2004). Preventing NETosis could lead to increased bacterial dissemination even in an era when effective antibiotics are often available. To date, published results investigating PAD4 inhibition in murine models of sepsis have been mixed with some studies showing minimal negative effects (Martinod et al., 2015) and others revealing increased vulnerability to infection (McDonald et al., 2012; Li et al., 2010). The second problem with blocking NETosis is that by the time a patient presents with sepsis, their neutrophils have likely already released a large burden of NETs. In clinical studies of patients with septic-shock, levels of cfDNA-MPO were found to be highest at the time of admission (Maruchi et al., 2018). Therefore, even prompt administration of a PAD4 inhibitor is likely to be too late in the treatment of most patients with sepsis.

The inventors' results with PF4 and DG-KKO infusions suggest that in sepsis, NET compaction/stabilization, and NDP and microbial sequestration may be superior to PAD4 blockade or DNase infusion. They have found that it is protective in both sterile LPS endotoxemia and CLP polymicrobial sepsis. Whether it may also be effective in other conditions characterized by NET release including disseminated intravascular coagulation (Alhamdi et al., 2017), SCD (Chen et al., 2014), and APS (Radic et al., 2018) is unclear, and needs to be tested in comparison to alternative strategies.

In summary, the inventors believe that NET compaction and NDP sequestration by infusions of PF4 and/or an Fc-modified HIT-like monoclonal antibody provide new insights into the mechanism by which NETs contribute to the pathophysiology of sepsis. The continued study of this pathway may lead to the development of targeted therapeutics to improve outcome in sepsis and perhaps other disorders associated with excess NET release.

References for Examples 4-7

The following references, to the extent that they provide exemplary procedural or other details supplementary to those set forth herein, are specifically incorporated herein by reference.

Angus D C, Linde-Zwirble W T, Lidicker J, Clermont G, Carcillo J, Pinsky M R. Epidemiology of severe sepsis in the United States: analysis of incidence, outcome, and associated costs of care. *Crit Care Med.* 2001; 29(7): 1303-1310. Mayr F B, Yende S, Angus D C. Epidemiology of severe sepsis. Virulence. 2014; 5(1):4-11.

Coopersmith C M, De Backer D, Deutschman C S, et al. Surviving sepsis campaign: research priorities for sepsis and septic shock. *Intensive Care Med.* 2018.

Jackson S P, Darbousset R, Schoenwaelder S M. Thromboinflammation: Challenges of Therapeutically Targeting Coagulation and other Host Defence Mechanisms. *Blood.* 2019.

Gyawali B, Ramakrishna K, Dhamoon A S. Sepsis: The evolution in definition, pathophysiology, and management. *SAGE Open Med.* 2019; 7:2050312119835043.

Coopersmith C M, De Backer D, Deutschman C S, et al. Surviving Sepsis Campaign: Research Priorities for Sepsis and Septic Shock. *Crit Care Med.* 2018; 46(8):1334-1356.

Delano M J, Ward P A. Sepsis-induced immune dysfunction: can immune therapies reduce mortality? *J Clin Invest.* 2016; 126(1):23-31.

Kubes P. The enigmatic neutrophil: what we do not know. *Cell Tissue Res.* 2018; 371(3):399-406.

McDonald B, Urrutia R, Yipp B G, Jenne C N, Kubes P. Intravascular neutrophil extracellular traps capture bacteria from the bloodstream during sepsis. *Cell Host Microbe.* 2012; 12(3):324-333.

Schauer C, Janko C, Munoz L E, et al. Aggregated neutrophil extracellular traps limit inflammation by degrading cytokines and chemokines. *Nat Med.* 2014; 20(5):511-517.

Mahajan A, Gruneboom A, Petru L, et al. Frontline Science: Aggregated neutrophil extracellular traps prevent inflammation on the neutrophil-rich ocular surface. *J Leukoc Biol.* 2019.

Jimenez-Alcazar M, Rangaswamy C, Panda R, et al. Host DNases prevent vascular occlusion by neutrophil extracellular traps. *Science.* 2017; 358(6367):1202-1206.

Bhagirath V C, Dwivedi D J, Liaw P C. Comparison of the Proinflammatory and Procoagulant Properties of Nuclear, Mitochondrial, and Bacterial DNA. *Shock.* 2015; 44(3): 265-271.

Leffler J, Martin M, Gullstrand B, et al. Neutrophil extracellular traps that are not degraded in systemic lupus erythematosus activate complement exacerbating the disease. *J Immunol.* 2012; 188(7):3522-3531.

Tian R, Ding Y, Peng Y Y, Lu N. Inhibition of Myeloperoxidase- and Neutrophil-Mediated Hypochlorous Acid Formation in vitro and Endothelial Cell Injury by (-)-Epigallocatechin Gallate. *J Agric Food Chem.* 2017; 65(15):3198-3203.

Massberg S, Grahl L, von Bruehl M L, et al. Reciprocal coupling of coagulation and innate immunity via neutrophil serine proteases. *Nat Med.* 2010; 16(8):887-896.

Esmon C T. Extracellular histones zap platelets. *Blood.* 2011; 118(13):3456-3457.

Xu J, Zhang X, Pelayo R, et al. Extracellular histones are major mediators of death in sepsis. *Nat Med.* 2009; 15(11):1318-1321.

Maruchi Y, Tsuda M, Mori H, et al. Plasma myeloperoxidase-conjugated DNA level predicts outcomes and organ dysfunction in patients with septic shock. *Crit Care.* 2018; 22(1):176.

Colon D F, Wanderley C W, Franchin M, et al. Neutrophil extracellular traps (NETs) exacerbate severity of infant sepsis. *Crit Care.* 2019; 23(1):113.

Martinod K, Fuchs T A, Zitomersky N L, et al. PAD4-deficiency does not affect bacteremia in polymicrobial sepsis and ameliorates endotoxemic shock. *Blood.* 2015; 125(12):1948-1956.

McDonald B, Davis R P, Kim S J, et al. Platelets and neutrophil extracellular traps collaborate to promote intravascular coagulation during sepsis in mice. *Blood.* 2017; 129(10):1357-1367.

O'Brien X M, Biron B M, Reichner J S. Consequences of extracellular trap formation in sepsis. *Curr Opin Hematol.* 2017; 24(1):66-71.

Mai S H, Khan M, Dwivedi D J, et al. Delayed but not Early Treatment with DNase Reduces Organ Damage and Improves Outcome in a Murine Model of Sepsis. *Shock.* 2015; 44(2):166-172.

Hurley J C. Antibiotic-induced release of endotoxin. A therapeutic paradox. *Drug Saf.* 1995; 12(3):183-195.

Eslin D E, Zhang C, Samuels K J, et al. Transgenic mice studies demonstrate a role for platelet factor 4 in thrombosis: dissociation between anticoagulant and antithrombotic effect of heparin. *Blood.* 2004; 104(10):3173-3180.

Cines D B, Rauova L, Arepally G, et al. Heparin-induced thrombocytopenia: an autoimmune disorder regulated through dynamic autoantigen assembly/disassembly. *J Clin Apher.* 2007; 22(1):31-36.

Lande R, Lee E Y, Palazzo R, et al. CXCL4 assembles DNA into liquid crystalline complexes to amplify TLR9-mediated interferon-alpha production in systemic sclerosis. *Nat Commun.* 2019; 10(1):1731.

Gollomp K, Kim M, Johnston I, et al. Neutrophil accumulation and NET release contribute to thrombosis in HIT. *JCI Insight.* 2018; 3(18).

Kowalska M A, Mahmud S A, Lambert M P, Poncz M, Slungaard A. Endogenous platelet factor 4 stimulates activated protein C generation in vivo and improves survival after thrombin or lipopolysaccharide challenge. *Blood.* 2007; 110(6):1903-1905.

Arepally G M, Kamei S, Park K S, et al. Characterization of a murine monoclonal antibody that mimics heparin-induced thrombocytopenia antibodies. *Blood.* 2000; 95(5): 1533-1540.

Efron P A, Mohr A M, Moore F A, Moldawer L L. The future of murine sepsis and trauma research models. *J Leukoc Biol.* 2015; 98(6):945-952.

Hayes V, Johnston I, Arepally G M, et al. Endothelial antigen assembly leads to thrombotic complications in heparin-induced thrombocytopenia. *J Clin Invest.* 2017; 127(3):1090-1098.

Tutwiler V, Madeeva D, Ahn H S, et al. Platelet transactivation by monocytes promotes thrombosis in heparin-induced thrombocytopenia. *Blood.* 2016; 127(4):464-472.

Reilly M P, Taylor S M, Hartman N K, et al. Heparin-induced thrombocytopenia/thrombosis in a transgenic mouse model requires human platelet factor 4 and platelet activation through FcgammaRIIA. *Blood.* 2001; 98(8): 2442-2447.

Li Z Q, Liu W, Park K S, et al. Defining a second epitope for heparin-induced thrombocytopenia/thrombosis antibodies using KKO, a murine HIT-like monoclonal antibody. *Blood.* 2002; 99(4):1230-1236.

Lambert M P, Rauova L, Bailey M, Sola-Visner M C, Kowalska M A, Poncz M. Platelet factor 4 is a negative autocrine in vivo regulator of megakaryopoiesis: clinical and therapeutic implications. *Blood.* 2007; 110(4):1153-1160.

McKenzie S E, Taylor S M, Malladi P, et al. The role of the human Fc receptor Fc gamma RIIA in the immune clearance of platelets: a transgenic mouse model. *J Immunol.* 1999; 162(7):4311-4318.

Rauova L, Zhai L, Kowalska M A, Arepally G M, Cines D B, Poncz M. Role of platelet surface PF4 antigenic complexes in heparin-induced thrombocytopenia pathogenesis: diagnostic and therapeutic implications. *Blood.* 2006; 107(6):2346-2353.

Zhang C, Thornton M A, Kowalska M A, et al. Localization of distal regulatory domains in the megakaryocyte-specific platelet basic protein/platelet factor 4 gene locus. *Blood.* 2001; 98(3):610-617.

Sayah D M, Mallavia B, Liu F, et al. Neutrophil extracellular traps are pathogenic in primary graft dysfunction after lung transplantation. *Am J Respir Crit Care Med.* 2015; 191(4):455-463.

Caudrillier A, Looney M R. Platelet-neutrophil interactions as a target for prevention and treatment of transfusion-related acute lung injury. *Curr Pharm Des.* 2012; 18(22): 3260-3266.

Toscano M G, Ganea D, Gamero A M. Cecal ligation puncture procedure. *J Vis Exp.* 2011(51). Ruiz S, Vardon-Bounes F, Merlet-Dupuy V, et al. Sepsis modeling in mice: ligation length is a major severity factor in cecal ligation and puncture. *Intensive Care Med Exp.* 2016; 4(1):22.

Hubbard W J, Choudhry M, Schwacha M G, et al. *Cecal ligation and puncture. Shock.* 2005; 24 Suppl 1:52-57.

Ebong S, Call D, Nemzek J, Bolgos G, Newcomb D, Remick D. Immunopathologic alterations in murine models of sepsis of increasing severity. *Infect Immun.* 1999; 67(12):6603-6610.

Walley K R, Lukacs N W, Standiford T J, Strieter R M, Kunkel S L. Balance of inflammatory cytokines related to severity and mortality of murine sepsis. *Infect Immun.* 1996; 64(11):4733-4738.

Remick D G, Newcomb D E, Bolgos G L, Call D R. Comparison of the mortality and inflammatory response of two models of sepsis: lipopolysaccharide vs. cecal ligation and puncture. *Shock.* 2000; 13(2):110-116.

Muller S, Radic M. Citrullinated Autoantigens: From Diagnostic Markers to Pathogenetic Mechanisms. *Clin Rev Allergy Immunol.* 2015; 49(2):232-239.

Martin L, Koczera P, Zechendorf E, Schuerholz T. The Endothelial Glycocalyx: New Diagnostic and Therapeutic Approaches in Sepsis. *Biomed Res Int.* 2016; 2016: 3758278.

Lorenz R, Brauer M. Platelet factor 4 (PF4) in septicaemia. *Infection.* 1988; 16(5):273-276.

Khandelwal S, Lee G M, Hester C G, et al. The antigenic complex in HIT binds to B cells via complement and complement receptor 2 (CD21). *Blood.* 2016; 128(14): 1789-1799.

Rauova L, Hirsch J D, Greene T K, et al. Monocyte-bound PF4 in the pathogenesis of heparin-induced thrombocytopenia. *Blood.* 2010; 116(23):5021-5031.

Collin M, Olsen A. EndoS, a novel secreted protein from *Streptococcus pyogenes* with endoglycosidase activity on human IgG. *EMBO J.* 2001; 20(12):3046-3055.

Huang L J, Lin J H, Tsai J H, et al. Identification of protein O-glycosylation site and corresponding glycans using liquid chromatography-tandem mass spectrometry via mapping accurate mass and retention time shift. *J Chromatogr A.* 2014; 1371:136-145.

Koyama K, Madoiwa S, Nunomiya S, et al. Combination of thrombin-antithrombin complex, plasminogen activator inhibitor-1, and protein C activity for early identification of severe coagulopathy in initial phase of sepsis: a prospective observational study. *Crit Care.* 2014; 18(1):R13.

Shrum B, Anantha R V, Xu S X, et al. A robust scoring system to evaluate sepsis severity in an animal model. *BMC Res Notes.* 2014; 7:233.

Dejager L, Pinheiro I, Dejonckheere E, Libert C. Cecal ligation and puncture: the gold standard model for polymicrobial sepsis? *Trends Microbiol.* 2011; 19(4):198-208.

Azeh I, Gerber J, Wellmer A, et al. Protein synthesis inhibiting clindamycin improves outcome in a mouse model of *Staphylococcus aureus* sepsis compared with the cell wall active ceftriaxone. *Crit Care Med.* 2002; 30(7): 1560-1564.

Krauel K, Potschke C, Weber C, et al. Platelet factor 4 binds to bacteria, [corrected] inducing antibodies cross-reacting with the major antigen in heparin-induced thrombocytopenia. *Blood.* 2011; 117(4):1370-1378.

Buchanan J T, Simpson A J, Aziz R K, et al. DNase expression allows the pathogen group A *Streptococcus* to escape killing in neutrophil extracellular traps. *Curr Biol.* 2006; 16(4):396-400.

de Buhr N, Neumann A, Jerjomiceva N, von Kockritz-Blickwede M, Baums C G. *Streptococcus suis* DNase SsnA contributes to degradation of neutrophil extracellular traps (NETs) and evasion of NET-mediated antimicrobial activity. *Microbiology.* 2014; 160(Pt 2):385-395.

Kowalska M A, Rauova L, Poncz M. Role of the platelet chemokine platelet factor 4 (PF4) in hemostasis and thrombosis. *Thromb Res.* 2010; 125(4):292-296.

Maharaj S, Chang S. Anti-PF4/heparin antibodies are increased in hospitalized patients with bacterial sepsis. *Thromb Res.* 2018; 171:111-113.

Jackson S P, Darbousset R, Schoenwaelder S M. Thromboinflammation: challenges of therapeutically targeting coagulation and other host defense mechanisms. *Blood.* 2019; 133(9):906-918.

Newall F, Johnston L, Ignjatovic V, Summerhayes R, Monagle P. Age-related plasma reference ranges for two heparin-binding proteins—vitronectin and platelet factor 4. *Int J Lab Hematol.* 2009; 31(6):683-687.

Eicher J D, Lettre G, Johnson A D. The genetics of platelet count and volume in humans. *Platelets.* 2018; 29(2):125-130.

Jaax M E, Krauel K, Marschall T, et al. Complex formation with nucleic acids and aptamers alters the antigenic properties of platelet factor 4. *Blood.* 2013; 122(2):272-281.

Khandelwal S, Ravi J, Rauova L, et al. Polyreactive IgM initiates complement activation by PF4/heparin complexes through the classical pathway. *Blood.* 2018; 132 (23):2431-2440.

Andrew S M, Titus J A. Fragmentation of immunoglobulin G. *Curr Protoc Cell Biol.* 2003; Chapter 16:Unit 16 14.

Nandakumar K S, Holmdahl R. Therapeutic cleavage of IgG: new avenues for treating inflammation. *Trends Immunol.* 2008; 29(4):173-178.

Tradtrantip L, Asavapanumas N, Verkman A S. Therapeutic cleavage of anti-aquaporin-4 autoantibody in neuromyelitis optica by an IgG-selective proteinase. *Mol Pharmacol.* 2013; 83(6):1268-1275.

Brinkmann V, Reichard U, Goosmann C, et al. Neutrophil extracellular traps kill bacteria. *Science.* 2004; 303(5663): 1532-1535.

Li P, Li M, Lindberg M R, Kennett M J, Xiong N, Wang Y. PAD4 is essential for antibacterial innate immunity mediated by neutrophil extracellular traps. *J Exp Med.* 2010; 207(9):1853-1862.

Alhamdi Y, Toh C H. Recent advances in pathophysiology of disseminated intravascular coagulation: the role of circulating histones and neutrophil extracellular traps. *F*1000*Res.* 2017; 6:2143.

Chen G, Zhang D, Fuchs T A, Manwani D, Wagner D D, Frenette P S. Heme-induced neutrophil extracellular traps contribute to the pathogenesis of sickle cell disease. *Blood.* 2014; 123(24):3818-3827.

Radic M, Pattanaik D. Cellular and Molecular Mechanisms of Anti-Phospholipid Syndrome. Front Immunol. 2018; 9:969.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

What is claimed:

1. A method of treating a subject having or at risk of developing bacterial sepsis comprising administering to said subject a modified KKO antibody or fragment thereof that binds immunologically to platelet factor 4 (PF4) complexed to neutrophil extracellular traps (NETs), wherein said administered modified KKO antibody or fragment thereof exhibits reduced binding to FcR and/or complement activation as compared to an unmodified KKO antibody or fragment thereof.

2. The method of claim 1, wherein the modified KKO antibody or fragment thereof is a deglycosylated KKO antibody.

3. The method of claim 1, wherein the modified KKO antibody or fragment thereof is modified by a mutation in the Fc domain by an amino acid substitution and/or is an IgG subclass switch.

4. The method of claim 1, wherein the subject is a human.

5. The method of claim 1, wherein the subject is a non-human mammal.

6. The method of claim 1, wherein the subject has bacterial sepsis.

7. The method of claim 1, wherein the subject is at risk of having bacterial sepsis.

8. The method of claim 1, further comprising treating said subject with a second anti-bacterial sepsis therapy.

9. The method of claim 8, wherein said anti-bacterial sepsis therapy is an antibiotic, IV fluids, blood products, a vasopressor, or a steroid.

10. The method of claim 1, wherein said modified KKO antibody or fragment thereof is administered intravenously, intra-arterially, intramuscularly or subcutaneously.

11. The method of claim 1, wherein said antibody or fragment thereof is administered more than once.

12. The method of claim 1, wherein said modified KKO antibody is an IgG or IgM.

13. A modified KKO antibody or fragment thereof that binds immunologically to platelet factor 4 (PF4), wherein said KKO antibody or fragment thereof exhibits reduced binding to FcR and/or complement activation as compared to an unmodified KKO antibody or fragment thereof of the same class and isotype.

14. The modified KKO antibody or fragment thereof of claim 13, wherein the modified KKO antibody or fragment thereof is a deglycosylated KKO antibody or fragment and/or is modified by a mutation in the Fc domain by an amino acid substitution or is an IgG subclass switch.

15. The modified KKO antibody or fragment thereof of claim 13, formulated in a pharmaceutically acceptable excipient.

16. The modified KKO antibody or fragment thereof of claim 13, formulated with an antibiotic, IV fluids, blood products, a vasopressor, or a steroid.

17. The modified KKO antibody or fragment thereof of claim 13, wherein said antibody is an IgG or IgM.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1

cctaagggct acacaacctt                                                20


<210> SEQ ID NO 2
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 2

gctggctgct ttcacctgta c                                              21


<210> SEQ ID NO 3
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 3

catctgttct gctgctggct g                                              21


<210> SEQ ID NO 4
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 4

ctcctaaggg ctacacaacc ttc                                            23
```